US008138215B2

(12) United States Patent
Lopez et al.

(10) Patent No.: US 8,138,215 B2
(45) Date of Patent: Mar. 20, 2012

(54) HEPATITIS C VIRUS INHIBITORS

(75) Inventors: Omar D. Lopez, Wallingford, CT (US); Qi Chen, Norwalk, CT (US); Makonen Belema, North Haven, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 12/780,415

(22) Filed: May 14, 2010

(65) Prior Publication Data

US 2010/0303755 A1 Dec. 2, 2010

Related U.S. Application Data

(60) Provisional application No. 61/182,403, filed on May 29, 2009.

(51) Int. Cl.
*A61K 31/4174* (2006.01)
*C07D 233/64* (2006.01)
(52) U.S. Cl. .................................. 514/397; 548/313.1
(58) Field of Classification Search ............... 548/313.1; 514/397

See application file for complete search history.

(56) References Cited

U.S. PATENT DOCUMENTS

| 5,654,451 | A | 8/1997 | Kari |
| 7,894,996 | B2 | 2/2011 | Rice et al. |
| 2010/0158862 | A1 | 6/2010 | Kim et al. |
| 2011/0092415 | A1 | 4/2011 | Degoey et al. |

FOREIGN PATENT DOCUMENTS

| WO | WO 94/015909 | 7/1994 |
| WO | WO 2004/005264 | 1/2004 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/014430 | 1/2008 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/075376 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096777 | 8/2010 |
| WO | WO 2010/099527 | 9/2010 |
| WO | WO 2010/111483 | 9/2010 |
| WO | WO 2010/111534 | 9/2010 |
| WO | WO 2010/111673 | 9/2010 |
| WO | WO 2010/117635 | 10/2010 |
| WO | WO 2010/117704 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO-2010132601 | * 11/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/009084 | 1/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |

(Continued)

OTHER PUBLICATIONS

U.S. Appl. No. 12/846,152, filed Jul. 29, 2010, Romine.
U.S. Appl. No. 12/889,705, filed Sep. 24, 2010, Belema et al.
U.S. Appl. No. 13/195,317, filed Aug. 1, 2011, Gao et al.
U.S. Appl. No. 13/198,529, filed Aug. 4, 2011, Belema et al.
Fridell, R.A. et al., "Resistance Analysis of the Hepatitis C Virus NS5A Inhibitor BMS-790052 in an In VItro Replicon System", Antimicrobial Agents and Chemotherapy, vol. 54, No. 9, pp. 3641-3650 (2010).
Gao, M. et al., "Chemical genetics strategy identifies an HCV NS5A inhibitor with a potent clinical effect", Nature, vol. 465, pp. 96-100 (2010).
Lemm, J.A. et al., "Identification of Hepatitis C Virus NS5A Inhibitors", Journal of Virology, vol. 84, No. 1, pp. 482-491 (2010).
Romine, J. L. et al., "Inhibitors of HCV NS5A: From Iminothiazolidinones to Symmetrical Stilbenes", ACS Medical Chemistry Letters, vol. 2, pp. 224-229 (2011).

*Primary Examiner* — Kamal Saeed
*Assistant Examiner* — Janet L Coppins
(74) *Attorney, Agent, or Firm* — Pamela A. Mingo

(57) ABSTRACT

The present disclosure relates to compounds, compositions and methods for the treatment of hepatitis C virus (HCV) infection. Also disclosed are pharmaceutical compositions containing such compounds and methods for using these compounds in the treatment of HCV infection.

17 Claims, No Drawings

FOREIGN PATENT DOCUMENTS

| | | |
|---|---|---|
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/060000 | 5/2011 |
| WO | WO 2011/066241 | 6/2011 |
| WO | WO 2011/068941 | 6/2011 |
| WO | WO 2011/075439 | 6/2011 |
| WO | WO 2011/075607 | 6/2011 |
| WO | WO 2011/075615 | 6/2011 |
| WO | WO 2011/079327 | 6/2011 |
| WO | WO 2011/081918 | 7/2011 |
| WO | WO 2011/082077 | 7/2011 |
| WO | WO 2011/087740 | 7/2011 |
| WO | WO 2011/091417 | 7/2011 |
| WO | WO 2011/091446 | 7/2011 |
| WO | WO 2011/091532 | 8/2011 |

* cited by examiner

HEPATITIS C VIRUS INHIBITORS

CROSS-REFERENCE TO RELATED APPLICATIONS

This application claims the benefit of U.S. Provisional Application Ser. No. 61/182,403 filed May 29, 2009.

FIELD OF THE DISCLOSURE

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

BACKGROUND OF THE DISCLOSURE

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this unmet medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); C. Rice, et al., WO2006093867.

SUMMARY OF THE DISCLOSURE

In a first aspect the present disclosure provides a compound of Formula (I)

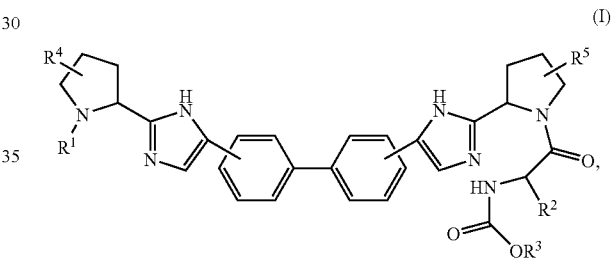

(I)

or a pharmaceutically acceptable salt thereof, wherein $R^1$ is selected from hydrogen, —C(O)$R^6$, and

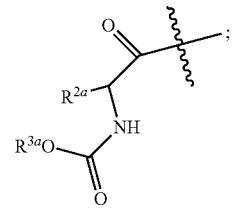

;

$R^2$ and $R^{2a}$ are independently selected from hydrogen, alkyl, and aryl;

$R^3$ is cycloalkyl;

$R^{3a}$ is cycloalkyl;

$R^4$ and $R^5$ are independently selected from hydrogen and alkyl; wherein the alkyl can optionally form a fused three- to six-membered ring with an adjacent carbon atom or optionally form a spirocyclic three- to six-membered ring with the carbon to which it is attached; and $R^6$ is selected from alkoxy, alkyl, arylalkoxy, arylalkyl, cycloalkyl, heterocyclyl, heterocyclylalkyl, (NR$^c$R$^d$)alkenyl, and (NR$^c$R$^d$)alkyl.

DETAILED DESCRIPTION OF THE DISCLOSURE

In a first embodiment of the first aspect the present disclosure provides a compound of Formula (I), or a pharmaceutically acceptable salt thereof, wherein $R^1$ is —C(O)$R^6$.

In a second embodiment of the first aspect the present disclosure provides a compound of Formula (I) wherein $R^1$ is

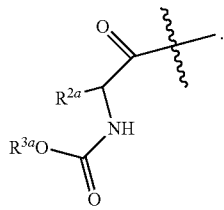

In a third embodiment of the first aspect the present disclosure provides a compound of Formula (I) wherein $R^1$ is

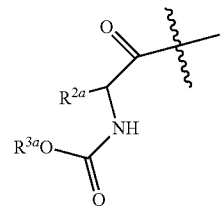

and $R^2$ and $R^{2a}$ are each phenyl. In a fourth embodiment $R^4$ and $R^5$ are each hydrogen.

In a fifth embodiment of the first aspect the present disclosure provides a compound of Formula (I) wherein $R^1$ is

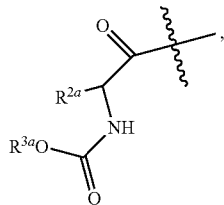

$R^2$ and $R^{2a}$ are each phenyl, and $R^4$ and $R^5$ are each alkyl, wherein each alkyl group can optionally form a fused three- to six-membered ring with an adjacent carbon atom or optionally form a spirocyclic three- to six-membered ring with the carbon to which it is attached. In a sixth embodiment $R^4$ and $R^5$ are each alkyl, wherein each alkyl group forms a fused three-membered ring with an adjacent carbon atom.

In a second aspect the present disclosure provides a compound of Formula (II)

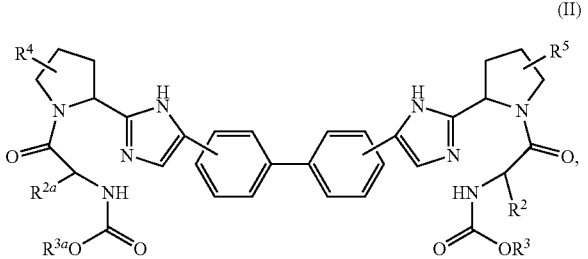

or a pharmaceutically acceptable salt thereof, wherein $R^2$ and $R^{2a}$ are independently selected from hydrogen, alkyl, and phenyl;

$R^3$ is $C_{3-7}$ cycloalkyl;

$R^{3a}$ is $C_{3-7}$ cycloalkyl; and $R^4$ and $R^5$ are independently selected from hydrogen and alkyl; wherein the alkyl can optionally form a fused three-membered ring with an adjacent carbon atom.

In a third aspect the present disclosure provides a composition comprising a compound of Formula (I), or a pharmaceutically acceptable salt thereof, and a pharmaceutically acceptable carrier. In a first embodiment of the third aspect the composition further comprises at least one additional compound having anti-HCV activity. In a second embodiment of the third aspect at least one of the additional compounds is an interferon or a ribavirin. In a fourth embodiment the interferon is selected from interferon alpha 2B, pegylated interferon alpha, consensus interferon, interferon alpha 2A, and lymphoblastoid interferon tau.

In a fifth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a sixth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of Formula (I), or a pharmaceutically acceptable salt thereof. In a first embodiment of the fourth aspect the method further comprises administering at least one additional compound having anti-HCV activity prior to, after or simultaneously with the compound of Formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastoid interferon tau.

In a fourth embodiment of the fourth aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other embodiments of the present disclosure may comprise suitable combinations of two or more of embodiments and/or aspects disclosed herein. Yet other embodiments and aspects of the disclosure will be apparent according to the description provided below.

The compounds of the present disclosure also exist as tautomers; therefore the present disclosure also encompasses all tautomeric forms.

The description of the present disclosure herein should be construed in congruity with the laws and principals of chemical bonding.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

DEFINITIONS

As used in the present specification, the following terms have the meanings indicated:

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to six carbon atoms. In the compounds of the present disclosure, when $R^4$ and/or $R^5$ is alkyl, each alkyl can optionally form a fused three- to six-membered ring with an adjacent carbon atom to provide any of the structures shown below:

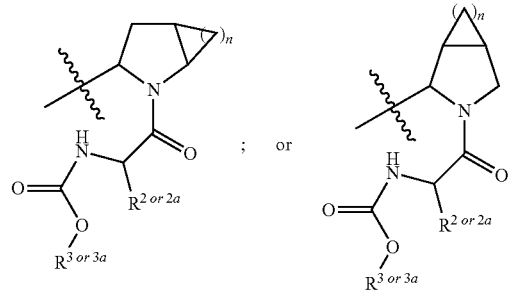

wherein n is 1-4, or can optionally form a spirocyclic three- to six-membered ring with the carbon to which it is attached to provide the structure shown below:

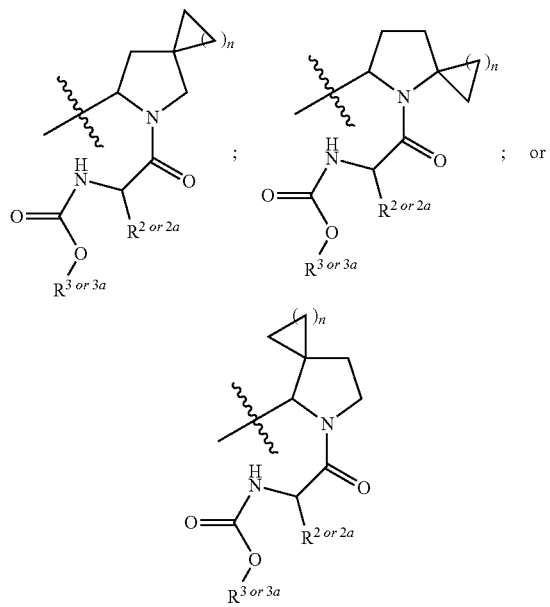

wherein n is 1-4.

The term "alkylcarbonyl," as used herein, refers to an alkyl group attached to the parent molecular moiety through a carbonyl group.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkenyl, alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^x$R$^y$, (NR$^x$R$^y$) alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkoxy," as used herein, refers to an arylalkyl group attached to the parent molecular moiety through an oxygen atom.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, —NR$^x$R$^y$, and oxo.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "arylsulfonyl," as used herein, refers to an aryl group attached to the parent molecular moiety through a sulfonyl group.

The term "carbonyl," as used herein, refers to —C(O)—.

The term "carboxy," as used herein, refers to —CO$_2$H.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclobutyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "C$_{3-7}$ cycloalkyl," as used herein, refers to a saturated monocyclic, hydrocarbon unsubstituted ring system having three to seven carbon atoms and zero heteroatoms. Representative examples of cycloalkyl groups include, but are not limited to, cyclopropyl, cyclobutyl, cyclopentyl, and cyclohexyl.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refers to Cl, Br, F, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oct-2-yl, and 2-azabicyclo[2.2.2]oct-3-yl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, quinolinyl, thiazolyl, thienyl, and thiomorpholinyl. The heterocyclyl groups of the present disclosure are optionally substituted with one, two, three, four, or five substituents independently selected from alkenyl, alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$) alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkoxy," as used herein, refers to a heterocylyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —NO$_2$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxy, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to

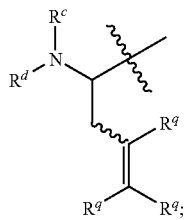

wherein R$^c$ and R$^d$ are as defined herein and each Rq is independently hydrogen or C$_{1-3}$ alkyl.

The term "(NR$^c$R$^d$)alkyl," as used herein, refers to an alkyl group substituted with one or two —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxycarbonyl, carboxy, cycloalkyl, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cycloalkyl)alkyl, unsubstituted heterocyclyl, unsubstituted heterocyclylalkyl, (NR$^x$R$^y$)alkyl, and (NR$^e$R$^f$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "(NR$^x$R$^y$," as used herein, refers to two groups, R$^x$ and R$^y$, which are attached to the parent molecular moiety through a nitrogen atom. R$^x$ and R$^y$ are independently selected from hydrogen and alkyl.

The term "(NR$^x$R$^y$)alkyl," as used herein, refers to an alkyl group substituted with one, two, or three —NR$^x$R$^y$ groups.

The term "(NR$^x$R$^y$)carbonyl," as used herein, refers to an —NR$^x$R$^y$ group attached to the parent molecular moiety through a carbonyl group.

The term "oxo," as used herein, refers to =O.

The term "sulfonyl," as used herein, refers to —SO$_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steno hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like, Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the fowl of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharm. Res.*, 3(6):318 (1986).

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and sautes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology*, 38:1282 (2003); *Biochem. Biophys. Res. Commun.*, 313:42 (2004); *J. Gastroenterol.*, 38:567 (2003)).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis |
| Debio-025 | | | Debiopharm |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novarits |
| 2' C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2' C Methyl adenosine | Antiviral | NS5B replicase inhibitor | Mereck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |

TABLE 1-continued

| Brand Name | Physiological Class | Type of Inhibitor or Target | Source Company |
|---|---|---|---|
| Ribavirin | Antiviral | Ribavirin | Schering-Plough Corparation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering Plough |
| Zadazim | Immune modulator | Immune modulator | SciClone Pharmaceeuticals Inc., San Mateo, CA |
| Ceplene | Immunomodulator | Immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ ribavirin | Schering-Plough Corporation, Kenilworth, NJ |
| IP-501 | Liver protection | Antifibrotic | Indevus Pharmaceuticals Inc., Lexington, MA |

TABLE 1-continued

| Brand Name | Physiological Class | Type of Inhibitor or Target | Source Company |
|---|---|---|---|
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| Peg-interferon lamda | Antiviral | Interferon | ZymoGenetics/ Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: TFA for trifluoroacetic acid; min for minutes; DMSO for dimethylsulfoxide; RT for room temperature or retention time (context will dictate); and $R_t$ for retention time; THF for tetrahydrofuran; EDCI for 1-ethyl-3-(3-dimethylaminopropyl)carbodiimide; DMAP for N,N-dimethylaminopyridine; DMF for 1,8-diazabicyclo[5.4.0]undec-7-ene; DEA for diethylamine; HMDS for hexamethyldisilazide; EtOAC or EtOAc for ethyl acetate; DMF for N,N-dimethylformamide; MeOH for methanol; Bn for benzyl; Me for methyl; $Et_3N$ for triethylamine; DIBAL or DIBALH for diisobutylaluminum hydride; i-PrOH or iPrOH for isopropanol; TBDMS for tert-butyldimethylsilyl; h for hours; Boc or BOC for tert-butoxycarbonyl; DMA for N,N-dimethylacetamide; OAc for adetate; and DIPEA or DMA for diisopropylethylamine.

The compounds and processes of the present disclosure will be better understood in connection with the following synthetic schemes which illustrate the methods by which the compounds of the present disclosure may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

Synthetic Methods

Scheme 1: Substituted Phenylglycine Derivatives

Substituted phenylglycine derivatives can be prepared by a number of methods shown below. Phenylglycine t-butyl ester can be reductively alkylated (pathway A) with an appropriate aldehyde and a reductant such as sodium cyanoborohydride in acidic medium. Hydrolysis of the t-butyl ester can be accomplished with strong acid such as HCl or trifluoroacetic acid. Alternatively, phenylglycine can be alkylated with an alkyl halide such as ethyl iodide and a base such as sodium bicarbonate or potassium carbonate (pathway B). Pathway C illustrates reductive alkylation of phenylglycine as in pathway A followed by a second reductive alkylation with an alternate aldehyde such as formaldehyde in the presence of a reducing agent and acid. Pathway D illustrates the synthesis of substituted phenylglycines via the corresponding mandelic acid analogs. Conversion of the secondary alcohol to a competent leaving group can be accomplished with p-toluenesulfonyl chloride. Displacement of the tosylate group with an appropriate amine followed by reductive removal of the benzyl ester can provide substituted phenylglycine derivatives. In pathway E a racemic substituted phenylglycine derivative is resolved by esterification with an enantiomerically pure chiral auxiliary such as but not limited to (+)-1-phenylethanol, (−)-1-phenylethanol, an Evan's oxazolidinone, or enantiomerically pure pantolactone. Separation of the diastereomers is accomplished via chromatography (silica gel, HPLC, crystallization, etc) followed by removal of the chiral auxiliary providing enantiomerically pure phenylglycine derivatives. Pathway H illustrates a synthetic sequence which intersects with pathway E wherein the aforementioned chiral auxiliary is installed prior to amine addition. Alternatively, an ester of an arylacetic acid can be brominated with a source of bromonium ion such as bromine, N-bromosuccinimide, or $CBr_4$. The resultant benzylic bromide can be displaced with a variety of mono- or disubstituted amines in the presence of a tertiary amine base such as triethylamine or Hunig's base. Hydrolysis of the methyl ester via treatment with lithium hydroxide at low temperature or 6N HCl at elevated temperature provides the substituted phenylglycine derivatives. Another method is shown in pathway G. Glycine analogs can be derivatized with a variety of aryl halides in the presence of a source of palladium (0) such as palladium bis(tributylphosphine) and base such as potassium phosphate. The resultant ester can then be hydrolyzed by treatment with base or acid. It should be understood that other well known methods to prepare phenylglycine derivatives exist in the art and can be amended to provide the desired compounds in this description. It should also be understood that the final phenylglycine derivatives can be purified to enantiomeric purity greater than 98% ee via preparative HPLC.

Scheme 2: Acylated Amino Acid Derivatives

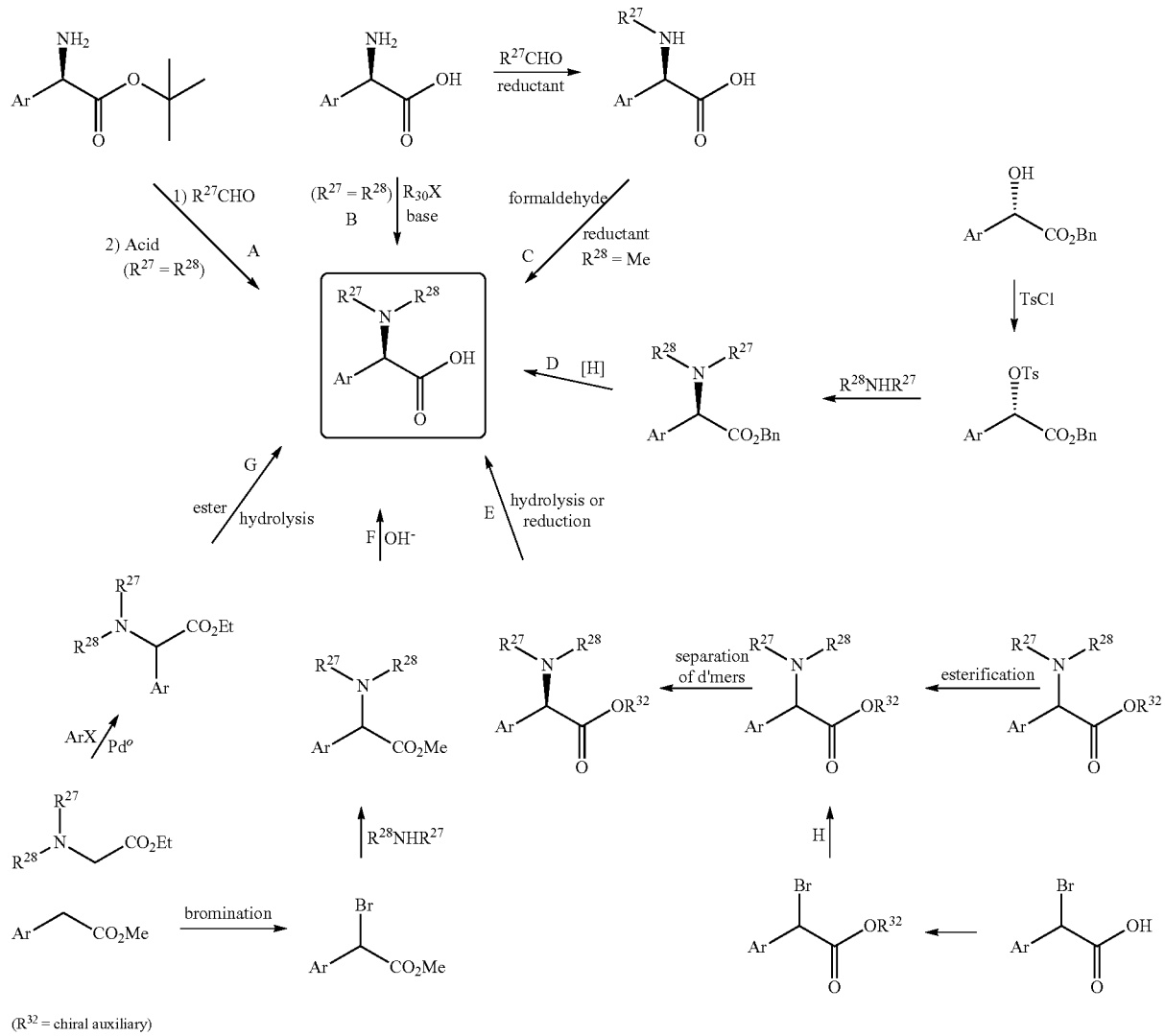

($R^{32}$ = chiral auxiliary)

In another embodiment of the present disclosure, acylated phenylglycine derivatives may be prepared as illustrated below. Phenylglycine derivatives wherein the carboxylic acid is protected as an easily removed ester, may be acylated with an acid chloride in the presence of a base such as triethylamine to provide the corresponding amides (pathway A). Pathway B illustrates the acylation of the starting phenylglycine derivative with an appropriate chloroformate while pathway C shows reaction with an appropriate isocyanate or carbamoyl chloride. Each of the three intermediates shown in pathways A-C may be deprotected by methods known by those skilled in the art (i.e.; treatment of the t-butyl ester with strong base such as HCl or trifluoroacetic acid).

retention times may vary slightly between machines. Additional LC conditions applicable to the current section, unless noted otherwise.
Condition MS-W1
Column=XTERRA® 3.0×50 mm S7
Start % B=0
Final % B=100
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$

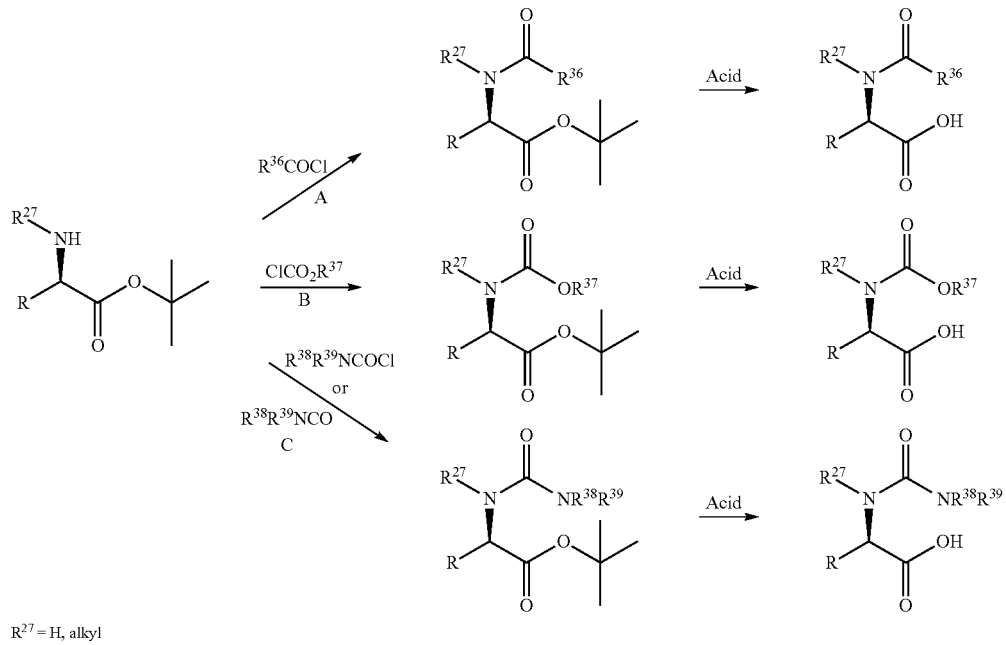

Scheme 3

$R^{27}$ = H, alkyl

Amino-substituted phenylacetic acids may be prepared by treatment of a chloromethylphenylacetic acid with an excess of an amine.

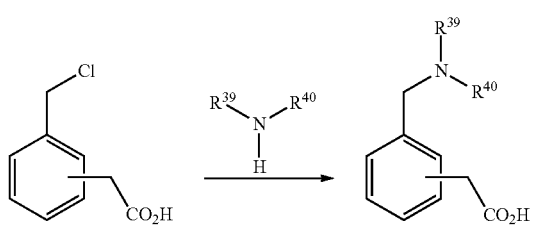

Synthesis of Common Caps

Compound Analysis Conditions

Purity assessment and low resolution mass analysis were conducted on a Shimadzu LC system coupled with Waters MICROMASS® ZQ MS system. It should be noted that Condition MS-W2
Column=XTERRA® 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition MS-W5
Column=XTERRA® 3.0×50 mm S7
Start % B=0
Final % B=30
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition D1
Column=XTERRA® C18 3.0×50 mm S7
Start % B=0
Final % B=100

Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition D2
Column=PHENOMENEX®-Luna 4.6×50 mm S10
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition M3
Column=XTERRA® C18 3.0×50 mm S7
Start % B=0
Final % B=40
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition I
Column=PHENOMENEX®-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition II
Column=PHENOMENEX®-Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition III
Column=XTERRA® C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$

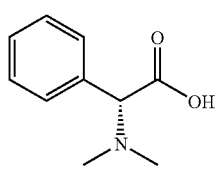

Cap-1

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to $H_2$ (60 psi) for 3 hours. The reaction mixture was filtered through diatomaceous earth (CELITE®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in $H_2O$; λ=589 nm]. $^1$H NMR (DMSO-$d_6$, δ=2.5 ppm, 500 MHz): δ 7.43-7.34 (m, 5H), 4.14 (s, 1H), 2.43 (s, 6H); LC (Cond. I): RT=0.25; LC/MS: Anal. Calcd. for $[M+H]^+$ $C_{10}H_{14}NO_2$ 180.10; found 180.17; HRMS: Anal. Calcd. for $[M+H]^+$ $C_{10}H_{14}NO_2$ 180.1025; found 180.1017.

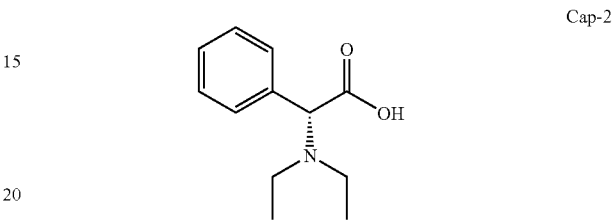

Cap-2

NaBH$_3$CN (6.22 g, 94 mmol) was added in portions over a few minutes to a cooled (ice/water) mixture of (R)-2-phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-$d_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: $[α]^{25}$-102.21° (c=0.357, $H_2O$); crop-2: $[α]^{25}$-99.7° (c=0.357, $H_2O$). LC (Cond. I): RT=0.43 min; LC/MS: Anal. Calcd. for $[M+H]^+$ $C_{12}H_{18}NO_2$: 208.13; found 208.26.

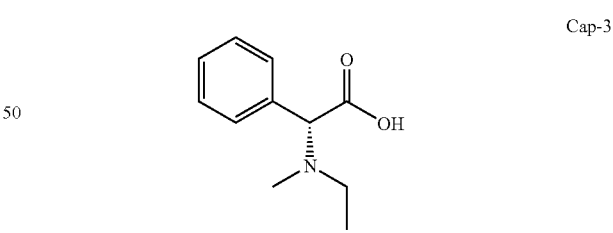

Cap-3

Acetaldehyde (5.0 mL, 89.1 mmol) and a suspension of 10% Pd/C (720 mg) in methanol/$H_2O$ (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of $H_2$ for 17 hours. An additional acetaldehyde (10 mL, 178.2 mmol) was added and stirring continued under $H_2$ atmosphere for 24 hours [Note: the supply of $H_2$ was replenished as needed throughout the reaction]. The reaction mixture was filtered through diatomaceous earth (CELITE®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-d$_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. I): RT=0.39 min; >95% homogeneity index; LC/MS: Anal. Calcd. for [M+H]$^+$ C$_{14}$H$_{14}$NO$_2$: 180.10; found 180.18.

A suspension of 10% Pd/C (536 mg) in methanol/H$_2$O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H$_2$ for ~72 hours, where the H$_2$ supply was replenished as needed. The reaction mixture was filtered through diatomaceous earth (CELITE®) and the filtrate was concentrated in vacuo. The resulting crude material was recrystallized from isopropanol (50 mL) to provide the HCl salt of Cap-3 as a white solid (985 mg). $^1$H NMR (DMSO-d$_6$, δ=2.5 ppm, 400 MHz): δ 10.48 (br 5, 1H), 7.59-7.51 (m, 5H), 5.26 (s, 1H), 3.08 (app br s, 2H), 2.65 (br s, 3H), 1.24 (br m, 3H). LC (Cond. I): RT=0.39 min; >95% homogeneity index; LC/MS: Anal. Calcd. for [M+H]$^+$ C$_{11}$H$_{16}$NO$_2$: 194.12; found 194.18; HRMS: Anal. Calcd. for [M+H]$^+$ C$_{11}$H$_6$NO$_2$: 194.1180; found 194.1181.

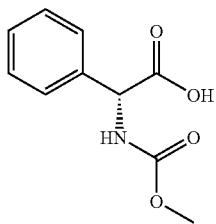

Cap-4

ClCO$_2$Me (3.2 mL, 41.4 mmol) was added dropwise to a cooled (ice/water) THF (410 mL) semi-solution of (R)-tent-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO$_3$ solution (30 mL), dried (MgSO$_4$), filtered, and concentrated in vacuo. The resultant colorless oil was triturated from hexanes, filtered and washed with hexanes (100 mL) to provide (R)-tent-butyl 2-(methoxycarbonylamino)-2-phenylacetate as a white solid (7.7 g). $^1$H NMR (DMSO-d$_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. I): RT=1.53 min; ~90% homogeneity index; LC/MS: Anal. Calcd. for [M+Na]$^+$ C$_{14}$H$_{19}$NNaO$_4$: 288.12; found 288.15.

TFA (16 mL) was added dropwise to a cooled (ice/water) CH$_2$Cl$_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: -176.9° [c=3.7 mg/mL in H$_2$O; λ=589 nm]. $^1$H NMR (DMSO-d$_6$, δ=2.5 ppm, 400 MHz): δ 12.84 (br 5, 1H), 7.96 (d, J=8.3, 1H), 7.41-7.29 (m, 5H), 5.14 (d, J=8.3, 1H), 3.55 (s, 3H). LC (Cond. I): RT=1.01 min; >95% homo-geneity index; LC/MS: Anal. Calcd. for [M+H]$^+$ C$_{10}$H$_{12}$NO$_4$ 210.08; found 210.17; HRMS: Anal. Calcd. for [M+H]$^+$ C$_{10}$H$_{12}$NO$_4$ 210.0766; found 210.0756.

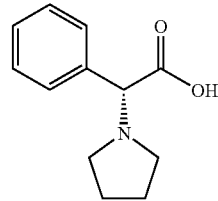

Cap-5

A mixture of (R)-2-phenylglycine (1.0 g, 6.62 mmol), 1,4-dibromobutane (1.57 g, 7.27 mmol) and Na$_2$CO$_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Cond. I); >98% homogeneity index; LC/MS: Anal. Calcd. for [M+H]$^+$ C$_{12}$H$_{16}$NO$_2$: 206.12; found 206.25.

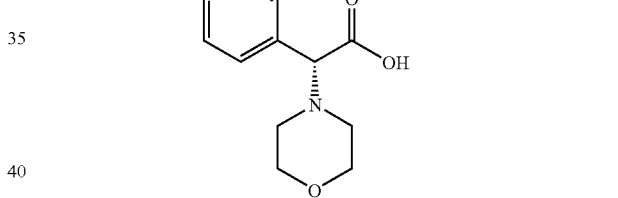

Cap-6

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Cond. I); >98%; LC/MS: Anal. Calcd. for [M+H]$^+$ C$_{12}$H$_{16}$NO$_3$: 222.11; found 222.20; HRMS: Anal. Calcd. for [M+H]$^+$ C$_{12}$H$_{16}$NO$_3$: 222.1130; found 222.1121.

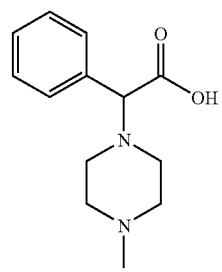

Cap-7

Cap-7a: enantiomer-1
Cap-7b: enantiomer-2

A CH₂Cl₂ (200 mL) solution of p-toluenesulfonyl chloride (8.65 g, 45.4 mmol) was added dropwise to a cooled (−5° C.) CH₂Cl₂ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO₄), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. ¹H NMR (DMSO-d₆, =2.5, 500 MHz) δ 7.78 (d, 8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]⁺ C₂₂H₂₀NaO₅S: 419.09; found 419.04.

A THF (75 mL) solution of benzyl 2-phenyl-2-(tosyloxy) acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO₄), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (CHIRALCEL® OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 µm) eluting with 85:15 Heptane/ethanol at 75 mL/min, and monitored at 220 nm. Enantiomer-1 (1.474 g) and enantiomer-2 (2.2149 g) were retrieved as viscous oil. ¹H NMR (CDCl₃, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]⁺ C₂₀H₂₅N₂O₂: 325.19; found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (CELITE®) and the filtrate was concentrated in vacuo to provide Cap-7, contaminated with phenylacetic acid as a tan foam (867.6 mg; mass is above the theoretical yield). The product was used for the next step without further purification. ¹H NMR (DMSO-d₆, 6=2.5, 500 MHz) δ 7.44-7.37 (m, 2H), 7.37-7.24 (m, 3H), 3.92 (s, 1H), 2.63-2.48 (app. br s, 2H), 2.48-2.32 (m, 6H), 2.19 (s, 3H); RT=0.31 (Cond. II); >90% homogeneity index; LC/MS: Anal. Calcd. for [M+H]⁺ C₁₃H₁₉N₂O₂: 235.14; found 235.15; HRMS: Anal. Calcd. for [M+H]⁺ C₁₃H₁₉N₂O₂: 235.1447; found 235.1440.

The synthesis of Cap-8 and Cap-9 was conducted according to the synthesis of Cap-7 by using appropriate amines for the SN₂ displacement step (i.e., 4-hydroxypiperidine for Cap-8 and (S)-3-fluoropyrrolidine for Cap-9) and modified conditions for the separation of the respective stereoisomeric intermediates, as described below.

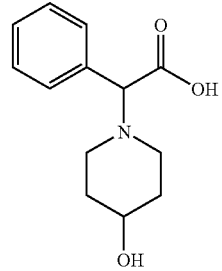

Cap-8

Cap-8a: enantiomer-1
Cap-8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 µm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: ¹H NMR (DMSO-d₆, 6=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. II); >98% homogeneity index; LC/MS: Anal. Calcd. for [M+H]⁺ C₁₃H₁₈NO₃: 236.13; found 236.07; HRMS: Calcd. for [M+H]⁺ C₁₃H₁₈NO₃: 236.1287; found 236.1283.

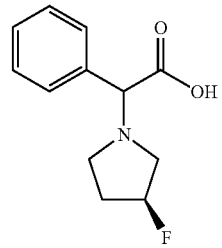

Cap-9

9a: diastereomer-1
9b: diastereomer-2

The diastereomeric separation of the intermediate benzyl 2-(S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 µm) eluting with 95% CO₂/5% methanol with 0.1% TFA, at 10 bar pressure, 70 mL/min flow rate, and a temperature of 35° C. The HPLC elute for the respective stereoisomers was concentrated, and the residue was dissolved in CH₂Cl₂ (20 mL) and washed with an aqueous medium (10 mL water+1 mL saturated NaHCO₃ solution). The organic phase was dried (MgSO₄), filtered, and concentrated in vacuo to provide 92.5 mg of fraction-1 and 59.6 mg of fraction-2. These benzyl esters were hydrogenolysed according to the preparation of Cap-7 to prepare Cap-9a and Cap-9b. Cap-9a (diastereomer-1; the sample is a TFA salt as a result of purification on a reverse phase HPLC using H₂O/ methanol/TFA solvent): $^1$H NMR (DMSO-d$_6$, δ=2.5, 400 MHz) 7.55-7.48 (m, 5H), 5.38 (d of m, 1H), 5.09 (br s, 1H), 3.84-2.82 (br m, 4H), 2.31-2.09 (m, 2H). RT=0.42 (Cond. I); >95% homogeneity index; LC/MS: Anal. Calcd. for [M+H]$^+$ C$_{12}$H$_{15}$FNO$_2$: 224.11; found 224.14; Cap-9b (diastereomer-2): $^1$H NMR (DMSO-d$_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]$^+$ C$_{12}$H$_{15}$FNO$_2$: 224.11; found 224.14.

Cap-10

To a solution of D-proline (2.0 g, 17 mmol) and formaldehyde (2.0 mL of 37% wt. in H$_2$O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (CELITE®) and concentrated in vacuo to provide Cap-10 as an off-white solid (2.15 g). $^1$H NMR (DMSO-d$_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]$^+$ C$_6$H$_{12}$NO$_2$: 130.09; found 129.96.

Cap-11

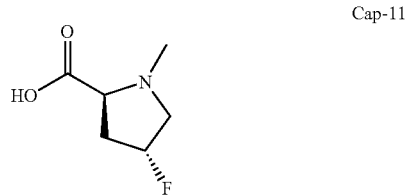

A mixture of (2S,4R)-4-fluoropyrrolidine-2-carboxylic acid (0.50 g, 3.8 mmol), formaldehyde (0.5 mL of 37% wt. in H$_2$O), 12 N HCl (0.25 mL) and 10% Pd/C (50 mg) in methanol (20 mL) was stirred under a balloon of hydrogen for 19 hours. The reaction mixture was filtered through diatomaceous earth (CELITE®) and the filtrate was concentrated in vacuo. The residue was recrystallized from isopropanol to provide the HCl salt of Cap-11 as a white solid (337.7 mg). $^1$H NMR (DMSO-d$_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. II); >98% homogeneity index; LC/MS: Anal. Calcd. for [M+H]$^+$ C$_6$H$_{11}$FNO$_2$: 148.08; found 148.06.

Cap-12 (same as Cap-52)

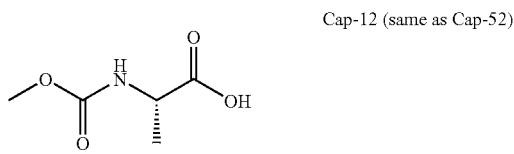

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH ~2-3. The resulting solutions was extracted with ethyl acetate (3×100 mL), and the combined organic phase was dried (Na$_2$SO$_4$), filtered, and concentrated in vacuo to provide a colorless oil (2.58 g). 500 mg of this material was purified by a reverse phase HPLC (H$_2$O/methanol/TFA) to provide 150 mg of Cap-12 as a colorless oil. $^1$H NMR (DMSO-d$_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

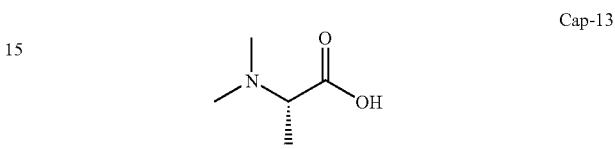

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (CELITE®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-d$_6$, δ=2.5, 500 MHz) δ 12.1 (br s, 1H), 4.06 (q, J=7.4, 1H), 2.76 (s, 6H), 1.46 (d, J=7.3, 3H).

Cap-14

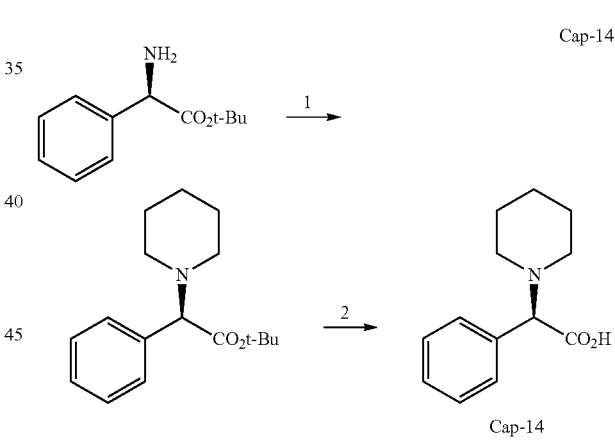

Step 1: A mixture of (R)-(–)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O—0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2

Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for $C_{17}H_{25}NO_2$: 275; found: 276 $(M+H)^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; $CH_3CN$—$H_2O$—0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-$d_6$) δ 7.50 (s, 5H), 5.13 (s, 1H), 109 (br s, 2H), 2.92-2.89 (m, 2H), 1.74 (m, 4H), 1.48 (br s, 2H). LC/MS: Anal. Calcd. for $C_{13}H_{17}NO_2$: 219; found: 220 $(M+H)^+$.

resulting solution was stirred at room temperature under Ar for 18 hours and then it was diluted with ethyl acetate, washed ($H_2O$×2, brine), dried ($Na_2SO_4$), filtered, and concentrated to give a pale yellow oil. Flash chromatography ($SiO_2$/hexane-ethyl acetate, 4:1) of this oil provided the title compound (11.64 g, 73%) as a white solid. $^1$H NMR (400 MHz, $CDCl_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl (R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed ($H_2O$×2, brine), dried ($MgSO_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R) -isomer: $^1$H NMR ($CD_3OD$) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for $C_{22}H_{27}NO_3$: 353; found: 354 $(M+H)^+$. (S,S)-isomer: $^1$H NMR ($CD_3OD$) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for $C_{22}H_{27}NO_3$: 353; found: 354 $(M+H)^+$.

Step 3: (R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$—0.1% TFA) to give the title compound (as TFA salt) as a pale bluish solid (0.128 g, 98%). LCMS: Anal. Calcd. for $C_{14}H_{19}NO_3$: 249; found: 250 $(M+H)^+$.

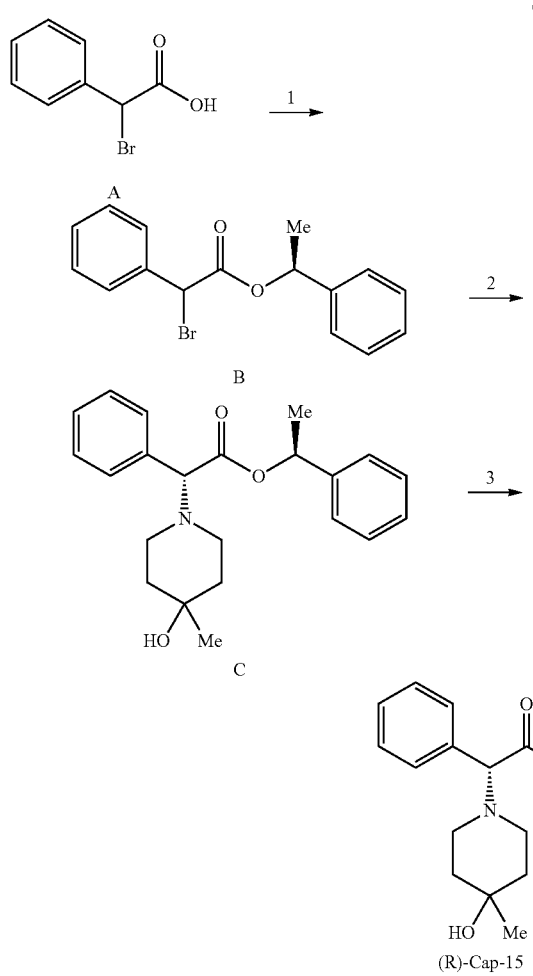

Cap-15

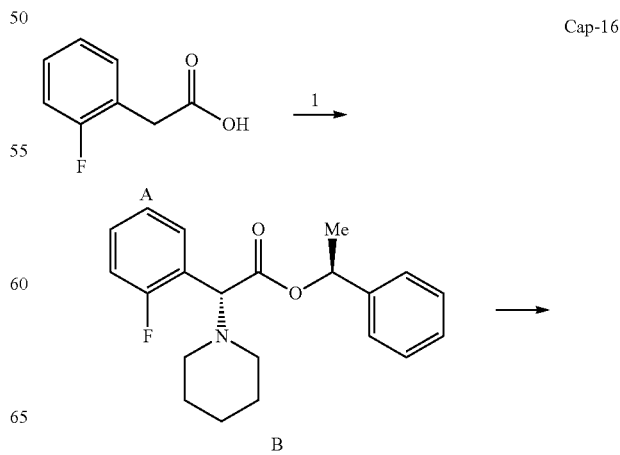

Cap-16

Step 1: (S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The

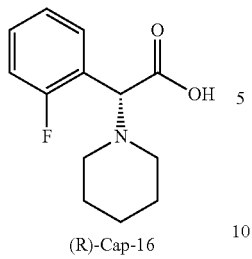

(R)-Cap-16

Step 1: (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in $CH_2Cl_2$ (100 mL) was stirred at room temperature for 12 hours. The solvent was then concentrated and the residue partitioned with $H_2O$-ethyl acetate. The phases were separated and the aqueous layer back-extracted with ethyl acetate (2×). The combined organic phases were washed ($H_2O$, brine), dried ($Na_2SO_4$), filtered, and concentrated in vacuo. The residue was purified by silica gel chromatography (BIOTAGE®/0-20% ethyl acetate-hexane) to provide the title compound as a colorless oil (8.38 g, 92%). $^1$H NMR (400 MHz, $CD_3OD$) δ 7.32-7.23 (m, 7H), 7.10-7.04 (m, 2), 5.85 (q, 1=6.5 Hz, 1H), 3.71 (s, 2H), 1.48 (d, Hz, 3H).

Step 2: (R)—((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of $CBr_4$ (13.5 g, 40.7 mmol) in THF (100 mL) was added and the mixture was allowed to warm to −10° C. and stirred at this temperature for 2 hours. The reaction mixture was quenched with saturated aq. $NH_4Cl$ and the layers were separated. The aqueous layer was back-extracted with ethyl acetate (2×) and the combined organic phases were washed ($H_2O$, brine), dried ($Na_2SO_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (BIOTAGE®/0-30% diethyl ether-hexane) to provide a pure mixture of diastereomers (2:1 ratio by $^1$H NMR) as a yellow oil (2.07 g, 31%), along with unreacted starting material (2.53 g, 51%). Further chromatography of the diastereomeric mixture (BIOTAGE®/0-10% diethyl ether-toluene) provided the title compound as a colorless oil (0.737 g, 11%). $^1$H NMR (400 MHz, $CD_3OD$) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for $C_{21}H_{24}FNO_2$: 341; found: 342 $(M+H)^+$.

Step 3: (R)-2-(2-Fluorophenyl)-2-(piperidin-1-yl)acetic acid: A mixture of (R)—((S)-1-phenylethyl) 2-(2-fluorophenyl)-2-(piperidin-1-yl)acetate (0.737 g, 2.16 mmol) and 20% $Pd(OH)_2$/C (0.070 g) in ethanol (30 mL) was hydrogenated at room temperature and atmospheric pressure ($H_2$ balloon) for 2 hours. The solution was then purged with Ar, filtered through diatomaceous earth (CELITE®), and concentrated in vacuo. This provided the title compound as a colorless solid (0.503 g, 98%). $^1$H NMR (400 MHz, $CD_3OD$) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for $C_{13}H_{16}FNO_2$: 237; found: 238 $(M+H)^+$.

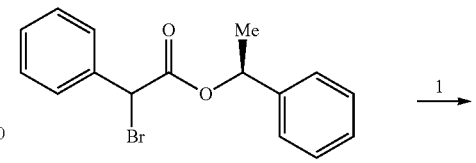

Cap-17

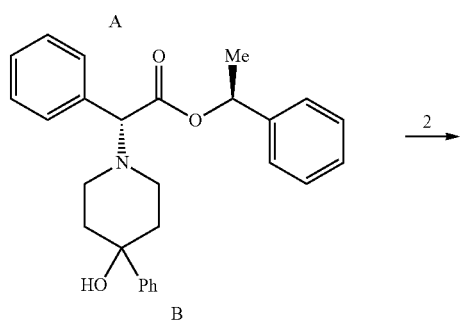

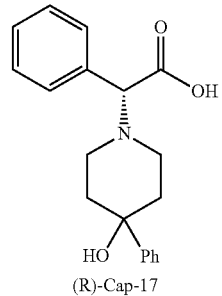

(R)-Cap-17

Step 1: (S)-1-Phenylethyl (R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O×2$, brine), dried ($MgSO_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (CHIRALCEL® OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415; found: 416 $(M+H)^+$; (S,S)-isomer: $^1$H NMR (400 MHz, $CD_3OD$) 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415; found: 416 $(M+H)^+$.

The following esters were prepared in similar fashion:

| Compound | Structure | Analytical Data |
|---|---|---|
| Intermediate-17a | 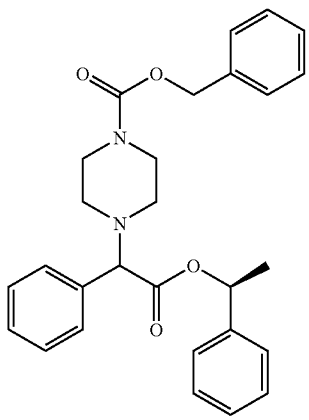 | Diastereomer 1: $^1$H NMR (500 MHz, DMSO-d$_6$) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LCMS: Anal. Calcd. for: C$_{28}$H$_{30}$N$_2$O$_4$ 458.22; Found: 459.44 (M + H)$^+$. Diastereomer 2: $^1$H NMR (500 MHz, DMSO-d$_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H). LCMS: Anal. Calcd. for: C$_{28}$H$_{30}$N$_2$O$_4$ 458.22; Found: 459.44 (M + H)$^+$. |
| Intermediate-17b | 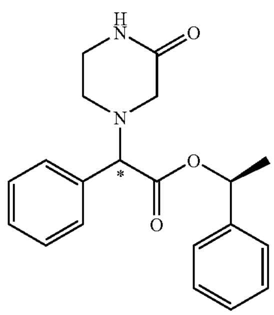 | Diastereomer 1: RT = 11.76 minutes (Cond. II); LCMS: Anal. Calcd. for: C$_{20}$H$_{22}$N$_2$O$_3$ 338.16 Found: 339.39 (M + H)$^+$; Diastereomer 2: RT = 10.05 minutes (Cond. II); LCMS: Anal. Calcd. for: C$_{20}$H$_{22}$N$_2$O$_3$ 338.16; Found: 339.39 (M + H)$^+$. |
| Intermediate-17c | 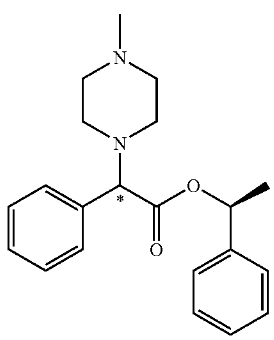 | Diastereomer 1: T$_R$ = 4.55 minutes (Cond. I); LCMS: Anal. Calcd. for: C$_{21}$H$_{26}$N$_2$O$_2$ 338.20 Found: 339.45 (M + H)$^+$; Diastereomer 2: T$_R$ = 6.00 minutes (Cond. I); LCMS: Anal. Calcd. for: C$_{21}$H$_{26}$N$_2$O$_2$ 338.20 Found: 339.45 (M + H)$^+$. |
| Intermediate-17d | | Diastereomer 1: RT = 7.19 minutes (Cond. I); LCMS: Anal. Calcd. for: C$_{27}$H$_{29}$NO$_2$ 399.22 Found: 400.48 (M + H)$^+$; Diastereomer 2: RT = 9.76 minutes (Cond. I); LCMS: Anal. Calcd. for: C$_{27}$H$_{29}$NO$_2$ 399.22 Found: 400.48 (M + H)$^+$. |

Chiral SFC Conditions for Determining Retention Time

Condition I
Column: Chiralpak AD-H Column, 4.62×50 mm, 5 μm
Solvents: 90% $CO_2$—10% methanol with 0.1% DEA
Temp: 35° C.
Pressure: 150 bar
Flow rate: 2.0 mL/min.
UV monitored @ 220 nm
Injection: 1.0 mg/3 mL methanol

Condition II
Column: CHIRALCEL® OD-H Column, 4.62×50 mm, 5 μm
Solvents: 90% $CO_2$—10% methanol with 0.1% DEA
Temp: 35° C.
Pressure: 150 bar
Flow rate: 2.0 mL/min.
UV monitored @ 220 nm
Injection: 1.0 mg/mL methanol Cap-17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$—0.1% TFA) to give the title compound (as TFA salt) as a white solid (0.230 g, 88%). LCMS: Anal. Calcd. for $C_{19}H_{21}NO_3$: 311.15; found: 312 (M+H)$^+$.

Cap-17a to Cap-17-d

The following carboxylic acids were prepared in optically pure form in a similar fashion:

| Cap | Structure | Data |
|---|---|---|
| Cap-17a | 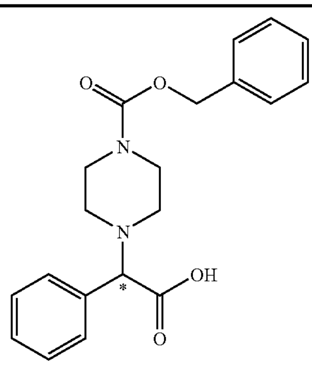 | RT = 2.21 (Cond. II); $^1$H NMR (500 MHz, DMSO-$d_6$) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 (M + H)$^+$. |
| Cap-17b | 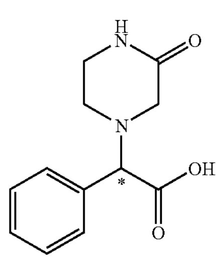 | RT = 0.27 (Cond. III); LCMS: Anal. Calcd. for: $C_{12}H_{14}N_2O_3$ 234.10; Found: 235.22 (M + H)$^+$. |
| Cap-17c | | RT = 0.48 (Cond. II); LCMS: Anal. Calcd. for: $C_{13}H_{18}N_2O_2$ 234.14; Found: 235.31 (M + H)$^+$. |
| Cap-17d | | RT = 2.21 (Cond. I); LCMS: Anal. Calcd. for: $C_{19}H_{21}NO_2$ 295.16; Found: 296.33 (M + H)$^+$. |

LCMS Conditions for Determining Retention Time

Condition I
Column: PHENOMENEX®-Luna 4.6×50 mm. S10
Start % B=0
Final % B=100
Gradient Time=4 min
Flow Rate=4 mL/min
Wavelength=220
Solvent A=10% methanol—90% $H_2O$—0.1% TFA
Solvent B=90% methanol—10% $H_2O$—0.1% TFA

Condition II
Column: Waters-Sunfire 4.6×50 mm S5
Start % B=0
Final % B=100
Gradient Time=2 min.
Flow Rate=4 mL/min
Wavelength=220
Solvent A=10% methanol—90% $H_2O$—0.1% TFA
Solvent B=90% methanol—10% $H_2O$—0.1% TFA

Condition III
Column: PHENOMENEX® 10μ, 3.0×50 mm
Start % B=0
Final % B=100
Gradient Time=2 min
Flow Rate=4 mL/min
Wavelength=220
Solvent A=10% methanol—90% $H_2O$—0.1% TFA
Solvent B=90% methanol—10% $H_2O$—0.1% TFA Cap-18

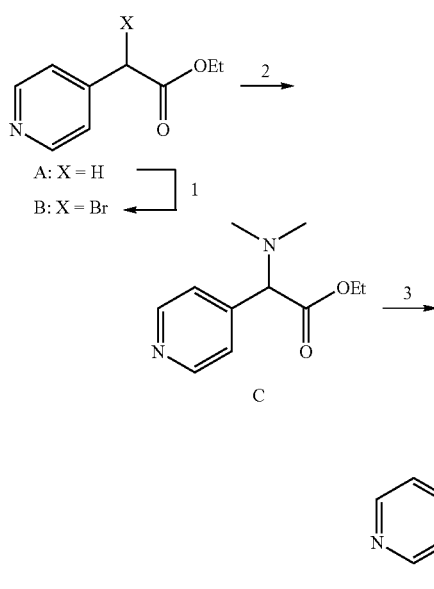

Step 1: (R,S)-Ethyl 2-(4-pyridyl)-2-bromoacetate

To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr$_4$ (2.21 g, 6.66 mmol) and stirring was continued at −78° C. for 2 hours. The reaction mixture was then quenched with sat. aq. NH$_4$Cl and the phases were separated. The organic phase was washed (brine), dried (Na$_2$SO$_4$), filtered, and concentrated in vacuo. The resulting yellow oil was immediately purified by flash chromatography (SiO$_2$/hexane-ethyl acetate, 1:1) to provide the title compound (1.40 g, 95%) as a somewhat unstable yellow oil. $^1$H NMR (400 MHz, CDCl$_3$) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for C$_9$H$_{10}$BrNO$_2$: 242, 244; found: 243, 245 (M+H).

Step 2: (R,S)-Ethyl 2-(4-pyridyl)-2-(N,N-dimethylamino)acetate

To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (BIOTAGE®, 40+M SiO$_2$ column; 50%-100% ethyl acetate-hexane) to provide the title compound (0.539 g, 31%) as a light yellow oil. $^1$H NMR (400 MHz, CDCl$_3$) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for C$_{11}$H$_{16}$N$_2$O$_2$: 208; found: 209 (M+H)$^+$.

Step 3: (R,S)-2-(4-Pyridyl)-2-(N,N-dimethylamino) acetic Acid

To a solution of (R,S)-ethyl 2-(4-pyridyl)-2-(N,N-dimethylamino)acetate (0.200 g, 0.960 mmol) in a mixture of THF-methanol-H$_2$O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$H NMR (400 MHz, DMSO-d$_6$) 8.49 (d, J=5.7 Hz, 2H), 7.34 (d, J=5.7 Hz, 2H), 3.56 (s, 1H), 2.21 (s, 6H).

Cap-19 to Cap-36

The following examples were prepared in similar fashion using the method described above:

| Cap | Structure | Data |
|---|---|---|
| Cap-19 | 3-pyridyl-CH(NMe$_2$)-CO$_2$H | LCMS: Anal. Calcd. for C$_9$H$_{12}$N$_2$O$_2$: 180; found: 181 (M + H)$^+$. |
| Cap-20 | 2-pyridyl-CH(NMe$_2$)-CO$_2$H | LCMS: no ionization. $^1$H NMR (400 MHz, CD$_3$OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |
| Cap-21 | 6-chloro-3-pyridyl-CH(NMe$_2$)-CO$_2$H | LCMS: Anal. Calcd. for C$_9$H$_{11}$ClN$_2$O$_2$: 214, 216; found: 215, 217 (M + H)$^+$. |
| Cap-22 | 4-nitrophenyl-CH(NMe$_2$)-CO$_2$H | LCMS: Anal. Calcd. for C$_{10}$H$_{12}$N$_2$O$_4$: 224; found: 225 (M + H)$^+$. |
| Cap-23 | 1-naphthyl-CH(NMe$_2$)-CO$_2$H | LCMS: Anal. Calcd. for C$_{14}$H$_{15}$NO$_2$: 229; found: 230 (M + H)$^+$. |
| Cap-24 | 3-(trifluoromethyl)phenyl-CH(NMe$_2$)-CO$_2$H | LCMS: Anal. Calcd. for C$_{11}$H$_{12}$F$_3$NO$_2$: 247; found: 248 (M + H)$^+$. |
| Cap-25 | 2-(trifluoromethyl)phenyl-CH(NMe$_2$)-CO$_2$H | LCMS: Anal. Calcd. for C$_{11}$H$_{12}$F$_3$NO$_2$: 247; found: 248 (M + H)$^+$. |

-continued

| Cap | Structure | Data |
|---|---|---|
| Cap-26 | (2-fluorophenyl, NMe2, CO2H) | LCMS: Anal. Calcd. for $C_{10}H_{12}FNO_2$: 197; found: 198 (M + H)$^+$. |
| Cap-27 | (3-fluorophenyl, NMe2, CO2H) | LCMS: Anal. Calcd. for $C_{10}H_{12}FNO_2$: 247; found: 248 (M + H)$^+$. |
| Cap-28 | (3-chlorophenyl, NMe2, CO2H) | LCMS: Anal. Calcd. for $C_{10}H_{12}ClNO_2$: 213; found: 214 (M + H)$^+$. |
| Cap-29 | (2-chlorophenyl, NMe2, CO2H) | LCMS: Anal. Calcd. for $C_{10}H_{12}ClNO_2$: 213; found: 214 (M + H)$^+$. |
| Cap-30 | (4-chlorophenyl, NMe2, CO2H) | LCMS: Anal. Calcd. for $C_{10}H_{12}ClNO_2$: 213; found: 214 (M + H)$^+$. |
| Cap-31 | (2-methylthiazol-4-yl, NMe2, CO2H) | LCMS: Anal. Calcd. for $C_8H_{12}N_2O_2S$: 200; found: 201 (M + H)$^+$. |
| Cap-32 | (thiophen-2-yl, NMe2, CO2H) | LCMS: Anal. Calcd. for $C_8H_{11}NO_2S$: 185; found: 186 (M + H)$^+$. |
| Cap-33 | (thiophen-3-yl, NMe2, CO2H) | LCMS: Anal. Calcd. for $C_8H_{11}NO_2S$: 185; found: 186 (M + H)$^+$. |
| Cap-34 | (benzo[d]isoxazol-3-yl, NMe2, CO2H) | LCMS: Anal. Calcd. for $C_{11}H_{12}N_2O_3$: 220; found: 221 (M + H)$^+$. |
| Cap-35 | (benzothiophen-3-yl, NMe2, CO2H) | LCMS: Anal. Calcd. for $C_{12}H_{13}NO_2S$: 235; found: 236 (M + H)$^+$. |
| Cap-36 | (2-methylbenzothiazol-5-yl, NMe2, CO2H) | LCMS: Anal. Calcd. for $C_{12}H_{14}N_2O_2S$: 250; found: 251 (M + H)$^+$. |

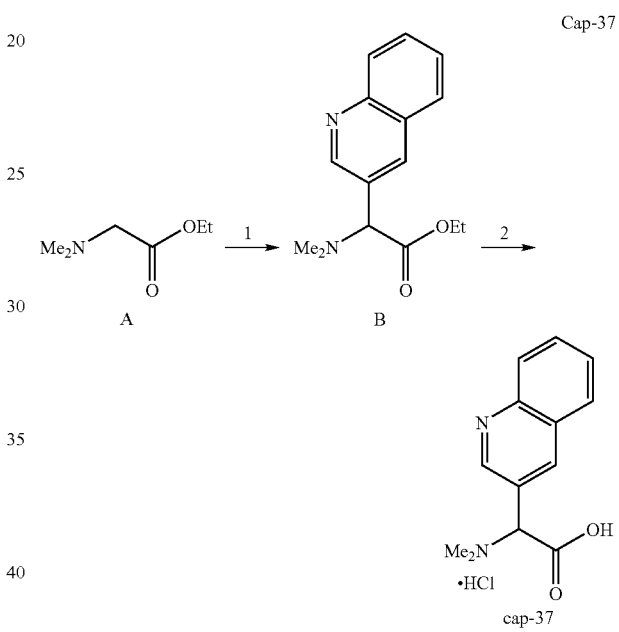

Cap-37

Step 1: (R,S)-Ethyl 2-(quinolin-3-yl)-2-(N,N-dimethylamino)-acetate

A mixture of ethyl N,N-dimethylaminoacetate (0.462 g, 3.54 mmol), $K_3PO_4$ (1.90 g, 8.95 mmol), Pd(t-Bu$_3$P)$_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1$H NMR (400 MHz, CDCl$_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258; found: 259 (M+H)$^+$.

Step 2: (R,S) 2-(Quinolin-3-yl)-2-(N,N-dimethylamino)acetic Acid

A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230; found: 231 (M+H)+.

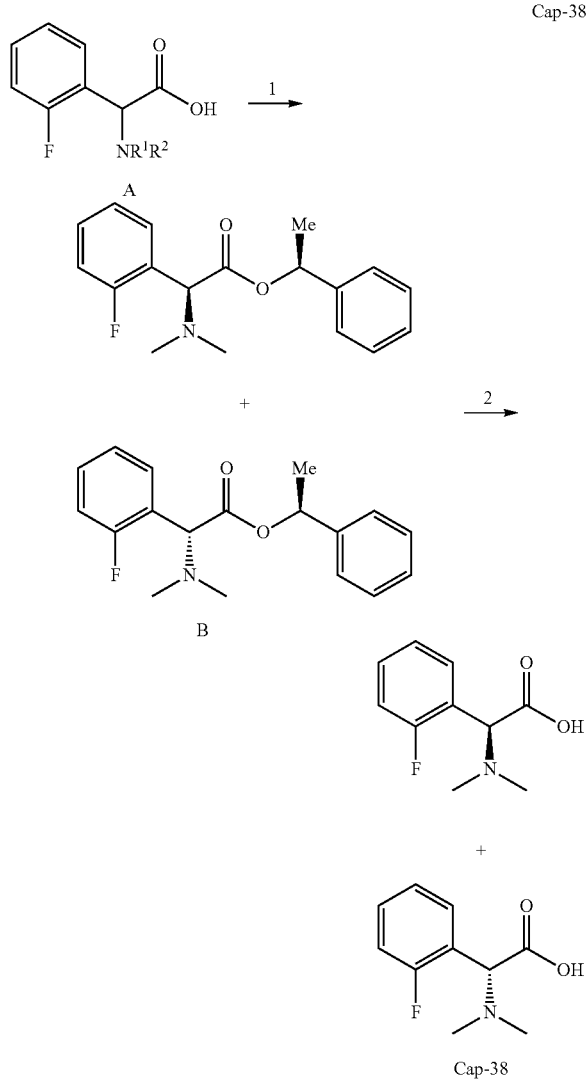

Cap-38

Step 1: (R)—((S)-1-Phenylethyl) 2-(dimethylamino)-2-(2-fluorophenyl)acetate and (S)—((S)-1-phenylethyl) 2-(dimethylamino)-2-(2-fluorophenyl)acetate To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (BIOTAGE®/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)-acetate (0.727 g, 18%), both as their TFA salts. (S,R)-isomer: $^1$H NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for $C_{18}H_{20}FNO_2$: 301; found: 302 (M+H)+; (S,S)-isomer: $^1$H NMR (400 MHz, $CD_3OD$) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for $C_{18}H_{20}FNO_2$: 301; found: 302 (M+H)+.

Step 2: (R)-2-(Dimethylamino)-2-(2-fluorophenyl) acetic Acid

A mixture of (R)—((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure (H$_2$ balloon) for 4 hours. The solution was then purged with Ar, filtered through diatomaceous earth (CELITE®), and concentrated in vacuo. This gave the title compound as a colorless solid (0.503 g, 98%). $^1$H NMR (400 MHz, $CD_3OD$) δ 7.53-7.63 (m, 2H), 7.33-7.38 (m, 2H), 5.36 (s, 1H), 2.86 (s, 6H). LCMS: Anal. Calcd. for $C_{10}H_{12}FNO_2$: 197; found: 198 (M+H)+.

The S-isomer could be obtained from (S)—((S)-1-phenylethyl) 2-(dimethylamino)-2-(2-fluorophenyl)acetate TFA salt in similar fashion.

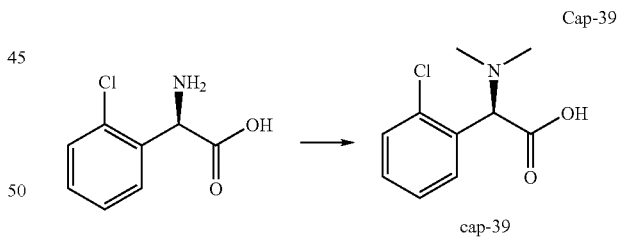

Cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure (H$_2$ balloon) for 4 hours. The solution was then purged with Ar, filtered through diatomaceous earth (CELITE®) and concentrated in vacuo. The residue was purified by reverse-phase preparative HPLC (Primesphere C-18, 30×100 mm; $CH_3CN$—$H_2O$—0.1% TFA) to give the TFA salt of the title compound (R)-2-(dimethylamino)-2-(2-chlorophenyl)acetic acid as a colorless oil (0.290 g, 55%). $^1$H NMR (400 MHz, $CD_3OD$) δ 7.59-7.65 (m, 2H), 7.45-7.53 (m, 2H), 5.40 (s, 1H), 2.87 (s, 6H). LCMS: Anal. Calcd. for $C_{10}H_{12}ClNO_2$: 213; found: 214 (M+H)+.

Cap-40

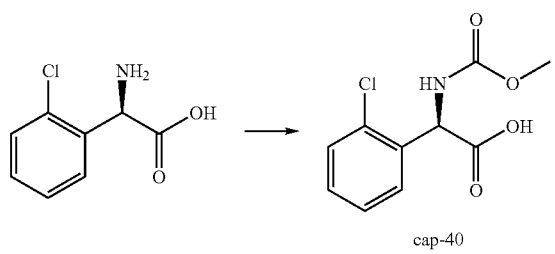

cap-40

To an ice-cold solution of (R)-(2-chlorophenyl)glycine (1.00 g, 5.38 mmol) and NaOH (0.862 g, 21.6 mmol) in $H_2O$ (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed ($H_2O$, brine), dried ($Na_2SO_4$), filtered, and concentrated in vacuo to give the title compound (R)-2-(methoxycarbonylamino)-2-(2-chlorophenyl)acetic acid as a yellow-orange foam (1.31 g, 96%). $^1H$ NMR (400 MHz, $CD_3OD$) δ 7.39-7.43 (m, 2H), 7.29-7.31 (m, 2H), 5.69 (s, 1H), 3.65 (s, 3H). LCMS: Anal. Calcd. for $C_{10}H_{10}ClNO_4$: 243; found: 244 $(M+H)^+$.

Cap-41

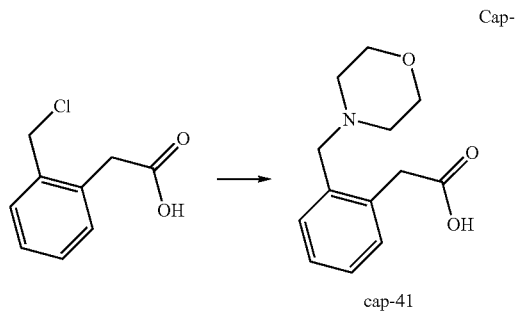

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with $H_2O$ (2×). The aqueous phase was lyophilized and the residue was purified by silica gel chromatography (BIOTAGE®/0-10% methanol-$CH_2Cl_2$) to give the title compound 2-(2-(Morpholinomethyl)phenyl)acetic acid as a colorless solid (2.22 g, 87%). $^1H$ NMR (400 MHz, $CD_3OD$) δ 7.37-7.44 (m, 3H), 7.29-7.33 (m, 1H), 4.24 (s, 2H), 183 (br s, 4H), 3.68 (s, 2H), 3.14 (br s, 4H). LCMS: Anal. Calcd. for $C_{13}H_{17}NO_3$: 235; found: 236 $(M+H)^+$.

Cap-42 to Cap-45

The following examples were similarly prepared using the method described for Cap-41:

| Cap | Structure | Data |
|---|---|---|
| Cap-42 | 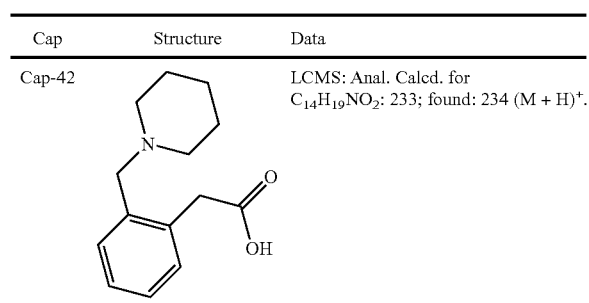 | LCMS: Anal. Calcd. for $C_{14}H_{19}NO_2$: 233; found: 234 $(M+H)^+$. |
| Cap-43 | (pyrrolidinylmethyl phenylacetic acid) | LCMS: Anal. Calcd. for $C_{13}H_{17}NO_2$: 219; found: 220 $(M+H)^+$. |
| Cap-44 | (N,N-dimethylaminomethyl phenylacetic acid) | LCMS: Anal. Calcd. for $C_{11}H_{15}NO_2$: 193; found: 194 $(M+H)^+$. |
| Cap-45 | (4-methylpiperazinylmethyl phenylacetic acid) | LCMS: Anal. Calcd. for $C_{14}H_{20}N_2O_2$: 248; found: 249 $(M+H)^+$. |

Cap-45a

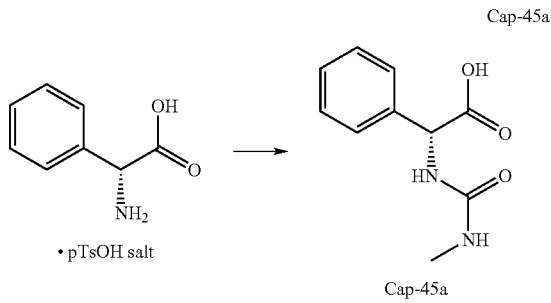

Cap-45a

HMDS (1.85 mL, 8.77 mmol) was added to a suspension of (R)-2-amino-2-phenylacetic acid p-toluenesulfonate (2.83 g, 8.77 mmol) in $CH_2Cl_2$ (10 mL) and the mixture was stirred at room temperature for 30 minutes. Methyl isocyanate (0.5 g, 8.77 mmol) was added in one portion stirring continued for 30 minutes. The reaction was quenched by addition of $H_2O$ (5 mL) and the resulting precipitate was filtered, washed with $H_2O$ and n-hexanes, and dried under vacuum. (R)-2-(3-methylureido)-2-phenylacetic acid (1.5 g; 82%) was recovered as a white solid and it was used without further purification. $^1H$ NMR (500 MHz, DMSO-$d_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for $C_{10}H_{12}N_2O_3$ 208.08 found 209.121 $(M+H)^+$; HPLC PHENOMENEX® C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

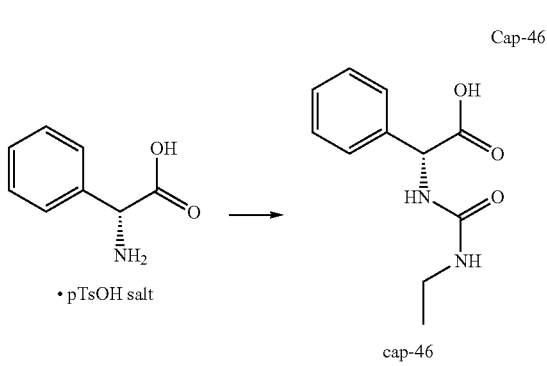

The desired product was prepared according to the method described for Cap-45a. ¹H NMR (500 MHz, DMSO-d₆) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for $C_{11}H_{14}N_2O_3$ 222.10 found 223.15 (M+H)⁺. HPLC XTERRA® C-18 3.0×506 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.87 min, 90% homogeneity index.

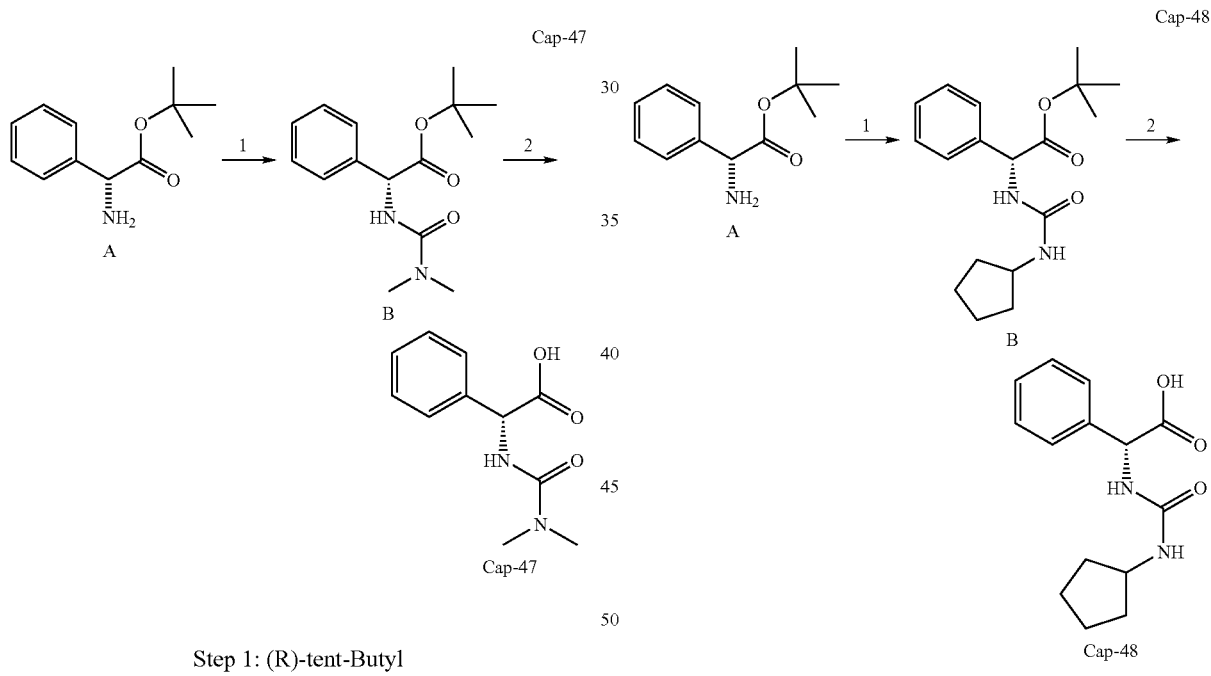

Step 1: (R)-tent-Butyl 2-(3,3-dimethylureido)-2-phenylacetate

To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H₂O, 1N aq. HCl and brine, dried (MgSO₄), filtered and concentrated under reduced pressure. (R)-tent-butyl 2-(3,3-dimethylureido)-2-phenylacetate was obtained as a white solid (0.86 g; 75%) and used without further purification. ¹H NMR (500 MHz, DMSO-d₆) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for $C_{15}H_{22}N_2O_3$ 278.16 found 279.23 (M+H)⁺; HPLC PHENOMENEX® LUNA C-18 4.6× 50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2: (R)-2-(3,3-Dimethylureido)-2-phenylacetic Acid

To a stirred solution of ((R)-tert-butyl 2-(3,3-dimethylureido)-2-phenylacetate (0.86 g, 3.10 mmol) in CH₂Cl₂ (250 mL) was added TPA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. ¹H NMR (500 MHz, DMSO-d₆) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24; found: 223.21 (MSH)⁺. HPLC XTERRA® C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.75 min, 93% homogeneity index.

Step 1: (R)-tort-Butyl 2-(3-cyclopentylureido)-2-phenylacetate

To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with H₂O and brine, dried (MgSO₄), filtered, and concentrated under reduced pressure. (R)-tent-butyl 2-(3-cyclopentylureido)-2-phenylacetate was obtained as an opaque oil (1.32 g; 100%) and used without further purification. ¹H NMR (500 MHz, CD$_3$Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for C$_{18}$H$_{26}$N$_2$O$_3$ 318.19 found 319.21 (M+H)$^+$; HPLC XTERRA® C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2: (R)-2-(3-Cyclopentylureido)-2-phenylacetic Acid

To a stirred solution of (R)-tent-butyl 2-(3-cyclopentylureido)-2-phenylacetate (1.31 g, 4.10 mmol) in CH$_2$Cl$_2$ (25 mL) was added TFA (4 mL) and triethylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-d$_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for C$_{14}$H$_{18}$N$_2$O$_3$: 262.31; found: 263.15 (M+H)$^+$. HPLC XTERRA® C-18 3.0×50 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=1.24 min, 100% homogeneity index.

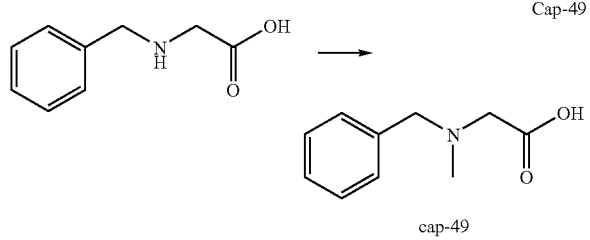

cap-49

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC(XTERRA® 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl(methyl)-amino)acetic acid as its TFA salt (723 mg, 33%) as a colorless wax. $^1$H NMR (300 MHz, DMSO-d$_6$) δ ppm 2.75 (s, 3H) 4.04 (s, 2H) 4.34 (s, 2H) 7.29-7.68 (m, 5H). LCMS: Anal. Calcd. for: C$_{10}$H$_{13}$NO$_2$ 179.09; Found: 180.20 (M+H)$^+$.

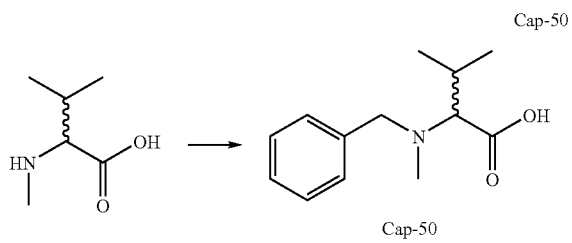

Cap-50

To a stirred solution of 3-methyl-2-(methylamino)butanoic acid (0.50 g, 3.81 mmol) in water (30 mL) was added K$_2$CO$_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (XTERRA® 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-d$_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: C$_{13}$H$_{19}$NO$_2$ 221.14; Found: 222.28 (M+H)$^+$.

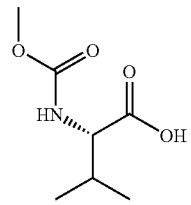

Cap-51

Na$_2$CO$_3$ (1.83 g, 17.2 mmol) was added to NaOH (33 mL of 1M/H$_2$O, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with CH$_2$Cl$_2$ (50 mL, 3×). The organic phase was dried (MgSO$_4$) and evaporated in vacuo to afford Cap-51 as a white solid (6 g). $^1$H NMR for the dominant rotamer (DMSO-d$_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ C$_7$H$_{14}$NO$_4$: 176.0923; found 176.0922.

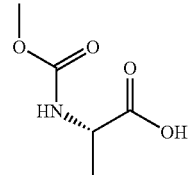

Cap-52 (same as Cap-12)

Cap-52 was synthesized from L-alanine according to the procedure described for the synthesis of Cap-51. For characterization purposes, a portion of the crude material was purified by a reverse phase HPLC (H$_2$O/methanol/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to Cap-64

Cap-53 to Cap-64 were prepared from appropriate starting materials according to the procedure described for the synthesis of Cap-51, with noted modifications if any.

| Cap | Structure | Data |
|---|---|---|
| Cap-53a: (R) Cap-53b: (S) | | $^1$H NMR (DMSO-d$_6$, δ = 2.5 ppm, 500 MHz): δ 12.51 (br s, 1 H), 7.4 (d, J = 7.9, 0.9 H), 7.06 (app s, 0.1 H), 3.86-3.82 (m, 1 H), 3.53 (s, 3 H), 1.75-1.67 (m, 1 H), 1.62-1.54 (m, 1 H), 0.88 (d, J= 7.3, 3 H). RT = 0.77 minutes (Cond. 2); LC/MS: Anal. Calcd. for [M + Na]$^+$ C$_6$H$_{11}$NNaO$_4$: 184.06; found 184.07. HRMS Calcd. for [M + Na]$^+$ C$_6$H$_{11}$NNaO$_4$: 184.0586; found 184.0592. |
| Cap-54a: (R) Cap-54b: (S) | | $^1$H NMR (DMSO-d$_6$, δ = 2.5 ppm, 500 MHz): δ 12.48 (s, 1 H), 7.58 (d, J = 7.6, 0.9 H), 7.25 (app s, 0.1 H), 3.52 (s, 3 H), 3.36-3.33 (m, 1 H), 1.10-1.01 (m, 1 H), 0.54-0.49 (m, 1 H), 0.46-0.40 (m, 1 H), 0.39-0.35 (m, 1 H), 0.31-0.21 (m, 1 H). HRMS Calcd. for [M + H]$^+$ C$_7$H$_{12}$NO$_4$: 174.0766; found 174.0771 |
| Cap-55 | 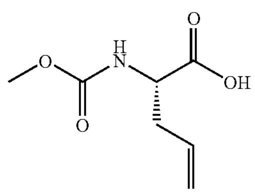 | $^1$H NMR (DMSO-d$_6$, δ = 2.5 ppm, 500 MHz): δ 12.62 (s, 1 H), 7.42 (d, J = 8.2, 0.9 H), 7.07 (app s, 0.1 H), 5.80-5.72 (m, 1 H), 5.10 (d, J = 17.1, 1 H), 5.04 (d, J = 10.4, 1 H), 4.01-3.96 (m, 1 H), 3.53 (s, 3 H), 2.47-2.42 (m, 1 H), 2.35-2.29 (m, 1 H). |
| Cap-56 | 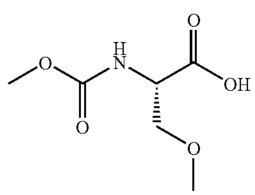 | $^1$H NMR (DMSO-d$_6$, δ = 2.5 ppm, 500 MHz): δ 12.75 (s, 1 H), 7.38 (d, J = 8.3, 0.9 H), 6.96 (app s, 0.1 H), 4.20-4.16 (m, 1 H), 3.60-3.55 (m, 2 H), 3.54 (s, 3 H), 3.24 (s, 3 H). |
| Cap-57 | 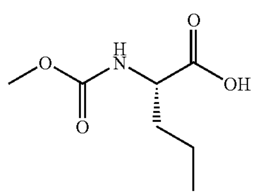 | $^1$H NMR (DMSO-d$_6$, δ = 2.5 ppm, 500 MHz): δ 12.50 (s, 1 H), 8.02 (d, J = 7.7, 0.08 H), 7.40 (d, J = 7.9, 0.76 H), 7.19 (d, J = 8.2, 0.07 H), 7.07 (d, J = 6.7, 0.09 H), 4.21-4.12 (m, 0.08 H), 4.06-3.97 (m, 0.07 H), 3.96-3.80 (m, 0.85 H), 3.53 (s, 3 H), 1.69-1.51 (m, 2 H), 1.39-1.26 (m, 2 H), 0.85 (t, J = 7.4, 3 H). LC (Cond. 2): RT = 1.39 LC/MS: Anal. Calcd. for [M + H]$^+$ C$_7$H$_{14}$NO$_4$: 176.09; found 176.06. |
| Cap-58 | 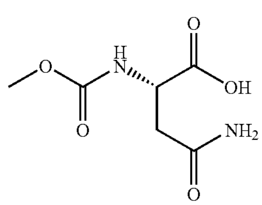 | $^1$H NMR (DMSO-d$_6$, δ = 2.5 ppm, 500 MHz): δ 12.63 (br s, 1 H), 7.35 (s, 1 H), 7.31 (d, J = 8.2, 1 H), 6.92 (s, 1 H), 4.33-4.29 (m, 1 H), 3.54 (s, 3 H), 2.54 (dd, J = 15.5, 5.4, 1 H), 2.43 (dd, J = 15.6, 8.0, 1 H). RT = 0.16 min (Cond. 2); LC/MS: Anal. Calcd. for [M + H]$^+$ C$_6$H$_{11}$N$_2$O$_5$: 191.07; found 191.14. |
| Cap-59a: (R) Cap-59b: (S) | | $^1$H NMR (DMSO-d$_6$, δ = 2.5 ppm, 400 MHz): δ 12.49 (br s, 1 H), 7.40 (d, J = 7.3, 0.89 H), 7.04 (br s, 0.1 H), 4.00-3.95 (m, 3 H), 1.24 (d, J = 7.3, 3 H), 1.15 (t, J = 7.2, 3 H). HRMS: Anal. Calcd. for [M + H]$^+$ C$_6$H$_{12}$NO$_4$: 162.0766; found 162.0771. |
| Cap-60 | 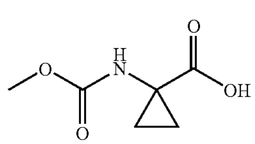 | The crude material was purified with a reverse phase HPLC (H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1 H), 7.74 (s, 0.82 H), 7.48 (s, 0.18 H), 3.54/3.51 (two s, 3 H), 1.30 (m, 2 H), 0.98 (m, 2 H). HRMS: Anal. Calcd. for [M + H]$^+$ C$_6$H$_{10}$NO$_4$: 160.0610; found 160.0604. |

| Cap | Structure | Data |
|---|---|---|
| Cap-61 | 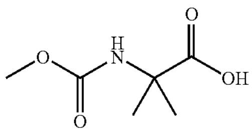 | ¹H NMR (DMSO-d₆, δ = 2.5 ppm, 400 MHz): δ 12.27 (br s, 1 H), 7.40 (br s, 1 H), 3.50 (s, 3 H), 1.32 (s, 6 H). HRMS: Anal. Calcd. for [M + H]⁺ C₆H₁₂NO₄: 162.0766; found 162.0765. |
| Cap-62 | 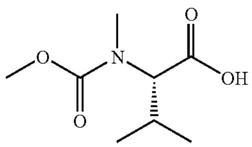 | ¹H NMR (DMSO-d₆, δ = 2.5 ppm, 400 MHz): δ 12.74 (br s, 1 H), 4.21 (d, J = 10.3, 0.6 H), 4.05 (d, J = 10.0, 0.4 H), 3.62/3.60 (two singlets, 3 H), 3.0 (s, 3 H), 2.14-2.05 (m, 1 H), 0.95 (d, J = 6.3, 3 H), 0.81 (d, J = 6.6, 3 H). LC/MS: Anal. Calcd. for [M − H]⁻ C₈H₁₄NO₄: 188.09; found 188.05. |
| Cap-63 | 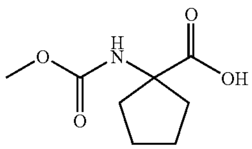 | [Note: the reaction was allowed to run for longer than what was noted for the general procedure.] ¹H NMR (DMSO-d₆, δ = 2.5 ppm, 400 MHz): 12.21 (br s, 1 H), 7.42 (br s, 1 H), 3.50 (s, 3 H), 2.02-1.85 (m, 4 H), 1.66-1.58 (m, 4 H). LC/MS: Anal. Calcd. for [M + H]⁺ C₈H₁₄NO₄: 188.09; found 188.19. |
| Cap-64 | 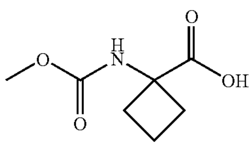 | [Note: the reaction was allowed to run for longer than what was noted for the general procedure.] ¹H NMR (DMSO-d₆, δ = 2.5 ppm, 400 MHz): 12.35 (br s, 1 H), 7.77 (s, 0.82 H), 7.56/7.52 (overlapping br s, 0.18 H), 3.50 (s, 3 H), 2.47-2.40 (m, 2 H), 2.14-2.07 (m, 2 H), 1.93-1.82 (m, 2 H). |

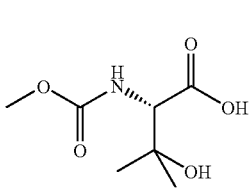

Cap-65

Methyl chloroformate (0.65 mL, 8.39 mmol) was added dropwise over 5 min to a cooled (ice-water) mixture of Na₂CO₃ (0.449 g, 4.23 mmol), NaOH (8.2 mL of 1M/H₂O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH₂Cl₂, and the aqueous phase was cooled with ice-water bath and acidified with concentrated HCl to a pH region of 1-2. The volatile component was removed in vacuo and the residue was taken up in a 2:1 mixture of MeOH/CH₂Cl₂ (15 mL) and filtered, and the filterate was rotervaped to afford Cap-65 as a white semi-viscous foam (1.236 g). ¹H NMR (DMSO-d₆, δ=2.5 ppm, 400 MHz): δ 6.94 (d, J=8.5, 0.9H), 6.53 (br s, 0.1H), 3.89 (d, J=8.8, 1H), 2.94 (s, 3H), 115 (s, 3H), 1.13 (s, 3H).

Cap-66 and Cap-67 were prepared from appropriate commercially available starting materials by employing the procedure described for the synthesis of Cap-65.

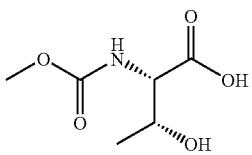

Cap-66

¹H NMR (DMSO-d₆, δ 2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

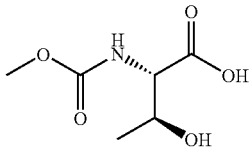

Cap-67

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

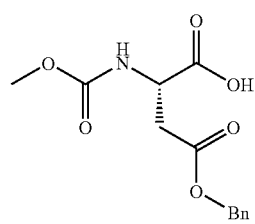

Cap-68

Methyl chloroformate (0.38 ml, 4.9 mmol) was added drop-wise to a mixture of 1N NaOH (aq) (9.0 ml, 9.0 mmol), 1M NaHCO₃ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH~1-2, and extracted with ethyl acetate (3×50 ml). The combined organic layers were washed with brine, dried (Na₂SO₄), filtered, and concentrated in vacuo to afford Cap-68 as a light yellow oil (1.37 g; mass is above theoretical yield, and the product was used without further purification). ¹H NMR (DMSO-$d_6$, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]⁺ $C_{13}H_{16}NO_6$: 282.10; found 282.12.

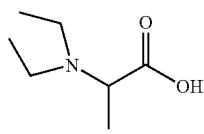

Cap-69a and Cap-69b

Cap-69a: (R)-enantiomer
Cap-69b: (S)-enantiomer

NaCNBH₃ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a DOWEX® 50WX8-100 ion-exchange resin (column was washed with water, and the compound was eluted with dilute NH₄OH, prepared by mixing 18 ml of NH₄OH and 282 ml of water) to afford Cap-69 (2.0 g) as an off-white soft hygroscopic solid. ¹H NMR (DMSO-$d_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to Cap-74x

Cap-70 to Cap-74x were prepared according to the procedure described for the synthesis of Cap-69 by employing appropriate starting materials.

| Cap | Structure | Data |
|---|---|---|
| Cap-70a: (R) Cap-70b: (S) | | ¹H NMR (DMSO-$d_6$, δ = 2.5 ppm, 400 MHz): δ 3.42 (q, J = 7.1, 1 H), 2.68-2.60 (m, 4 H), 1.53-1.44 (m, 4 H), 1.19 (d, J = 7.3, 3 H), 0.85 (t, J = 7.5, 6 H). LC/MS: Anal. Calcd. for [M + H]⁺ $C_9H_{20}NO_2$: 174.15; found 174.13. |
| Cap-71a: (R) Cap-71b: (S) | | ¹H NMR (DMSO-$d_6$, δ = 2.5 ppm, 500 MHz): δ 3.18-3.14 (m, 1 H), 2.84-2.77 (m, 2 H), 2.76-2.68 (m, 2 H), 1.69-1.54 (m, 2 H), 1.05 (t, J = 7.2, 6 H), 0.91 (t, J = 7.3, 3 H). LC/MS: Anal. Calcd. for [M + H]⁺ $C_8H_{18}NO_2$: 160.13; found 160.06. |
| Cap-72 | 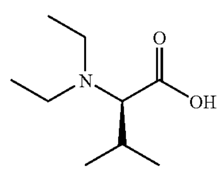 | ¹H NMR (DMSO-$d_6$, δ = 2.5 ppm, 400 MHz): δ 2.77-2.66 (m, 3 H), 2.39-2.31 (m, 2 H), 1.94-1.85 (m, 1 H), 0.98 (t, J = 7.1, 6 H), 0.91 (d, J = 6.5, 3 H), 0.85 (d, J = 6.5, 3 H). LC/MS: Anal. Calcd. for [M + H]⁺ $C_9H_{20}NO_2$: 174.15; found 174.15. |
| Cap-73 | 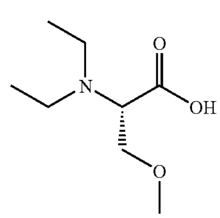 | ¹H NMR (DMSO-$d_6$, δ = 2.5 ppm, 500 MHz): δ 9.5 (br s, 1 H), 3.77 (dd, J = 10.8, 4.1, 1 H), 3.69-3.61 (m, 2 H), 3.26 (s, 3 H), 2.99-2.88 (m, 4 H), 1.13 (t, J = 7.2, 6 H). |
| Cap-74 | 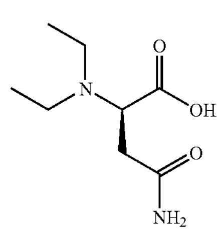 | ¹H NMR (DMSO-$d_6$, δ = 2.5 ppm, 500 MHz): δ 7.54 (s, 1 H), 6.89 (s, 1 H), 3.81 (t, J = 6.6, k, 1 H), 2.82-2.71 (m, 4 H), 2.63 (dd, J = 15.6, 7.0, 1 H), 2.36 (dd, J = 15.4, 6.3, 1 H), 1.09 (t, J = 7.2, 6 H). RT = 0.125 minutes (Cond. 2); LC/MS: Anal. Calcd. for [M + H]⁺ $C_8H_{17}N_2O_3$: 189.12; found 189.13. |

| Cap | Structure | Data |
|---|---|---|
| Cap-74x | 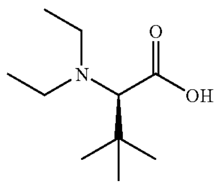 | LC/MS: Anal. Calcd. for [M + H]+ C10H22NO2: 188.17; found 188.21 |

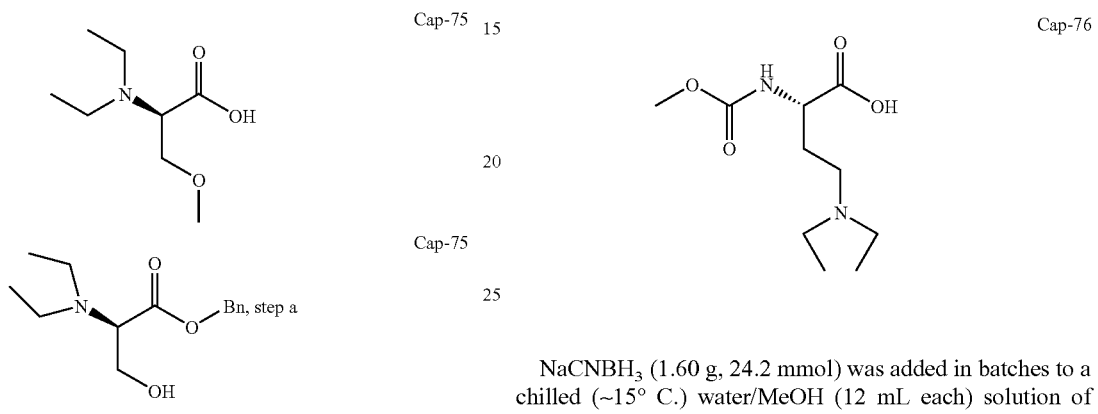

NaBH3CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H2O/TFA) to afford the TFA salt of (R)-benzyl 2-(diethylamino)-3-hydroxypropanoate as a colorless viscous oil (1.9 g). $^1$H NMR (DMSO-$d_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]+ C14H22NO3: 252.16; found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 µL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH3/Methanol. Removal of the volatile component in vacuo afforded Cap-75, contaminated with (R)-2-(diethylamino)-3-hydroxypropanoic acid, as a yellow semisolid (100 mg). The product was used as is without further purification.

NaCNBH3 (1.60 g, 24.2 mmol) was added in batches to a chilled (~15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with DOWEX® 50WX8-100 ion-exchange resin (column was washed with water and the compound was eluted with dilute NH4OH, prepared from 18 ml of NH4OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na2CO3 (0.243 g, 2.29 mmol), NaOH (4.6 mL of 1M/H2O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH2Cl2 (30 mL, 2×), and the aqueous phase was cooled with ice-water bath and acidified with concentrated HCl to a pH region of 2. The volatile component was then removed in vacuo and the crude material was free-based with MCX resin (6.0 g, column was washed with water, and sample was eluted with 2.0 M NH3/MeOH) to afford impure Cap-76 as an off-white solid (704 mg). $^1$H NMR (MeOH-$d_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]+ C10H21N2O4: 233.15; found 233.24.

Cap-77a and Cap-77b

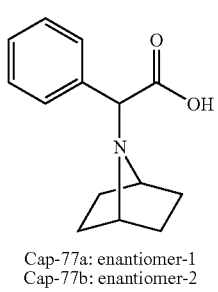

Cap-77a: enantiomer-1
Cap-77b: enantiomer-2

The synthesis of Cap-77 was conducted according to the procedure described for Cap-7 by using 7-azabicyclo[2.2.1]heptane for the $SN_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% $CO_2$—10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: $^1$H NMR (DMSO-$d_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ $C_{14}H_{18}NO_2$: 232.13; found 232.18. HRMS: Anal. Calcd. for [M+H]$^+$ $C_{14}H_{18}NO_2$: 232.1338; found 232.1340.

Cap-78

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H$_2$O/MeOH/TFA) to afford the TFA salt of Cap-78 as a colorless viscous oil (353 mg). $^1$H NMR (DMSO-$d_6$, δ=2.5 ppm, 400 MHz; after D$_2$O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ $C_{13}H_{18}NO_2$: 220.13; found 220.21. HRMS: Anal. Calcd. for [M+H]$^+$ $C_{13}H_{18}NO_2$: 220.1338; found 220.1343.

Cap-79

Ozone was bubbled through a cooled (−78° C.) CH$_2$Cl$_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 µL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH$_3$/MeOH elution) and a reverse phase HPLC (H$_2$O/MeOH/TFA) to afford Cap-79 containing unknown amount of morpholine.

In order to consume the morpholine contaminant, the above material was dissolved in CH$_2$Cl$_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and H$_2$O (0.5 mL) were added and stirring continued for 1.5 hr. The volatile component was removed in vacuo, and the resultant residue was passed through MCX resin (MeOH wash; 2.0 N NH$_3$/MeOH elution) to afford impure Cap-79 as a brown viscous oil, which was used for the next step without further purification.

Cap-80a and Cap-80b

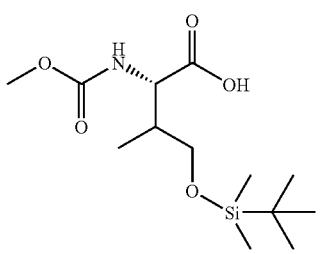

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11; found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a BIOTAGE® purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20; found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a BIOTAGE® (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22; found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluorine-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45; found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ C$_{31}$H$_{30}$NO$_3$: 464.45; found 464.52.

The relative stereochemical assignments of the DIBAL-reduction products were made based on NOE studies conducted on lactone derivatives prepared from each isomer by employing the following protocol: LiHMDS (50 μl of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a BIOTAGE® purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]$^+$ C$_{24}$H$_{21}$NNaO$_2$: 378.15; found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]$^+$ C$_{24}$H$_{21}$NNaO$_2$: 378.15; found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a BIOTAGE® (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]$^+$ C$_{37}$H$_{44}$NO$_3$Si: 578.31; found 578.40. (2S, 3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S, 3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (CELITE®-545), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/1-PrOH/H$_2$O) to afford (2S, 3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S, 3R)-2-amino-4-(tert-butyldimethylsilyloxy)-3-methylbutanoic acid. (2S,3S)-amino acid isomer: $^1$H NMR (Methanol-d$_4$, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for [M+H]$^+$ C$_{11}$H$_{26}$NO$_3$Si: 248.17; found 248.44. (2S, 3R)-amino acid isomer: $^1$H NMR (Methanol-d$_4$, δ 3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]$^+$ C$_{11}$H$_{26}$NO$_3$Si: 248.17; found 248.44.

Water (1 mL) and NaOH (0.18 mL of 1.0 M/H$_2$O, 0.18 mmol) were added to a mixture of (2S,3S)-2-amino-4-(tert-butyldimethylsilyloxy)-3-methylbutanoic acid (41.9 mg, 0.169 mmol) and Na$_2$CO$_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH$_2$Cl$_2$ (15 mL, 2×). The combined organic phase was dried (MgSO$_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-d$_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]$^+$ C$_{13}$H$_{27}$NNaO$_5$Si: 328.16; found 328.46. Cap-80b: $^1$H NMR (CDCl$_3$, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]$^+$ C$_{13}$H$_{27}$NNaO$_5$Si: 328.16; found 328.53. The crude products were utilized without further purification.

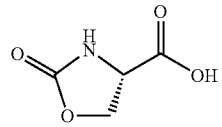

Cap-81

Prepared according to the protocol described by Falb et al., *Synthetic Communications*, 23:2839 (1993).

Cap-82 to Cap-85

Cap-82 to Cap-85 were synthesized from appropriate starting materials according to the procedure described for Cap-51 or Cap-13. The samples exhibited similar spectral profiles as that of their enantiomers (i.e., Cap-4, Cap-13, Cap-51 and Cap-52, respectively).

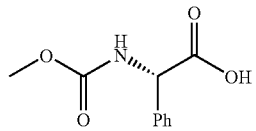

Cap-82

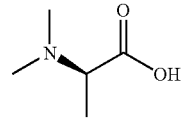

Cap-83

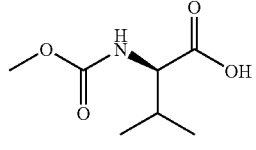

Cap-84

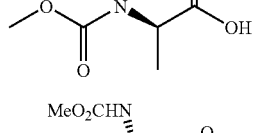

Cap-85

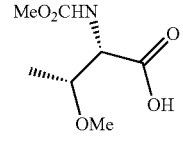

Cap-86

To a mixture of O-methyl-L-threonine (3.0 g, 22.55 mmol), NaOH (0.902 g, 22.55 mmol) in H$_2$O (15 mL) was added ClCO$_2$Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH$_2$Cl$_2$ (250 mL) and the combined organic phases were concentrated under in vacuo to afford a colorless oil (4.18 g, 97%) which was of sufficient purity for use in subsequent steps. $^1$H NMR (400 MHz, CDCl$_3$) δ 4.19 (s, 1H), 3.92-3.97 (m, 1H), 3.66 (s, 3H), 1.17 (d, J=7.7 Hz, 3H). LCMS: Anal. Calcd. for C$_7$H$_{13}$NO$_5$: 191; found: 190 (M−H)$^−$.

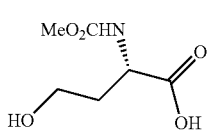

Cap-87

To a mixture of L-homoserine (2.0 g, 9.79 mmol), Na₂CO₃ (2.08 g, 19.59 mmol) in H₂O (15 mL) was added ClCO₂Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. ¹H NMR (400 MHz, CDCl₃) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C₇H₁₃NO₅: 191; found: 192 (M+H)⁺.

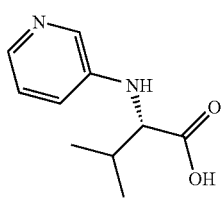

Cap-88

A mixture of L-valine (1.0 g, 8.54 mmol), 3-bromopyridine (1.8 mL, 18.7 mmol), K₂CO₃ (2.45 g, 17.7 mmol) and CuI (169 mg, 0.887 mmol) in DMSO (10 mL) was heated at 100° C. for 12 h. The reaction mixture was cooled to rt, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophilized. The title compound was obtained as a foam (1.02 g, 62%). ¹H NMR (400 MHz, DMSO-d₆) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for C₁₀H₁₄N₂O₂: 194; found: 195 (M+H)⁺.

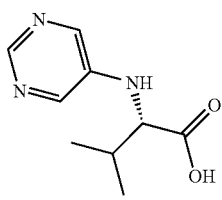

Cap-89

A mixture of L-valine (1.0 g, 8.54 mmol), 5-bromopyrimidine (4.03 g, 17.0 mmol), K₂CO₃ (2.40 g, 17.4 mmol) and CuI (179 mg, 0.94 mmol) in DMSO (10 mL) was heated at 100° C. for 12 h. The reaction mixture was cooled to RT, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophyllized. The title compound was obtained as a foam (1.02 g, 62%). ¹H NMR (400 MHz, CD₃OD) showed the mixture to contain valine and the purity could not be estimated. The material was used as is in subsequent reactions. LCMS: Anal. Calcd. for C₉H₁₃N₃O₂: 195; found: 196 (M+H)⁺.

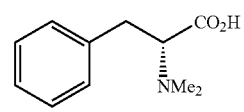

Cap-90

Cap-90 was prepared according to the method described for the preparation of Cap-1. The crude material was used as is in subsequent steps. LCMS: Anal. Calcd. for C₁₁H₁₅NO₂: 193; found: 192 (M−H)⁻.

Cap-91 to Cap-116

The following caps were prepared according to the method used for preparation of Cap-51 unless noted otherwise:

| Cap | Structure | LCMS |
|---|---|---|
| Cap-91 | ![structure with NHCO₂Me and CO₂H on phenylpropanoate] | LCMS: Anal. Calcd. for C₁₁H₁₃NO₄: 223; found: 222 (M - H)⁻. |
| Cap-92 | ![structure with NHCO₂Me and CO₂H on phenylpropanoate] | LCMS: Anal. Calcd. for C₁₁H₁₃NO₄: 223; found: 222 (M - H)⁻. |
| Cap-93 | ![structure with methyl carbamate and pyridylpropanoate] | LCMS: Anal. Calcd. for C₁₀H₁₂N₂O₄: 224; found: 225 (M + H)⁺. |

| Cap | Structure | LCMS |
|---|---|---|
| Cap-94 | 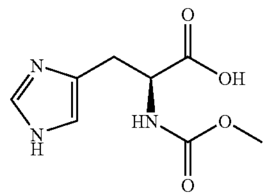 | LCMS: Anal. Calcd. for $C_8H_{11}N_3O_4$: 213; found: 214 $(M + H)^+$. |
| Cap-95 | 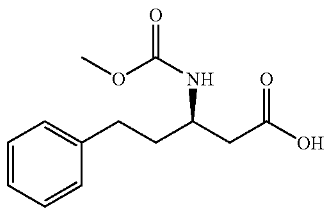 | LCMS: Anal. Calcd. for $C_{13}H_{17}NO_4$: 251; found: 250 $(M - H)^-$. |
| Cap-96 | 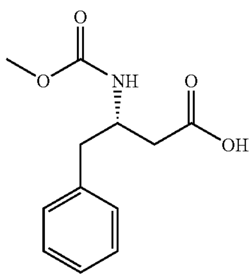 | LCMS: Anal. Calcd. for $C_{12}H_{15}NO_4$: 237; found: 236 $(M - H)^-$. |
| Cap-97 | 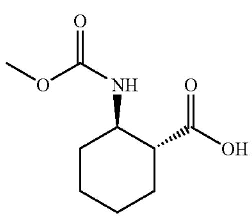 | LCMS: Anal. Calcd. for $C_9H_{15}NO_4$: 201; found: 200 $(M - H)^-$. |
| Cap-98 | 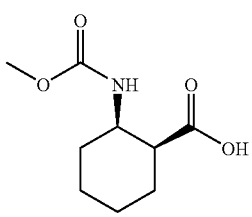 | LCMS: Anal. Calcd. for $C_9H_{15}NO_4$: 201; found: 202 $(M + H)^+$. |
| Cap-99 | 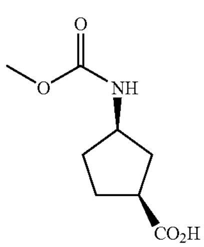 | $^1$H NMR (400 MHz, CD$_3$OD) δ 3.88-3.94 (m, 1 H), 3.60, 3.61 (s, 3 H), 2.80 (m, 1 H), 2.20 (m, 1 H), 1.82-1.94 (m, 3 H), 1.45-1.71 (m, 2 H). |
| Cap-99a | | $^1$H NMR (400 MHz, CD$_3$OD) δ 3.88-3.94 (m, 1 H), 3.60, 3.61 (s, 3 H), 2.80 (m, 1 H), 2.20 (m, 1 H), 1.82-1.94 (m, 3 H), 1.45-1.71 (m, 2 H). |
| Cap-100 | | LCMS: Anal. Calcd. for $C_{12}H_{14}NO_4F$: 255; found: 256 $(M + H)^+$. |
| Cap-101 | | LCMS: Anal. Calcd. for $C_{11}H_{13}NO_4$: 223; found: 222 $(M - H)^-$. |
| Cap-102 | | LCMS: Anal. Calcd. for $C_{11}H_{13}NO_4$: 223; found: 222 $(M - H)^-$ |
| Cap-103 | | LCMS: Anal. Calcd. for $C_{10}H_{12}N_2O_4$: 224; found: 225 $(M + H)^+$. |
| Cap-104 | | $^1$H NMR (400 MHz, CD$_3$OD) δ 3.60 (s, 3 H), 3.50-3.53 (m, 1 H), 2.66-2.69 and 2.44-2.49 (m, 1 H), 1.91-2.01 (m, 2 H), 1.62-1.74 (m, 4 H), 1.51-1.62 (m, 2 H). |

| Cap | Structure | LCMS |
|---|---|---|
| Cap-105 | (methyl carbamate of trans-4-aminocyclohexane carboxylic acid) | $^1$H NMR (400 MHz, CD$_3$OD) δ 3.60 (s, 3 H), 3.33-3.35 (m, 1 H, partially obscured by solvent), 2.37-2.41 and 2.16-2.23 (m, 1 H), 1.94-2.01 (m, 4 H), 1.43-1.53 (m, 2 H), 1.17-1.29 (m, 2 H). |
| Cap-106 | (N,N-diethyl-4-aminocyclohexane carboxylic acid) Prepared from cis-4-aminocyclohexane carboxylic acid and acetaldehyde by employing a similar procedure described for the synthesis of Cap-2. The crude HCl salt was passed through MCX (MeOH/H$_2$O/CH$_2$Cl$_2$ wash; 2 N NH$_3$/MeOH elution) to afford an oil, which was dissolved in CH$_3$CN/H$_2$O and lyophilized to afford a tan solid. | $^1$H NMR (400 MHz, CD$_3$OD) δ 3.16 (q, J = 7.3 Hz, 4 H), 2.38-2.41 (m, 1 H), 2.28-2.31 (m, 2 H), 1.79-1.89 (m, 2 H), 1.74 (app, ddd J = 3.5, 12.5, 15.9 Hz, 2 H), 1.46 (app dt J = 4.0, 12.9 Hz, 2 H), 1.26 (t, J = 7.3 Hz, 6 H) |
| Cap-107 | (thiazolyl-Ala with methyl carbamate) | LCMS: Anal. Calcd. for C$_8$H$_{10}$N$_2$O$_4$S: 230; found: 231 (M + H)$^+$. |
| Cap-108 | (N-benzyl-imidazolyl-Ala with methyl carbamate) | LCMS: Anal. Calcd. for C$_{15}$H$_{17}$N$_3$O$_4$: 303; found: 304 (M + H)$^+$. |
| Cap-109 | (3-pyridyl-Ala with methyl carbamate) | LCMS: Anal. Calcd. for C$_{10}$H$_{12}$N$_2$O$_4$: 224; found: 225 (M + H)$^+$. |
| Cap-110 | (4-pyridyl-Ala with methyl carbamate) | LCMS: Anal. Calcd. for C$_{10}$H$_{12}$N$_2$O$_4$: 224; found: 225 (M + H)$^+$. |
| Cap-111 | (Tyr phosphate methyl ester with methyl carbamate) | LCMS: Anal. Calcd. for C$_{12}$H$_{16}$NO$_8$P: 333; found: 334 (M + H)$^+$. |
| Cap-112 | (Trp with methyl carbamate) | LCMS: Anal. Calcd. for C$_{13}$H$_{14}$N$_2$O$_4$: 262; found: 263 (M + H)$^+$. |
| Cap-113 | (O-benzyl-Tyr with methyl carbamate) | LCMS: Anal. Calcd. for C$_{18}$H$_{19}$NO$_5$: 329; found: 330 (M + H)$^+$. |
| Cap-114 | (N-methoxycarbonyl azetidine-2-carboxylic acid) | $^1$H NMR (400 MHz, CDCl$_3$) δ 4.82-4.84 (m, 1 H), 4.00-4.05 (m, 2 H), 3.77 (s, 3 H), 2.56 (s, br, 2 H) |
| Cap-115 | (3-methylcarbamate-butyric acid) | $^1$H NMR (400 MHz, CDCl$_3$) δ 5.13 (s, br, 1 H), 4.13 (s, br, 1 H), 3.69 (s, 3 H), 2.61 (d, J = 5.0 Hz, 2 H), 1.28 (d, J = 9.1 Hz, 3 H). |
| Cap-116 | (3-methylcarbamate-4-methyl-pentanoic acid) | $^1$H NMR (400 MHz, CDCl$_3$) δ 5.10 (d, J = 8.6 Hz, 1 H), 3.74-3.83 (m, 1 H), 3.69 (s, 3 H), 2.54-2.61 (m, 2 H), 1.88 (sept, J = 7.0 Hz, 1 H), 0.95 (d, J = 7.0 Hz, 6 H). |

Cap-117 to Cap-123

For the preparation of Cap-117 to Cap-123 the Boc amino acids were obtained from commercially sources and were deprotected by treatment with 25% TFA in $CH_2Cl_2$. After complete reaction as judged by LCMS the solvents were removed in vacuo and the corresponding TFA salt of the amino acid was carbamoylated with methyl chloroformate according to the procedure described for Cap-51.

| Cap | Structure | LCMS |
|---|---|---|
| Cap-117 | 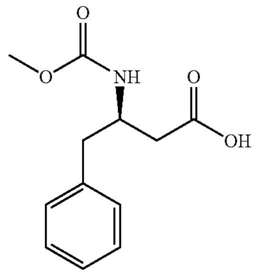 | LCMS: Anal. Calcd. for $C_{12}H_{15}NO_4$: 237; found: 238 $(M + H)^+$. |
| Cap-118 | 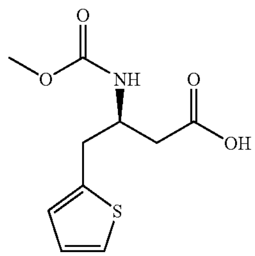 | LCMS: Anal. Calcd. for $C_{10}H_{13}NO_4S$: 243; found: 244 $(M + H)^+$. |
| Cap-119 | 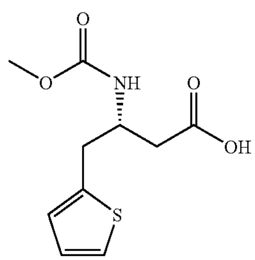 | LCMS: Anal. Calcd. for $C_{10}H_{13}NO_4S$: 243; found: 244 $(M + H)^+$. |
| Cap-120 | 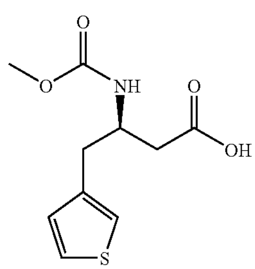 | LCMS: Anal. Calcd. for $C_{10}H_{13}NO_4S$: 243; found: 244 $(M + H)^+$. |
| Cap-121 | 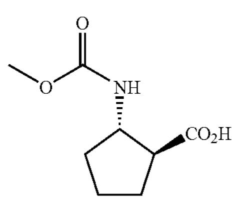 | $^1$H NMR (400 MHz, $CDCl_3$) δ 4.06-4.16 (m, 1 H), 3.63 (s, 3 H), 3.43 (s, 1 H), 2.82 and 2.66 (s, br, 1 H), 1.86-2.10 (m, 3 H), 1.64-1.76 (m, 2 H), 1.44-1.53 (m, 1 H). |
| Cap-122 | 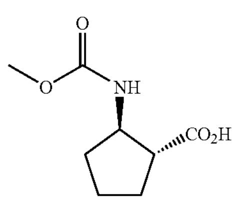 | $^1$H NMR profile is similar to that of its enantiomer, Cap-121. |

| Cap | Structure | LCMS |
|---|---|---|
| Cap-123 | 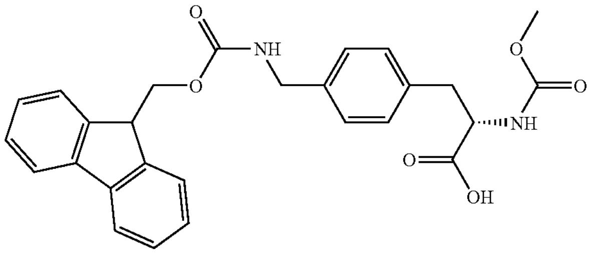 | LCMS: Anal. Calcd. for $C_{27}H_{26}N_2O_6$: 474; found: 475 $(M + H)^+$. |

Cap-124

The hydrochloride salt of L-threonine tent-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc—$CH_2Cl_2$-MeOH (1:1:0.1) and then the organic phase concentrated in vacuo to give a colorless oil which was shown by LCMS to be the desired product. Both crops were combined to give 0.52 g of a solid. $^1H$ NMR (400 MHz, $CD_3OD$) δ 4.60 (m, 1H), 4.04 (d, J=5.0 Hz, 1H), 1.49 (d, J=6.3 Hz, 3H). LCMS: Anal. Calcd. for $C_5H_7NO_4$: 145; found: 146 $(M+H)^+$.

Cap-125

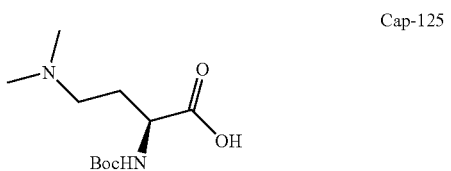

To a suspension of $Pd(OH)_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temp. The reaction mixture was filtered through a pad of diatomaceous earth (CELITE®), and the volatile component was removed in vacuo. The resulting crude material was used as is for the next step. LC/MS: Anal. Calcd. for $C_{11}H_{22}N_2O_4$: 246; found: 247 $(M+H)^+$.

Cap-126

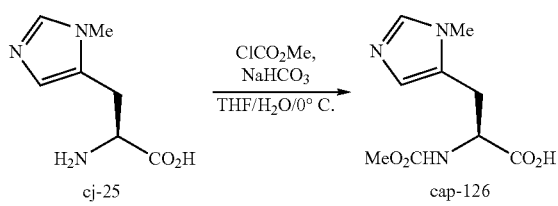

This procedure is a modification of that used to prepare Cap-51. To a suspension of 3-methyl-L-histidine (0.80 g, 4.70 mmol) in THF (10 mL) and $H_2O$ (10 mL) at 0° C. was added NaHCO₃ (0.88 g, 10.5 mmol). The resulting mixture was treated with $ClCO_2Me$ (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in $CH_2Cl_2$. The mixture was filtered and concentrated to give a light yellow foam (1.21 g). LCMS and $^1H$ NMR showed the material to be a 9:1 mixture of the methyl ester and the desired product. This material was taken up in THF (10 mL) and $H_2O$ (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1H$ NMR confirm the absence of the ester. The title compound was obtained as its HCl salt contaminated with inorganic salts (1.91 g, >100%). The compound was used as is in subsequent steps without further purification. $^1H$ NMR (400 MHz, $CD_3OD$) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LCMS: Anal. Calcd. for $C_9H_{13}N_3O_4$: 227.09; found: 228.09 $(M+H)^+$.

Cap-127

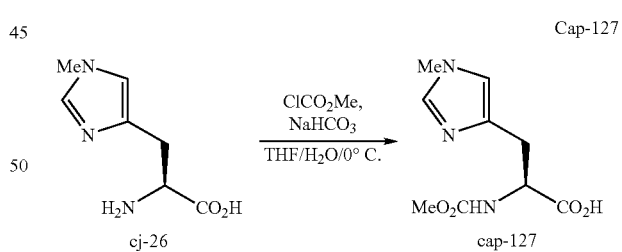

Cap-127 was prepared according to the method for Cap-126 above starting from (S)-2-amino-3-(1-methyl-1H-imidazol-4-yl)propanoic acid (1.11 g, 6.56 mmol), NaHCO₃ (1.21 g, 14.4 mmol) and $ClCO_2Me$ (0.56 mL, 7.28 mmol). The title compound was obtained as its HCl salt (1.79 g, >100%) contaminated with inorganic salts. LCMS and $^1H$ NMR showed the presence of ca. 5% of the methyl ester. The crude mixture was used as is without further purification. $^1H$ NMR (400 MHz, $CD_3OD$) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for $C_9H_{13}N_3O_4$: 227.09; found: 228 $(M+H)^+$.

Preparation of Cap-128

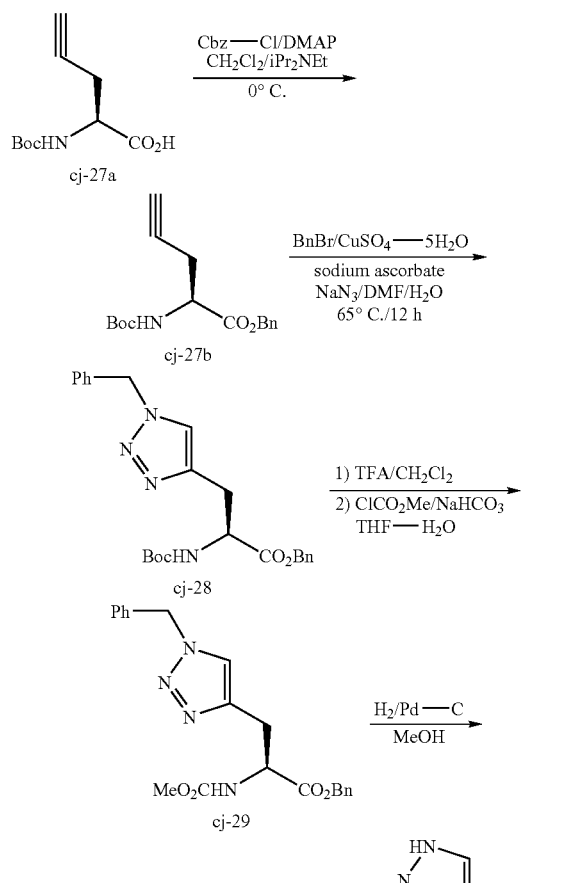

Step 1. Preparation of (S)-benzyl 2-(tent-butoxycarbonylamino)pent-4-ynoate (cj-27b)

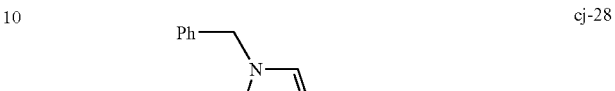

To a solution of cj-27a (1.01 g, 4.74 mmol), DMAP (58 mg, 0.475 mmol) and iPr$_2$NEt (1.7 mL, 9.8 mmol) in CH$_2$Cl$_2$ (100 mL) at 0° C. was added Cbz-Cl (0.68 mL, 4.83 mmol). The solution was allowed to stir for 4 h at 0° C., washed (1N KHSO$_4$, brine), dried (Na$_2$SO$_4$), filtered, and concentrated in vacuo. The residue was purified by flash column chromatography (TLC 6:1 hex:EtOAc) to give the title compound (1.30 g, 91%) as a colorless oil. $^1$H NMR (400 MHz, CDCl$_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for C$_{17}$H$_{21}$NO$_4$: 303; found: 304 (M+H)$^+$.

Step 2. Preparation of (S)-benzyl 3-(1-benzyl-1H-1,2,3-triazol-4-yl)-2-(tert-butoxycarbonylamino)propanoate (cj-28)

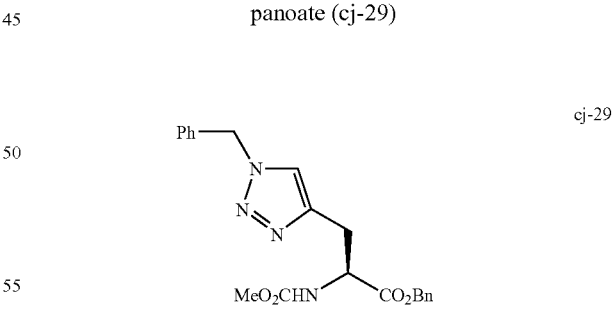

To a mixture of (S)-benzyl 2-(tert-butoxycarbonylamino)pent-4-ynoate (0.50 g, 1.65 mmol), sodium ascorbate (0.036 g, 0.18 mmol), CuSO$_4$·5H$_2$O (0.022 g, 0.09 mmol) and NaN$_3$ (0.13 g, 2.1 mmol) in DMF-H$_2$O (5 mL, 4:1) at rt was added BnBr (0.24 mL, 2.02 mmol) and the mixture was warmed to 65° C. After 5 h LCMS indicated low conversion. A further portion of NaN$_3$ (100 mg) was added and heating was continued for 12 h. The reaction was poured into EtOAc and H$_2$O and shaken. The layers were separated and the aqueous layer extracted 3× with EtOAc and the combined organic phases washed (H$_2$O×3, brine), dried (Na$_2$SO$_4$), filtered, and concentrated: The residue was purified by flash (BIOTAGE®, 40+M 0-5% MeOH in CH$_2$Cl$_2$; TLC 3% MeOH in CH$_2$Cl$_2$) to afford a light yellow oil which solidified on standing (748.3 mg, 104%). The NMR was consistent with the desired product but suggests the presence of DMF. The material was used as is without further purification. $^1$H NMR (400 MHz, DMSO-d$_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H). LCMS: Anal. Calcd. for C$_{24}$H$_{28}$N$_4$O$_4$: 436; found: 437 (M+H)$^+$.

Step 3. Preparation of (S)-benzyl 3-(1-benzyl-1H-1,2,3-triazol-4-yl)-2-(methoxycarbonylamino)propanoate (cj-29)

A solution of (S)-benzyl 3-(1-benzyl-1H-1,2,3-triazol-4-yl)-2-(tert-butoxycarbonylamino)propanoate (0.52 g, 1.15 mmol) in CH$_2$Cl$_2$ was added TFA (4 mL). The mixture was allowed to stir at room temperature for 2 h. The mixture was concentrated in vacuo to give a colorless oil which solidified on standing. This material was dissolved in THF—H$_2$O and cooled to 0° C. Solid NaHCO$_3$ (0.25 g, 3.00 mmol) was added followed by ClCO$_2$Me (0.25 mL, 3.25 mmol). After stirring for 1.5 h the mixture was acidified to pH~2 with 6N HCl and then poured into H$_2$O-EtOAc. The layers were separated and the aq phase extracted 2× with EtOAc. The combined org layers were washed (H₂O, brine), dried (Na₂SO₄), filtered, and concentrated in vacuo to give a colorless oil (505.8 mg, 111%, NMR suggested the presence of an unidentified impurity) which solidified while standing on the pump. The material was used as is without further purification. ¹H NMR (400 MHz, DMSO-d₆) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for C₂₁H₂₂N₄O₄: 394; found: 395 (M+H)⁺.

Step 4. Preparation of (S)-2-(methoxycarbonylamino)-3-(1H-1,2,3-triazol-4-yl)propanoic Acid (Cap-128)

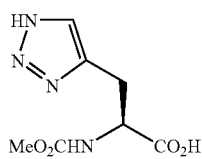

cap-128

(S)-Benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (CELITE®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. 1H NMR (400 MHz, DMSO-d₆) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for C₇H₁₀N₄O₄: 214; found: 215 (M+H)⁺.

Preparation of Cap-129

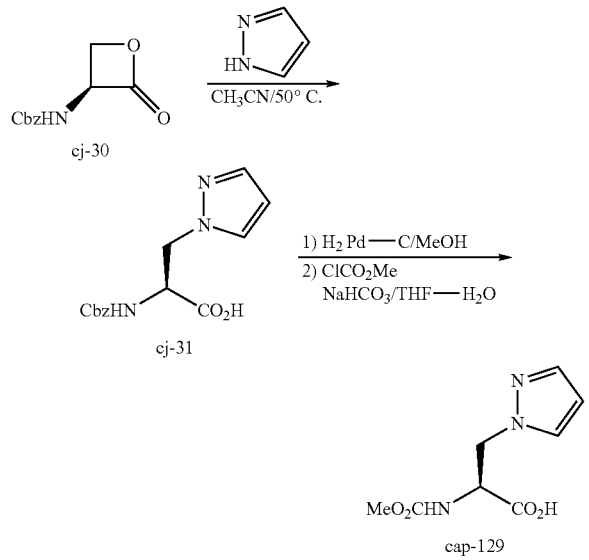

Step 1. Preparation of (S)-2-(benzyloxycarbonylamino)-3-(1H-pyrazol-1-yl)propanoic Acid (cj-31)

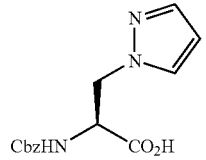

cj-31

A suspension of (S)-benzyl 2-oxooxetan-3-ylcarbamate (0.67 g, 3.03 mmol), and pyrazole (0.22 g, 3.29 mmol) in CH₃CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH₃CN (ca. 4 mL) to afford a second crop (43.5 mg). Total yield 370.4 mg (44%). m.p. 165.5-168° C. lit m.p. 168.5-169.5 [Vederas et al., J. Am. Chem. Soc., 107:7105 (1985)]. ¹H NMR (400 MHz, CD₃OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C₁₄H₁₅N₃O₄: 289; found: 290 (M+H)⁺.

Step 2. Preparation of (S)-2-(methoxycarbonylamino)-3-(1H-pyrazol-1-yl)propanoic Acid (Cap-129)

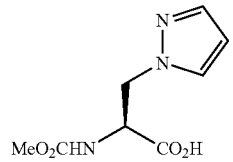

cap-129

(S)-2-(Benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL H₂O and a few drops of 6N HCl. The homogeneous solution was filtered through diatomaceous earth (CELITE®), and the MeOH removed in vacuo. The remaining solution was frozen and lyophyllized to give a yellow foam (188.9 mg). This material was suspended in THF—H₂O (1:1, mL) and then cooled to 0° C. To the cold mixture was added NaHCO₃ (146.0 mg, 1.74 mmol) carefully (evolution of CO₂). After gas evolution had ceased (ca. 15 min) ClCO₂Me (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried (Na₂SO₄), filtered, and concentrated to give the title compound as a colorless solid (117.8 mg, 79%). ¹H NMR (400 MHz, DMSO-d₆) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C$_8$H$_{11}$N$_3$O$_4$: 213; found: 214 (M+H)$^+$.

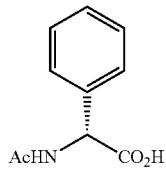

Cap-130

Cap-130 was prepared by acylation of commercially available (R)-phenylglycine analogous to the procedure given in: Calmes, M. et al., *Tetrahedron*, 43(10), 2285 (1987).

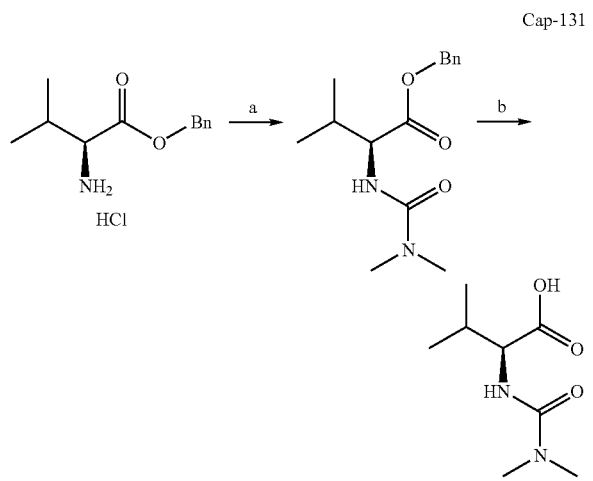

Cap-131

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO$_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1$H NMR (300 MHz, DMSO-d$_6$) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]$^+$ C$_{16}$H$_{22}$N$_2$O$_3$: 279.17; found 279.03.

Step b: To an MeOH (50 mL) solution of the intermediate prepared above (2.35 g; 8.45 mmol) was added Pd/C (10%; 200 mg) and the resulting black suspension was flushed with N$_2$ (3×) and placed under 1 atm of H$_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1$H NMR (500 MHz, DMSO-d$_6$) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]$^+$ C$_8$H$_{17}$N$_2$O$_3$: 189.12; found 189.04.

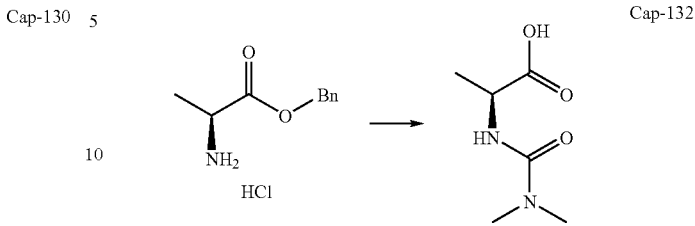

Cap-132

Cap-132 was prepared from (S)-benzyl 2-aminopropanoate hydrochloride according to the method described for Cap-131. $^1$H NMR (500 MHz, DMSO-d$_6$) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]$^+$ C$_6$H$_{13}$N$_2$O$_3$: 161.09; found 161.00.

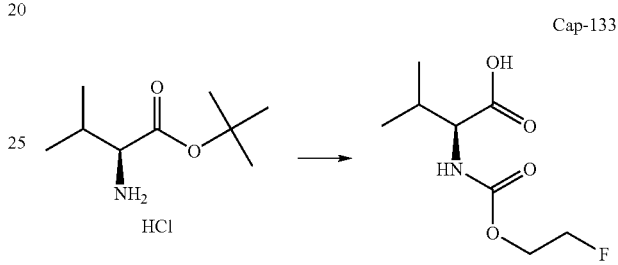

Cap-133

Cap-133 was prepared from (S)-tent-butyl 2-amino-3-methylbutanoate hydrochloride and 2-fluoroethyl chloroformate according to the method described for Cap-47. $^1$H NMR (500 MHz, DMSO-d$_6$) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

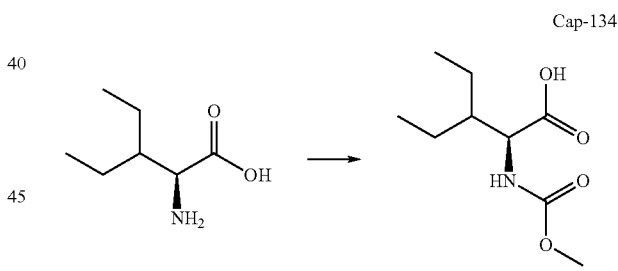

Cap-134

Cap-134 was prepared from (S)-diethyl alanine and methyl chloroformate according to the method described for Cap-51. $^1$H NMR (500 MHz, DMSO-d$_6$) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC/MS: Anal. Calcd. for [M+H]$^+$ C$_9$H$_{18}$NO$_4$: 204.12; found 204.02.

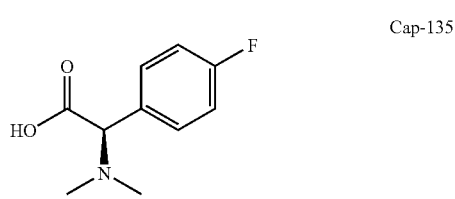

Cap-135

A solution of D-2-amino-(4-fluorophenyl)acetic acid (338 mg, 2.00 mmol), 1N HCl in diethylether (2.0 mL, 2.0 mmol)

and formalin (37%, 1 mL) in methanol (5 mL) was subjected to balloon hydrogenation over 10% palladium on carbon (60 mg) for 16 h at 25° C. The mixture was then filtered through CELITE® to afford the HCl salt of Cap-135 as a white foam (316 mg, 80%). $^1$H NMR (300 MHz, MeOH-d$_4$) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); R$_f$=0.19 min (Cond. MS-W5); 95% homogenity index; LRMS: Anal. Calcd. for [M+H]$^+$ C$_{10}$H$_{13}$FNO$_2$: 198.09; found: 198.10.

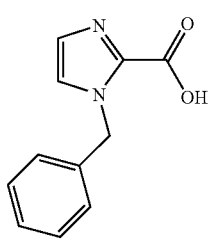

Cap-136

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). $^1$H NMR (300 MHz, DMSO-d$_6$) δ 7.94 (d, J=1.5 Hz, 1H), 7.71 (d, J=1.5 Hz, 1H), 7.50-7.31 (m, 5H), 5.77 (s, 2H); R$_f$=0.51 min (Cond. MS-W5); 95% homogenity index; LRMS: Anal. Calc. for [M+H]$^+$ C$_{11}$H$_{12}$N$_2$O$_2$: 203.08; found: 203.11.

2.00 mmol), bis(tri-tert-butylphosphine)palladium dichloride (10 mg, 0.02 mmol) and 2-(tributylstannyl)furan (378 μL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over Na$_2$SO$_4$, filtered and concentrated. Purification of the residue on silica gel (elution with 0% to 30% ethyl acetate/hexanes) afforded Cap-137, step a as a white solid which was used as is (230 mg, 105%). R$_f$=1.95 min (Cond. MS-W2); 90% homogeneity index; LRMS: Anal. Calc. for [M+H]$^+$ C$_{14}$H$_8$N$_2$O: 221.07; found: 221.12.

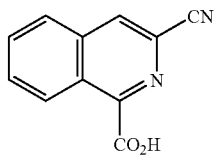

Cap-137

To a suspension of Cap-137, step a (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over Na$_2$SO$_4$ filtered and concentrated. Trituration of the residue with hexanes afforded Cap-137 (55 mg, 55%) as a grayish-colored solid. R$_f$=1.10 min (Cond. MS-W2); 90% homogeneity index; LCMS: Anal. Calc. for [M+H]$^+$ C$_{11}$H$_8$N$_2$O$_2$: 200.08; found: 200.08.

Cap-138 to Cap-158

Synthetic Strategy. Method A.

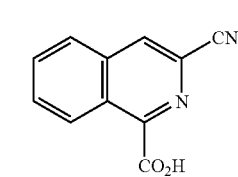

Cap-137

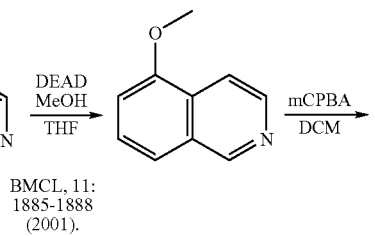

BMCL, 11: 1885-1888 (2001).

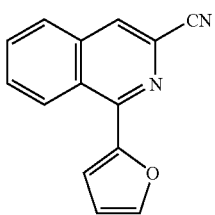

Cap-137, step a

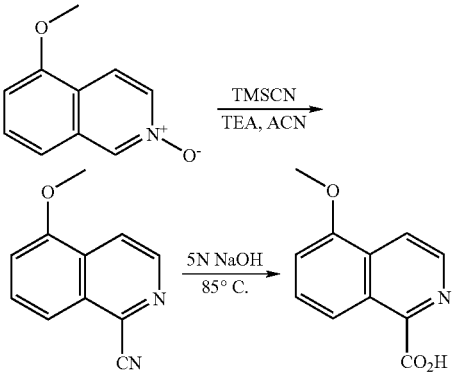

A suspension of 1-chloro-3-cyanoisoquinoline (188 mg, 1.00 mmol; prepared according to the procedure in WO 2003/099274) (188 mg, 1.00 mmol), cesium fluoride (303.8 mg,

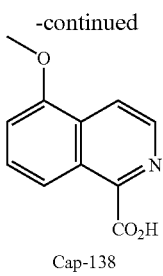

Cap-138

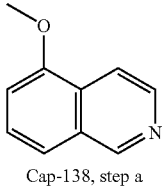

Cap-138, step a

To a stirred suspension of 5-hydroxyisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and purified (elution with 40% ethyl acetate/hexanes) to afford Cap-138, step a as a light yellow solid (1.00 g, 45%). $^1$H NMR (CDCl$_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); R$_f$=0.66 min (Cond. D2); 95% homogeneity index; LCMS: Anal. Calc. for [M+H]$^+$ C$_{10}$H$_{10}$NO: 160.08; found: 160.10.

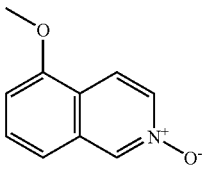

Cap-138, step b

To a stirred solution of Cap-138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated to afford Cap-138, step b as a pale, yellow solid which was sufficiently pure to carry forward (2.15 g, 83.3%). $^1$H NMR (CDCl$_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); R$_f$ 0.92 min, (Cond. D1); 90% homogenity index; LCMS: Anal. Calc. for [M+H]$^+$ C$_{10}$H$_{10}$NO$_2$: 176.07; found: 176.0.

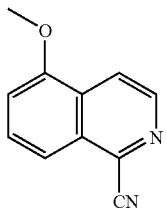

Cap-138, step c

To a stirred solution of Cap-138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over $Na_2SO_4$ and solvent concentration. The residue was flash chromatographed on silica gel (elution with 5% ethyl acetate/hexanes) to 25% ethyl acetate/hexanes) to afford Cap-138, step c (498.7 mg) as a white, crystalline solid along with 223 mg of additional Cap-138, step c recovered from the filtrate. $^1$H NMR (CDCl$_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); R$_f$=1.75 min, (Cond. D1); 90% homogeneity index; LCMS: Anal. Calc. for [M+H]$^+$ C$_{11}$H$_9$N$_2$O: 185.07; found: 185.10.

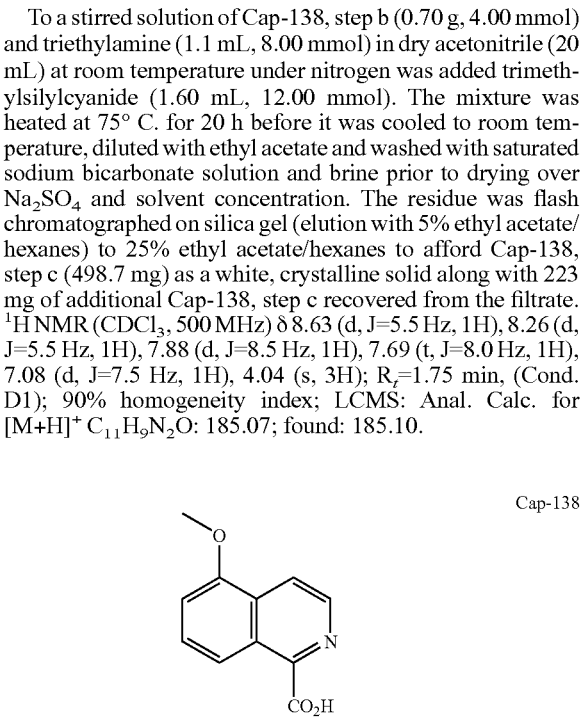

Cap-138

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over $Na_2SO_4$, concentrated to ¼ volume and filtered to afford Cap-138 as a yellow solid (0.44 g, 88.9%). $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); R$_f$=0.70 min (Cond. D1); 95% homogenity index; LCMS: Anal. Calc. for [M+H]$^+$ C$_{11}$H$_{10}$NO$_3$: 204.07; found: 204.05.

Synthetic Strategy. Method B (derived from *Tetrahedron Letters*, 42:6707 (2001)).

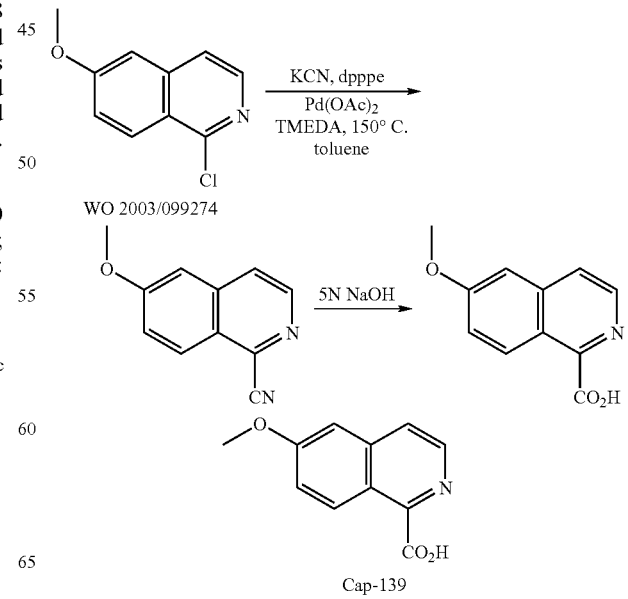

Cap-139

Cap-139, step a

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis (diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over $Na_2SO_4$, filtered and concentrated. The residue was purified on silica gel eluting with 5% ethyl acetate/hexanes to 25% ethyl acetate/hexanes to afford Cap-139, step a as a white solid (669.7 mg). $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); $R_t$=1.66 min (Cond. D1); 90% homogenity index; LCMS: Anal. Calc. for [M+H]$^+$ $C_{11}H_9N_2O$: 185.07; found: 185.20.

Cap-139

Cap-139 was prepared from the basic hydrolysis of Cap-139, step a with 5N NaOH according to the procedure described for Cap-138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); $R_t$=0.64 min (Cond. D1); 90% homogenity index; LCMS: Anal. Calc. for [M+H]$^+$ $C_{11}H_{10}NO_3$: 204.07; found: 204.05.

Cap-140

Cap-140, step a

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 μL of acetone cyanohydrin in 4.34 mL DMA) was added in 1 mL portions over 18 h using a syringe pump. The mixture was then partitioned between ethyl acetate and water and the organic layer was separated, washed with brine, dried over $Na_2SO_4$, filtered and concentrated. The residue was purified on silica gel eluting with 10% ethyl acetate/hexanes to 40% ethyl acetate/hexanes to afford Cap-140, step a as a yellow solid (160 mg, 34%). $R_t$=2.46 min (Cond. MS-W2); 90% homogenity index; LCMS: Anal. Calc. for [M+H]$^+$ $C_{12}H_9ClN_2O$: 233.05; found: 233.08.

Cap-140

Cap-140 was prepared by the acid hydrolysis of Cap-140, step a with 12N HCl as described in the procedure for the preparation of Cap-141, described below. $R_t$=2.24 min (Cond. MS-W2); 90% homogenity index; LCMS: Anal. Calc. for [M+H]$^+$ $C_{12}H_{11}ClNO_3$: 252.04; found: 252.02.

Cap-141

Cap-141, step a

Cap-141, step a was prepared from 1-bromo-3-fluoroiso-quinoline (prepared from 3-amino-1-bromoisoquinoline using the procedure outlined in J. Med. Chem., 13:613 (1970)) as described in the procedure for the preparation of Cap-140, step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); $R_t$=1.60 min (Cond. D1); 90% homogenity index; LCMS: Anal. Calc. for [M+H]$^+$ $C_{10}H_6FN_2$: 173.05; found: 172.99.

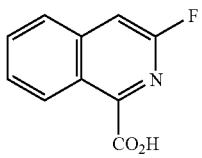

Cap-141

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 as an off-white solid (44.1 mg, 47.8%). The filtrate was diluted with dichloromethane and washed with brine, dried over $Na_2SO_4$, and concentrated to afford additional Cap-141 which was sufficiently pure to be carried forward directly (29.30 mg, 31.8%). $^1$H NMR (DMSO-$d_5$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); $R_t$=1.33 min (Cond. D1); 90% homogenity index; LCMS: Anal. Calc. for $[M+H]^+$ $C_{10}H_7FNO_2$: 192.05; found: 191.97.

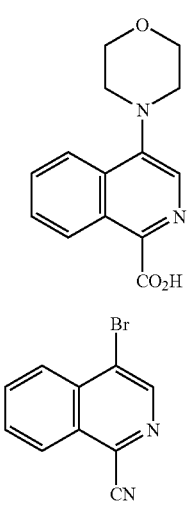

Cap-142

Cap-142, step a

Cap-142, step a was prepared from 4-bromoisoquinoline N-oxide as described in the two-step procedure for the preparation of Cap-138, steps b and c. $R_t$=1.45 min (Cond. MS-W1); 90% homogenity index; LCMS: Anal. Calc. for $[M+H]^+$ $C_{10}H_6BrN_2$: 232.97; found: 233.00.

Cap-142, step b

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C. and filtered through diatomaceous earth (CELITE®). Purification of the residue on silica gel, eluting with 10% to 70% ethyl acetate/hexanes afforded Cap-142, step b (38 mg, 32%) as a yellow solid, which was carried forward directly. $R_t$=1.26 min (Cond. MS-W1); 90% homogenity index; LCMS: Anal. Calc. for $[M+H]^+$ $C_{14}H_{14}N_3O$: 240.11; found: 240.13.

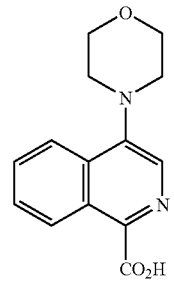

Cap-142

Cap-142 was prepared from Cap-142, step b with 5N sodium hydroxide as described in the procedure for Cap-138. $R_t$=0.72 min (Cond. MS-W1); 90% homogenity index; LCMS: Anal. Calc. for $[M+H]^+$ $C_{14}H_{15}N_2O_3$: 259.11; found: 259.08.

Cap-143

Cap-143, step a

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 μL, 2.00 mmol) was added. The mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over $Na_2SO_4$, filtered and concentrated. Purification of the residue on silica gel eluting with 0% to 70% ethyl acetate/hexanes afforded Cap-143, step a as a yellow solid (180 mg, 31%). $R_t$=1.75 min (Cond. MS-W1); 90% homogenity index; LCMS: Anal. Calc. for $[M+H]^+$ $C_{13}H_{14}BrN_2O$: 293.03; found: 293.04.

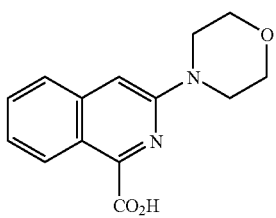

Cap-143

To a cold (−60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by a reverse phase HPLC (MeOH/water/TFA) afforded Cap-143 (16 mg, 12%). $R_f$=1.10 min (Cond. MS-W1); 90% homogenity index; LCMS: Anal. Calc. for [M+H]$^+$ $C_{14}H_{15}N_2O_3$: 259.11; found: 259.08.

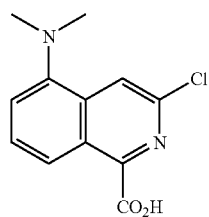

Cap-144

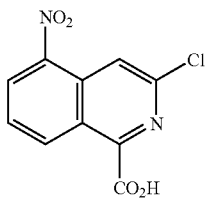

Cap-144, step a 1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_f$=2.01 min. (Cond. D1); 95% homogenity index; LCMS: Anal. Calc. for [M+H]$^+$ $C_9H_5Cl_2N_2O_2$: 242.97; found: 242.92.

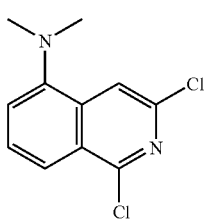

Cap-144, step b

Cap-144, step a (0.30 g, 1.23 mmol) was taken up in methanol (60 mL) and treated with platinum oxide (30 mg), and the suspension was subjected to Parr hydrogenation at 7 psi $H_2$ for 1.5 h. Then formalin (5 mL) and additional platinum oxide (30 mg) were added, and the suspension was resubjected to Parr hydrogenation at 45 psi $H_2$ for 13 h. It was then suction-filtered through diatomaceous earth (CELITE®) and concentrated down to ¼ volume. Suction-filtration of the ensuing precipitate afforded the title compound as a yellow solid which was flash chromatographed on silica gel eluting with 5% ethyl acetate in hexanes to 25% ethyl acetate in hexanes to afford Cap-144, step b (231 mg, 78%) as a pale yellow solid. $R_f$ 2.36 min (Cond. D1); 95% homogenity index; $^1$H NMR (400 MHz, CDCl$_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LCMS: Anal. Calc. for [M+H]$^+$ $C_{11}H_{11}C_{12}N_2$: 241.03; found: 241.02. HRMS: Anal. Calc. for [M+H]$^+$ $C_{11}H_{11}Cl_2N_2$: 241.0299; found: 241.0296.

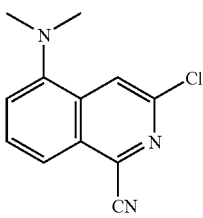

Cap-144, step c

Cap-144, step c was prepared from Cap-144, step b according to the procedure described for the preparation of Cap-139, step a. $R_f$=2.19 min (Cond. D1); 95% homogenity index; LCMS: Anal. Calc. for [M+H]$^+$ $C_{12}H_{11}ClN_3$: 232.06; found: 232.03. HRMS: Anal. Calc. for [M+H]$^+$ $C_{12}H_{11}ClN_3$: 232.0642; found: 232.0631.

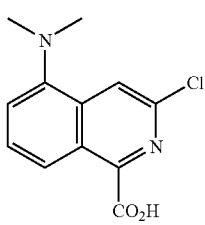

Cap-144

Cap-144 was prepared according to the procedure described for Cap-141. $R_f$=2.36 min (Cond. D1); 90%; LCMS: Anal. Calc. for [M+H]$^+$ $C_{12}H_{12}ClN_2O_2$: 238.01; found: 238.09.

Cap-145 to Cap-162

Cap-145 to Cap-162 were prepared from the appropriate 1-chloroisoquinolines according to the procedure described for the preparation of Cap-138 (Method A) or Cap-139 (Method B) unless noted otherwise as outlined below.

| Cap | Structure | Method | Hydrolysis | Rt (LC-Cond.); % homogeneity index; MS data |
|---|---|---|---|---|
| Cap-145 | 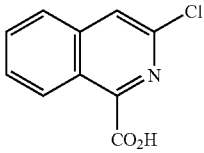<br>Prepared from commercially available 1,3-dichloroisoquinoline. | B | 12 N HCl | 1.14 min (Cond. MS-W1); 90%; LCMS: Anal. Calc. for [M + H]$^+$ $C_{10}H_7ClNO_2$: 208.02; found: 208.00. |
| Cap-146 | 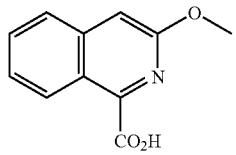<br>Prepared from commercially available -hydroxyisoquinoline. | A | 5 N NaOH | 1.40 min (Cond. D1); 95%; LCMS: Anal. Calc. for [M + H]$^+$ $C_{11}H_{10}NO_3$: 204.07; found: 204.06. |
| Cap-147 | 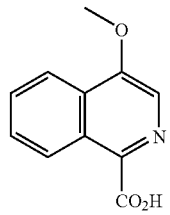<br>Prepared from commercially available 1-chloro-4-hydroxyisoquinoline. | B | 5 N NaOH | 0.87 min (Cond. D1); 95%; LCMS: Anal. Calc. for [M + H]$^+$ $C_{11}H_{10}NO_3$: 204.07; found: 204.05. |
| Cap-148 | 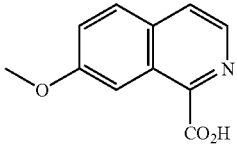<br>Prepared from commercially available 7-hydroxyisoquinoline. | A | 5 N NaOH | 0.70 min (Cond. D1); 95%; LCMS: Anal. Calc. for [M + H]$^+$ $C_{11}H_{10}NO_3$: 204.07; found: 204.05. |
| Cap-149 | 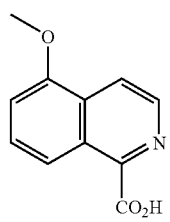<br>Prepared from commercially available 5-hydroxyisoquinoline. | A | 5 N NaOH | 0.70 min (Cond. D1); 95%; LCMS: Anal. Calc. for [M + H]$^+$ $C_{11}H_{10}NO_3$: 204.07; found: 204.05. |

| Cap | Structure | Method | Hydrolysis | Rt (LC-Cond.); % homogeneity index; MS data |
|---|---|---|---|---|
| Cap-150 | (8-methoxyisoquinoline-1-carboxylic acid, TFA salt) Prepared from 8-methoxy-1-chloroisoquinoline, which can be synthesized following the procedure in WO 2003/099274. | A | 12 N HCl | 0.26 min (Cond. D1); 95%; LCMS: Anal. Calc. for [M + H]$^+$ C$_{11}$H$_{10}$NO$_3$: 204.07; found: 204.04. |
| Cap-151 | (5-methoxy-3-chloroisoquinoline-1-carboxylic acid) Prepared from 5-methoxy-1,3-dichloroisoquinoline, which can be synthesized following the procedure in WO 2005/051410. | B | 12 N HCl | 1.78 min (Cond. D1); 90%; LCMS: Anal. Calc. for [M + H]$^+$ C$_{11}$H$_9$ClNO$_3$: 238.03; found: 238.09. |
| Cap-152 | (6-methoxy-3-chloroisoquinoline-1-carboxylic acid) Prepared from commercially available 6-methoxy-1,3-dichloroisoquinoline. | B | 12 N HCl | 1.65 min (Cond. D1); 95%; LCMS: Anal. Calc. for [M + H]$^+$ C$_{11}$H$_9$ClNO$_3$: 238.00; found: 238.09. |
| Cap-153 | (4-bromoisoquinoline-1-carboxylic acid) Prepared from 4-bromoisoquinoline, which can be synthesized following the procedure in WO 2003/062241. | A | 6 N HCl | 1.18 min (Cond. MS-W1); 95%; LCMS: Anal. Calc. for [M + H]$^+$ C$_{10}$H$_7$BrNO$_2$: 251.97; found: 251.95. |
| Cap-154 | (7-fluoroisoquinoline-1-carboxylic acid) Prepared from 7-fluoro-1-chloroisoquinoline, which can be synthesized following the procedure in WO 2003/099274. | B | 5 N NaOH | 0.28 min (Cond. MS-W1); 90%; LCMS: Anal. Calc. for [M + H]$^+$ C$_{10}$H$_7$FNO$_2$: 192.05; found: 192.03. |

| Cap | Structure | Method | Hydrolysis | Rt (LC-Cond.); % homogeneity index; MS data |
|---|---|---|---|---|
| Cap-155 | 7-chloroisoquinoline-1-carboxylic acid. Prepared from 1,7-dichloroisoquinoline, which can be synthesized following the procedure in WO 2003/099274. | B | 5 N NaOH | 0.59 min (Cond. MS-W1); 90%; LCMS: Anal. Calc. for [M + H]$^+$ $C_{10}H_7ClNO_2$: 208.02; found: 208.00. |
| Cap-156 | 6-chloroisoquinoline-1-carboxylic acid. Prepared from 1,6-dichloroisoquinoline, which can be synthesized following the procedure in WO 2003/099274. | B | 5 N NaOH | 0.60 min (Cond. MS-W1); 90%; LCMS: Anal. Calc. for [M + H]$^+$ $C_{10}H_7ClNO_2$: 208.02; found: 208.03. |
| Cap-157 | 4-chloroisoquinoline-1-carboxylic acid. Prepared from 1,4-dichloroisoquinoline, which can be synthesized following the procedure in WO 2003/062241. | B | 12 N HCl | 1.49 min (Cond. D1); 95%; LCMS: Anal. Calc. for [M + H]$^+$ $C_{10}H_{17}ClNO$: 208.02; found: 208.00. |
| Cap-158 | 5-chloroisoquinoline-1-carboxylic acid. Prepared from 1,5-dichloroisoquinoline, which can be synthesized following the procedure in WO 2003/099274. | B | 5 N NaOH | 0.69 min (Cond. MS-W1); 90%; LCMS: Anal. Calc. for [M + H]$^+$ $C_{10}H_7ClNO_2$: 208.02; found: 208.01. |
| Cap-159 | 5-fluoroisoquinoline-1-carboxylic acid. Prepared from 5-fluoro-1-chloroisoquinoline, which can be synthesized following the procedure in WO 2003/099274. | B | 5 N NaOH | 0.41 min (Cond. MS-W1); 90%; LCMS: Anal. Calc. for [M + H]$^+$ $C_{10}H_7FNO_2$: 192.05; found: 192.03. |

| Cap | Structure | Method | Hydrolysis | Rt (LC-Cond.); % homogeneity index; MS data |
|---|---|---|---|---|
| Cap-160 | 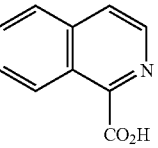 Prepared from 6-fluoro-1-chloroisoquinoline, which can be synthesized following the procedure in WO 2003/099274. | B | 5 N NaOH | 0.30 min (Cond. MS-W1); 90%; LCMS: Anal. Calc. for [M + H]$^+$ $C_{10}H_7FNO_2$: 192.05; found: 192.03. |
| Cap-161 | 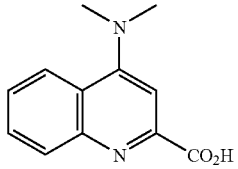 Prepared from 4-bromoquinoline-2-carboxylic acid and dimethylamine (DMSO, 100° C.). | — | — | 0.70 min (Cond. D1); 95%; LCMS: Anal. Calc. for [M + H]$^+$ $C_{12}H_{13}N_2O_2$: 217.10; found: 217.06. |
| Cap-162 | 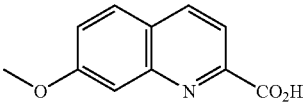 Prepared from m-anisidine following the procedure described in J. Hetero. Chem., 17 (1993) and Heterocycles, 60:953 (2003). | — | — | 0.65 min (Cond. M3); 95%; LCMS: Anal. Calc. for [M + H]$^+$ $C_{11}H_{10}NO_3$: 204.07; found: 203.94. |

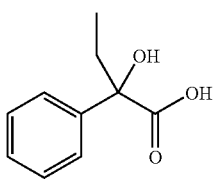

Cap-163

To a solution of 2-ketobutyric acid (1.0g, 9.8 mmol) in diethylether (25 ml) was added phenylmagnesium bromide (22 ml, 1 M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1$H NMR (DMSO-$d_6$, δ=2.5 ppm, 500 MHz): 12.71 (br s, 1 H), 7.54-7.52 (m, 2H), 7.34-7.31 (m, 2H), 7.26-7.23 (m, 1H), 5.52-5.39 (br 5, 1H), 2.11 (m, 1H), 1.88 (m, 1H), 0.79 (app t, J=7.4 Hz, 3H).

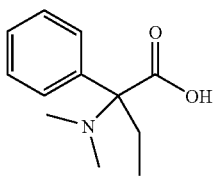

Cap-164

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over CELITE® and concentrated in vacuo, the residue was taken up in MeOH (36 mL) and the product was purified with a reverse phase HPLC (MeOH/H$_2$O/TFA) to afford the TFA salt of Cap-164 as a white solid (1.7 g). $^1$H NMR (DMSO-$d_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

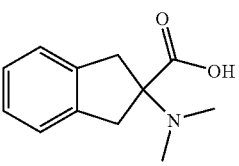

Cap-165

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/H$_2$O/TFA) to afford the TFA salt of Cap-165 as a viscous oil (120.2 mg). $^1$H NMR (DMSO-$d_6$, 6-2.5 ppm, 500 MHz): 7.29-7.21 (m, 4H), 3.61 (d, J=17.4 Hz, 2H), 3.50 (d, J=17.4 Hz, 2H), 2.75 (s, GH). LC/MS: Anal. Calcd. for [M+H]$^+$ $C_{12}H_{16}NO_2$: 206.12; found: 206.07.

Cap-166a: Diastereomer-1
Cap-166b: Diastereomer-2

Cap-166a and Cap-166b

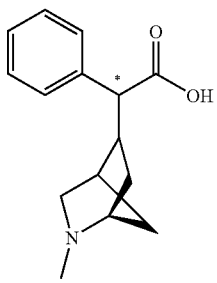

Cap-166a and Cap-166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chrialcel OJ column, 20×250 mm, 10 μm eluting with 85:15 heptane/ethanol mixture at 10 mL/min elution rate for 25 min. Cap-166b: $^1$H NMR (DMSO-d$_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC/MS: Anal. Calcd. for [M+H]$^+$ C$_{14}$H$_{19}$N$_2$O$_2$: 247.14; found: 247.11.

Cap-167

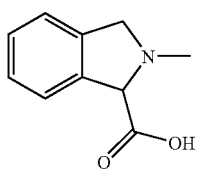

A solution of racemic Boc-1,3-dihydro-2H-isoindole carboxylic acid (1.0 g, 3.8 mmol) in 20% TFA/CH$_2$Cl$_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to H$_2$ (40 PSI) in a Parr bottle for 23 h. The reaction mixture was filtered over CELITE® and concentrated in vacuo to afford Cap-167 as a yellow foam (873.5 mg). $^1$H NMR (DMSO-d$_6$, δ=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC/MS: Anal. Calcd. for [M+H]$^+$ C$_{10}$H$_{12}$NO$_2$: 178.09; found: 178.65.

Cap-168

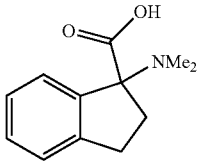

Racemic Cap-168 was prepared from racemic Boc-aminoindane-1-carboxylic acid according to the procedure described for the preparation of Cap-167. The crude material was employed as such.

Cap-169

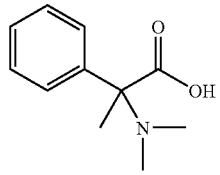

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered over CELITE® and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC/MS: Anal. Calcd. for [M+H]$^+$ C$_{11}$H$_{16}$NO$_2$: 194.12; found: 194.12.

Cap-170

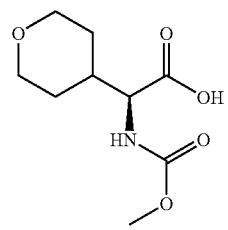

To (5)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170a colorless residue. $^1$H NMR (500 MHz, DMSO-d$_6$) δ ppm 12.65 (1 H, br s), 7.44 (1 H, d, J=8.24 Hz), 3.77-3.95 (3 H, m), 3.54 (3 H, s), 3.11-3.26 (2 H, m), 1.82-1.95 (1 H, m), 1.41-1.55 (2 H, m), 1.21-1.39 (2 H, m); LC/MS: Anal. Calcd. for [M+H]$^+$ C$_9$H$_{16}$NO$_5$: 218.1; found 218.1.

Cap-171

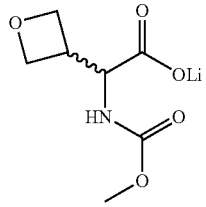

A solution of methyl 2-(benzyloxycarbonylamino)-2-(oxetan-3-ylidene)acetate (200 mg, 0.721 mmol; *Il Farmaco*, 56:609-613 (2001)) in ethyl acetate (7 ml) and CH$_2$Cl$_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 CH$_2$Cl$_2$/MeOH: visualized with stain made from 1 g Ce(NH$_4$)$_2$SO$_4$, 6 g ammonium molybdate, 6 ml sulfuric acid, and 100 ml water) indicated complete conversion. The reaction was filtered through CELITE® and concentrated. The residue was purified via BIOTAGE® (load with dichloromethane on 25 samplet; elute on 25S column with dichloromethane for 3 CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl) acetate as a colorless oil. $^1$H NMR (500 MHz, CHLOROFORM-d) δ ppm 3.29-3.40 (m, J=6.71 Hz, 1 H) 3.70 (s, 3 H) 3.74 (s, 3 H) 4.55 (t, J=6.41 Hz, 1H) 4.58-4.68 (m, 2 H) 4.67-4.78 (m, 2 H) 5.31 (br s, 1 H). LC/MS: Anal. Calcd. for [M+H]$^+$ C$_8$H$_{14}$NO$_5$: 204.2; found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnight at ambient temperature. TLC (1:1 EA/Hex; Hanessian stain [1 g Ce(NH$_4$)$_2$SO$_4$, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnight providing 55 mg lithium 2-(methoxycarbonylamino)-2-(oxetan-3-yl)acetate as a colorless solid. $^1$H NMR (500 MHz, MeOD) δ ppm 3.39-3.47 (m, 1 H) 3.67 (s, 3 H) 4.28 (d, J=7.93 Hz, 1 H) 4.64 (t, J=6.26 Hz, 1 H) 4.68 (t, J=7.02 Hz, 1 H) 4.73 (d, J=7.63 Hz, 2 H).

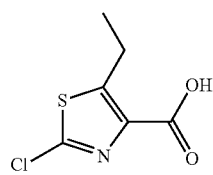

Cap-172

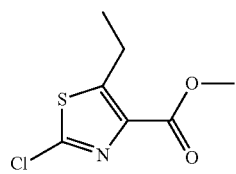

Cap-172, step a

The following diazotization step was adapted from Barton, A.; Breukelman, S. P.; Kaye, P. T.; Meakins, G. D.; Morgan, D. J. *J. C. S. Perkin Trans* 1 1982, 159-164: A solution of NaNO$_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), CuSO$_4$.5H$_2$O (330 mg, 1.32 mmol), NaCl (260 mg, 4.45 mmol) and H$_2$SO$_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over MgSO$_4$ and concentrated to give methyl 2-chloro-5-ethylthiazole-4-carboxylate (i.e. Cap-172, step a) (175 mg, 85%) as an orange oil (80% pure) which was used directly in the next reaction. R$_f$=1.99 min (Cond. -MD1); LC/MS: Anal. Calcd. for [M+H]$^+$ C$_7$H$_9$ClNO$_2$S: 206.01; found: 206.05.

Cap-172

To a solution of methyl 2-chloro-5-ethylthiazole-4-carboxylate (175 mg) in THF/H$_2$O/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-172 (60 mg, 74%) as a red solid which was used without further purification. $^1$H NMR (300 MHz, DMSO-d$_5$) δ ppm 13.03-13.42 (1 H, m), 3.16 (2 H, q, J=7.4 Hz), 1.23 (3 H, t, J=7.5 Hz). R$_f$=1.78 min (Cond.-MD1); LC/MS: Anal. Calcd. for [M+H]$^+$ C$_6$H$_7$ClNO$_2$S: 191.99; found: 191.99.

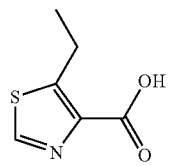

Cap-173

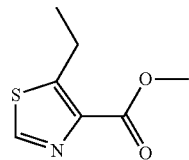

Cap-173, step a

The following diazotization step was adapted from Barton, A.; Breukelman, S. P.; Kaye, P, T.; Meakins, G. D.; Morgan, D. J. J. C. S. *Perkin Trans* 1 1982, 159-164: A solution of NaNO$_2$ (150 mg, 2.17 mmol) in water (1.0 mL) was added dropwise to a stirred, cold (0° C.) solution of methyl 2-amino-5-ethyl-1,3-thiazole-4-carboxylate (186 mg, 1.0 mmol) in 50% H$_3$PO$_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated NaHCO$_3$ solution and extracted twice with ether. The organic layers were combined, dried over MgSO$_4$ and concentrated to give methyl 5-ethylthiazole-4-carboxylate (i.e. Cap-173, step a) (134 mg, 78%) as an orange oil (85% pure) which was used directly in the next reaction. R$_f$=1.58 min (Cond.-MD1); LC/MS: Anal. Calcd. for [M+H]$^+$ C$_7$H$_{10}$NO$_2$S: 172.05; found: 172.05.

Cap-173

To a solution of methyl 5-ethylthiazole-4-carboxylate (134 mg) in THF/H$_2$O/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-173 (90 mg, 73%) as an orange solid which was used without further purification. $^1$H NMR (300 MHz, DMSO-d$_6$) δ ppm 12.74-13.04 (1 H, m), 3.20 (2H, q, J=7.3 Hz), 1.25 (3 H, t, J=7.5 Hz). R$_f$=1.27 min (Cond.-MD1); LC/MS: Anal. Calcd. for [M+H]$^+$ C$_6$H$_8$NO$_2$S: 158.03; found: 158.04.

Cap-174

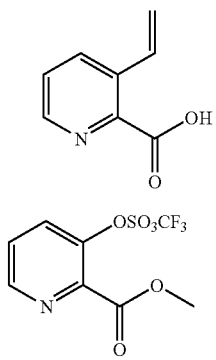

Cap-174, step a

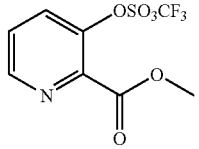

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in $CH_2Cl_2$ (80 mL). The mixture was stirred at 0° C. for 1 h before it was allowed to warm up to room temperature where it stirred for an additional 1 h. The mixture was then quenched with saturated $NaHCO_3$ solution (40 mL) and the organic layer was separated, washed with brine, dried over $MgSO_4$ and concentrated to give methyl 3-(trifluoromethylsulfonyloxy)picolinate (i.e. Cap-174, step a) (3.38 g, 73%) as a dark brown oil (>95% pure) which was used directly without further purification. $^1$H NMR (300 MHz, $CDCl_3$) δ ppm 8.72-8.79 (1 H, m), 7.71 (1 H, d, J=1.5 Hz), 7.58-7.65 (1 H, m), 4.04 (3 H, s). $R_t$=1.93 min (Cond.-MD1); LC/MS: Anal. Calcd. for $[M+H]^+$ $C_8H_7F_3NO_5S$: 286.00; found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through Celite and the pad of Celite was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-$d_6$) δ ppm 8.21 (1 H, d, J=3.7 Hz), 7.81-7.90 (1 H, m), 7.09 (1 H, dd, J=7.7, 4.8 Hz), 6.98 (1 H, dd, J=17.9, 11.3 Hz), 5.74 (1 H, dd, J=17.9, 1.5 Hz), 5.20 (1 H, d, J=11.0 Hz). $R_t$=0.39 min (Cond.-MD1); LC/MS: Anal. Calcd. for $[M+H]^+$ $C_8H_8NO_2$: 150.06; found: 150.07.

Cap-175

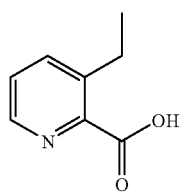

Cap-175, step a

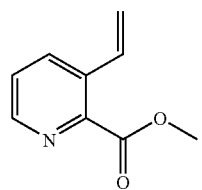

To a solution of methyl 3-(trifluoromethylsulfonyloxy)picolinate (i.e. Cap 174, step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through Celite, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e. Cap-175, step a) (130 mg, 40%) as a yellow oil. $^1$H NMR (300 MHz, $CDCl_3$) δ ppm 8.60 (1 H, dd, J=4.6, 1.7 Hz), 7.94 (1 H, d, J=7.7 Hz), 7.33-7.51 (2 H, m), 5.72 (1 H, d, J=17.2 Hz), 5.47 (1 H, d, J=11.0 Hz), 3.99 (3 H, s). $R_t$=1.29 min (Cond.-MD1); LC/MS: Anal. Calcd. for $[M+H]^+$ $C_9H_{10}NO_2$: 164.07; found: 164.06.

Cap-175, step b

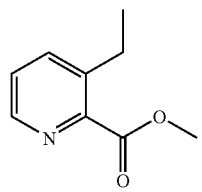

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through Celite and the pad of Celite was washed with methanol. The filtrate was concentrated down to dryness to yield methyl 3-ethylpicolinate (i.e. Cap-175, step b) which was taken directly into the next reaction. $R_t$=1.15 min (Cond.-MD1); LC/MS: Anal. Calcd. for $[M+H]^+$ $C_9H_{12}NO_2$: 166.09; found: 166.09.

Cap-175

To a solution of methyl 3-ethylpicolinate in THF/$H_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-$d_6$) δ ppm 8.47 (1 H, dd, J=4.8, 1.5 Hz), 7.82-7.89 (1 H, m), 7.53 (1 H, dd, J=7.7, 4.8 Hz), 2.82 (2 H, q, J=7.3 Hz), 1.17 (3 H, t, J=7.5 Hz). $R_t$=0.36

Cap-176

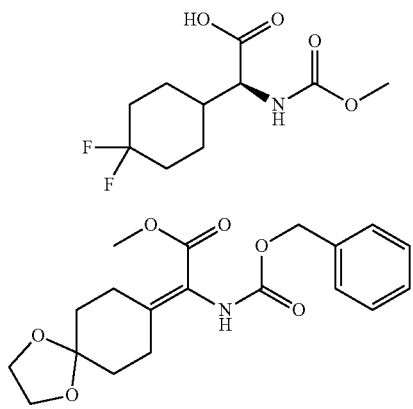

Cap-176, step a

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H$_2$O (100 mL) and brine (100 mL), dried (MgSO$_4$), filtered and concentrated. The residue was purified via Biotage (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5 H, m), 6.02 (1 H, br. s.), 5.15 (2 H, s), 3.97 (4 H, s), 3.76 (3 H, br. s.), 2.84-2.92 (2 H, m), 2.47 (2 H, t, J=6.40 Hz), 1.74-1.83 (4 H, m). LC (Cond, OL1): R$_f$=2.89 min. LC/MS: Anal. Calcd. For [M+Na]$^+$ C$_{19}$H$_{23}$NNaO$_6$: 745.21; found: 745.47.

Cap 176, step b

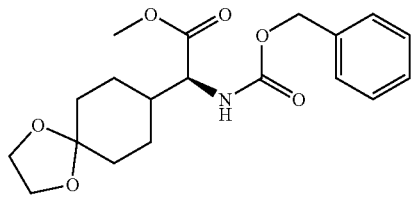

Ester Cap 176, step b was prepared from alkene Cap 176, step a according to the method of Burk, M. J.; Gross, M. F. and Martinez J. P. (*J. Am. Chem. Soc.*, 1995, 117, 9375-9376 and references therein): A 500 mL high-pressure bottle was charged with alkene Cap 176, step a (3.5 g, 9.68 mmol) in degassed MeOH (200 mL) under a blanket of N$_2$. The solution was then charged with (−)-1,2-Bis((2S,5S)-2,5-dimethylphospholano)ethane(cyclooctadiene)rhodium (1) tetrafluoroborate (0.108 g, 0.194 mmol) and the resulting mixture was flushed with N$_2$ (3×) and charged with H$_2$ (3×). The solution was shaken vigorously under 70 psi of H$_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap 176, step b (3.4 g). $^1$H NMR (500 MHz, CDCl$_3$-d) δ ppm 7.28-7.43 (5 H, m), 5.32 (1 H, d, J=9.16 Hz), 5.06-5.16 (2 H, m), 4.37 (1 H, dd, J=9.00, 5.04 Hz), 3.92 (4 H, t, J=3.05 Hz), 3.75 (3 H, s), 1.64-1.92 (4 H, m), 1.37-1.60 (5 H, m). LC (Cond. OL1): R$_f$=1.95 min. LC/MS: Anal. Calcd. For [M+H]$^+$ C$_{19}$H$_{26}$NO$_6$: 364.18; found: 364.27.

Cap 176, step c

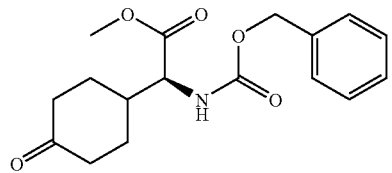

Ester Cap 176, step b (438 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid Na$_2$CO$_3$ with vigorous stirring until the release of gas was no longer visible. Crude product was extracted into 10% ethyl acetate-dichloromethane and the organic layers were combined, dried (MgSO$_4$) filtered and concentrated. The resulting residue was purified via Biotage (0 to 30% EtOAc/Hex; 25 g column) to afford ketone Cap 176, step c (3.86 g) as a clear oil. $^1$H NMR (400 MHz, CDCl$_3$-d) δ ppm 7.28-7.41 (5 H, m), 5.55 (1 H, d, J=8.28 Hz), 5.09 (2 H, s), 4.46 (1 H, dd, J=8.16, 5.14 Hz), 3.74 (3 H, s), 2.18-2.46 (5 H, m), 1.96-2.06 (1 H, m), 1.90 (1 H, ddd, J=12.99, 5.96, 2.89 Hz), 1.44-1.68 (2 H, m, J=12.36, 12.36, 12.36, 12.36, 4.77 Hz). LC (Cond. OL1): R$_f$=1.66 min. LC/MS: Anal. Calcd. For [M+Na]$^+$ C$_{17}$H$_{21}$NNaO$_5$: 342.13; found: 342.10.

Cap 176, step d

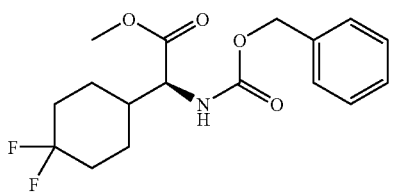

Deoxo-Fluor® (3.13 mL, 16.97 mmol) was added to a solution of ketone Cap 176, step c (2.71 g, 8.49 mmol) in CH$_2$Cl$_2$ (50 mL) followed by addition of a catalytic amount of EtOH (0.149 mL, 2.55 mmol). The resulting yellowish solution was stirred at rt overnight. The reaction was quenched by addition of sat. aq. NaHCO$_3$ (25 mL) and the mixture was extracted with EtOAc (3×75 mL)). The combined organic layers were dried (MgSO$_4$), filtered and dried to give a yellowish oil. The residue was purified via Biotage chromatography (2% to 15% EtOAc/Hex; 90 g column) and a white solid corresponding to the difluoro amino acid dilforide Cap 176, step d (1.5 g) was recovered. $^1$H NMR (400 MHz, CDCl$_3$-d) δ ppm 7.29-7.46 (5 H, m), 5.34 (1 H, d, J=8.28 Hz), 5.12 (2 H, s), 4.41 (1 H, dd, J=8.66, 4.89 Hz), 3.77 (3 H, s), 2.06-2.20 (2 H, m), 1.83-1.98 (1 H, m), 1.60-1.81 (4 H, m), 1.38-1.55 (2H, m). $^{19}$F NMR (376 MHz, CDCl$_3$-d) δ ppm min (Cond.-MD1); LC/MS: Anal. Calcd. for [M+H]$^+$ C$_8$H$_{10}$NO$_2$: 152.07; found: 152.10.

−92.15 (1 F, d, J=237.55 Hz), −102.44 (1 F, d, J=235.82 Hz). LC (Cond. OL1): $R_t$=1.66 min. LC/MS: Anal. Calcd. For [2M+Na]$^+$ $C_{34}H_{42}F_4N_2NaO_8$: 705.28; found: 705.18.

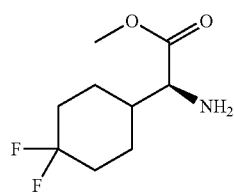

Cap 176, step e

Difluoride Cap 176, step d (4 g, 11.72 mmol) was dissolved in MeOH (120 mL) and charged with Pd/C (1.247 g, 1.172 mmol). The suspension was flushed with $N_2$ (3×) and the reaction mixture was placed under 1 atm of $H_2$ (balloon). The mixture was stirred at ambient temperature for 48 h. The suspension was then filtered though a plug of Celite and concentrated under vacuum to give an oil that corresponded to amino acid Cap 176, step e (2.04 g) and that was used without further purification. $^1$H NMR (400 MHz, DMSO-$d_6$) δ ppm 3.62 (3 H, s), 3.20 (1 H, d, J=5.77 Hz), 1.91-2.09 (2 H, m), 1.50-1.88 (7 H, m), 1.20-1.45 (2 H, m). $^{19}$F NMR (376 MHz, DMSO-$d_6$) δ ppm −89.39 (1 F, d, J=232.35 Hz), −100.07 (1 F, d, J=232.35 Hz). $^{13}$C NMR (101 MHz, DMSO-$d_6$) δ ppm 175.51 (1 C, s), 124.10 (1 C, t, J=241.21, 238.90 Hz), 57.74 (1 C, s), 51.39 (1 C, s), 39.23 (1 C, br. s.), 32.02-33.83 (2 C, m), 25.36 (1 C, d, J=10.02 Hz), 23.74 (1 C, d, J=9.25 Hz). LC (Cond. OL2): $R_t$=0.95 min. LC/MS: Anal. Calcd. For [2M+H]$^+$ $C_{18}H_{31}F_4N_2O_2$: 415.22; found: 415.40.

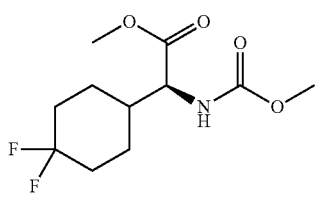

Cap 176, step f

Methyl chloroformate (1.495 mL, 19.30 mmol) was added to a solution of amino acid Cap 176, step e (2 g, 9.65 mmol) and DIEA (6.74 mL, 38.6 mmol) in $CH_2Cl_2$ (100 mL). The resulting solution was stirred at rt for 3 h and volatiles were removed under reduced pressure. The residue was purified via Biotage (0% to 20% EtOAc/Hex; 90 g column). A clear oil that solidified upon standing under vacuum and corresponding to carbamate Cap-176, step f (2.22 g) was recovered. $^1$H NMR (500 MHz, CDCl$_3$-d) δ ppm 5.27 (1 H, d, J=8.55 Hz), 4.39 (1 H, dd, J=8.85, 4.88 Hz), 3.77 (3 H, s), 3.70 (3 H, s), 2.07-2.20 (2 H, m), 1.84-1.96 (1 H, m), 1.64-1.82 (4 H, m), 1.39-1.51 (2 H, m). $^{19}$F NMR (471 MHz, CDCl$_3$-d) δ ppm −92.55 (1 F, d, J=237.13 Hz), −102.93 (1 F, d, J=237.12 Hz). $^{13}$C NMR (126 MHz, CDCl$_3$-d) δ ppm 171.97 (1 C, s), 156.69 (1 C, s), 119.77-125.59 (1 C, m), 57.24 (1 C, br. s.), 52.48 (1 C, br. s.), 52.43 (1 C, s), 39.15 (1 C, s), 32.50-33.48 (2 C, m), 25.30 (1 C, d, J=9.60 Hz), 24.03 (1 C, d, J=9.60 Hz). LC (Cond. OL1): $R_t$=1.49 min. LC/MS: Anal. Calcd. For [M+Na]$^+$ $C_{11}H_{17}F_2NNaO_4$: 288.10; found: 288.03.

Cap-176

A solution of LiOH (0.379 g, 15.83 mmol) in Water (25 mL) was added to a solution of carbamate Cap-176, step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried (MgSO$_4$), filtered and concentrated to give a white foam corresponding to Cap-176 (1.92 g). $^1$H NMR (400 MHz, DMSO-$d_6$) δ ppm 12.73 (1 H, s), 7.50 (1 H, d, J=8.78 Hz), 3.97 (1 H, dd, J=8.53, 6.02 Hz), 3.54 (3 H, s), 1.92-2.08 (2 H, m), 1.57-1.90 (5H, m), 1.34-1.48 (1 H, m), 1.27 (1 H, qd, J=12.72, 3.26 Hz). $^{19}$F NMR (376 MHz, DMSO-$d_6$) δ ppm −89.62 (1 F, d, J=232.35 Hz), −99.93 (1 F, d, J=232.35 Hz). LC (Cond. OL2): $R_t$=0.76 min. LC/MS: Anal. Calcd. For [M−H]$^+$ $C_{10}H_{14}F_2NO_4$: 250.09; found: 250.10.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400, or 500 MHz spectrometer; the chemical shifts (δ) are reported in parts per million. Flash chromatography was carried out on silica gel (SiO$_2$) according to Still's flash chromatography technique (J. Org. Chem., 43:2923 (1978)).

Purity assessment and low resolution mass analysis were conducted on a Shimadzu LC system coupled with Waters MICROMASS® ZQ MS system. It should be noted that retention times may vary slightly between machines. Unless noted otherwise, the LC conditions employed in determining the retention time ($R_t$) were:
Condition 1
Column=Luna 3.0×50 mm 510
Start % B=0
Final % B=100
Gradient time=3 min
Stop time=4 min
Flow Rate=4 mL/min
Wavelength=220 nm
Solvent A=5% CH$_3$CN/95% H$_2$O/10 mm NH$_4$OAc
Solvent B=95% CH$_3$CN/5% H$_2$O/10 mm NH$_4$OAc
Condition 2
Column=Sunfire C18 3.5 um, 4.6×50 mm
Start % B=0
Final % B=100
Gradient time=30 min
Stop time=32 min
Flow Rate=2 mL/min
Wavelength=220 nm
Solvent A=0.1% TFA/95% H$_2$O/5% CH$_3$CN
Solvent B=0.1% TFA/5% H$_2$O$_{195}$% CH$_3$CN
Condition 3
Column=PHENOMENEX®-Luna 3.0×50 mm 510
Start % B=0
Final % B=100
Gradient time=2 min
Stop time=3 min
Flow Rate=4 mL/min
Wavelength=220 nm
Solvent A=0.1% TFA in 10% methanol/90% H$_2$O Solvent B=0.1% TFA in 90% methanol/1.0% H$_2$O

Example CQ-1

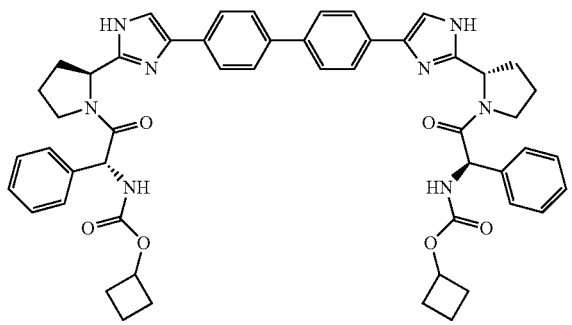

Example CQ-1a

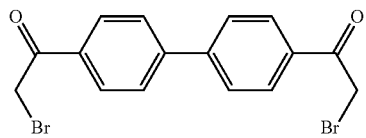

A 1 L, 3-neck round bottom flask, fitted with a nitrogen line, overhead stirrer and thermocouple was charged with 20 g (83.9 mmol, 1 equiv) 1,1'-(biphenyl-4,4'-diyl)diethanone, 200 mL $CH_2Cl_2$ and 8.7 mL (27.1 g, 169.3 mmol, 2.02 quiv) bromine. The mixture was allowed to stir under nitrogen for about 20 h under ambient conditions. The resulting slurry was charged with 200 mL $CH_2Cl_2$ and concentrated down to about 150 mL via vacuum distillation. The slurry was then solvent exchanged into THF to a target volume of 200 mL via vacuum distillation. The slurry was cooled to 20-25° C. over 1 h and allowed to stir at 20-25° C. for an additional hour. The off-white crystalline solids were filtered and washed with 150 mL $CH_2Cl_2$. The product was dried under vacuum at 60° C. to provide 27.4 g (69.2 mmol, 82%) of the desired product: $^1$H NMR (400 MHz, $CDCl_3$) δ 7.95-7.85 (m, 4H), 7.60-7.50 (m, 4H), 4.26 (s, 4H); $^{13}$C NMR (100 MHz, $CDCl_3$) δ 191.0, 145.1, 133.8, 129.9, 127.9, 30.8; IR (KBr, cm$^{-1}$) 3007, 2950, 1691, 1599, 1199; Anal calcd for $C_{16}H_{12}Br_2O_2$: C, 48.52; H, 3.05; Br, 40.34. Found: C, 48.53; H, 3.03; Br, 40.53. HRMS calcd for $C_{16}H_{13}Br_2O_2$ (M+H; DCI$^+$): 394.9282. Found: 394.9292. mp 224-226° C.

Example CQ-1b

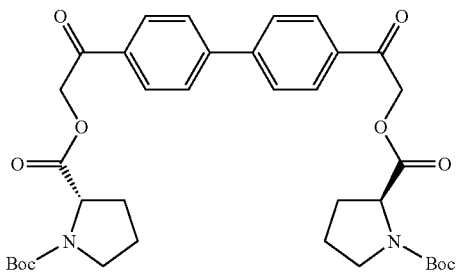

A 500 mL jacketed flask, fitted with a nitrogen line, thermocouple and overhead stirrer, was charged with 20 g (50.5 mmol, 1 equiv) of Example CQ-1a, 22.8 g (105.9 moles, 2.10 equiv), 1-(tent-butoxycarbonyl)-L-proline, and 200 mL acetonitrile. The slurry was cooled to 20° C. followed by the addition of 18.2 mL (13.5 g, 104.4 mmol, 2.07 equiv) DIPEA. The slurry was warmed to 25° C. and allowed to stir for 3 h. The resulting clear, organic solution was washed with 3×100 mL 13 wt % aqueous NaCl. The rich acetonitrile solution was solvent exchanged into toluene (target volume=215 mL) by vacuum distillation until there was less than 0.5 vol % acetonitrile.

Example CQ-1c

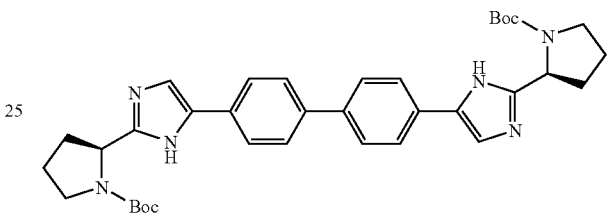

The above toluene solution of Example CQ-1b was charged with 78 g (1.011 moles, 20 equiv) ammonium acetate and heated to 95-100° C. The mixture was allowed to stir at 95-100° C. for 15 h. After reaction completion, the mixture was cooled to 70-80° C. and charged with 7 mL acetic acid, 40 mL n-butanol, and 80 mL of 5 vol % aqueous acetic acid. The resulting biphasic solution was split while maintaining a temperature >50° C. The rich organic phase was charged with 80 mL of 5 vol % aqueous acetic acid, 30 mL acetic acid and 20 mL n-butanol while maintaining a temperature >50° C. The resulting biphasic solution was split while maintaining a temperature >50° C. and the rich organic phase was washed with an additional 80 mL of 5 vol % aqueous acetic acid. The rich organic phase was then solvent exchanged into toluene to a target volume of 215 mL by vacuum distillation. While maintaining a temperature >60° C., 64 mL MeOH was charged. The resulting slurry was heated to 70-75° C. and aged for 1 h. The slurry was cooled to 20-25° C. over 1 h and aged at that temperature for an additional hour. The slurry was filtered and the cake was washed with 200 mL 10:3 toluene:MeOH. The product was dried under vacuum at 70° C., resulting in 19.8 g (31.7 mmol, 63%) of the desired product: $^1$H NMR (400 MHz, DMSO-$d_6$) δ 13.00-11.00 (s, 2H), 7.90-7.75 (m, 4H), 7.75-7.60 (m, 4H), 7.60-7.30 (s, 2H), 4.92-4.72 (m, 2H), 3.65-3.49 (m, 2H), 3.49-3.28 (m, 2H), 2.39-2.1 (m, 2H), 2.10-1.87 (m, 6H), 1.60-1.33 (s, 8H), 1.33-1.07 (s, 10H); $^{13}$C NMR (100 MHz, DMSO-$d_6$) δ 154.1, 153.8, 137.5, 126.6, 125.0, 78.9, 78.5, 55.6, 55.0, 47.0, 46.7, 33.7, 32.2, 28.5, 28.2, 24.2, 23.5; IR (KBr, cm-1) 2975, 2876, 1663, 1407, 1156, 1125; HRMS calcd for $C_{36}H_{45}N_6O_4$ (M+H; ESI$^+$): 625.3502. Found: 625.3502. mp 190-195° C. (decomposed).

Example CQ-1d

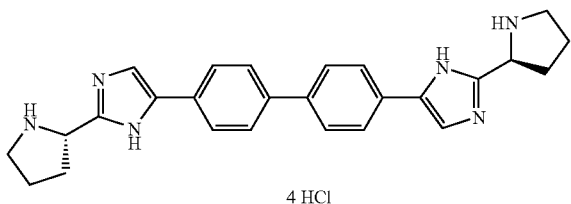

4 HCl

To a 250 ml reactor equipped with a nitrogen line and overhead stirrer, 25.0 g of Example CQ-1c (40.01 mmol, 1 equiv) was charged followed by 250 mL methanol and (400.1 mmol, 10 equiv) concentrated hydrogen chloride. The temperature was increased to 50° C. and agitated at 50° C. for 5 h. The resulting slurry was cooled to 20-25° C. and held with agitation for ca. 18 h. Filtration of the slurry afforded a solid which was washed successively with 100 ml 90% methanol/water (V/V) and 2×100 ml of methanol. The wet cake was dried in a vacuum oven at 50° C. overnight to give 18.12 g (31.8 mmol, 79.4%) of the desired product.

Example CQ-1e

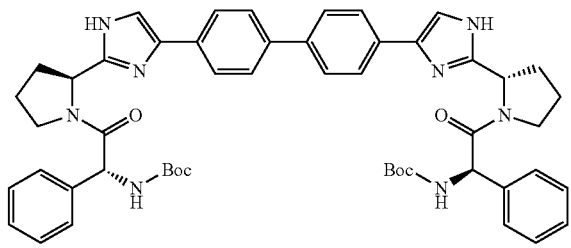

Diisopropyl ethylamine (1.837 mL, 10.52 mmol) was added to a mixture of Example CQ-1d (1 g, 1.753 mmol), and (R)-2-(tert-butoxycarbonylamino)-2-phenylacetic acid (0.969 g, 3.86 mmol) in 30 mL of DMF, followed by 1-propylphosphonic acid cyclic anhydride (3.85 mL, 6.59 mmol). The resulting solution was stirred at room temperature overnight. The solvent was then removed under vacuum and the residue was purified by reverse phase HPLC (CH$_3$OH/H$_2$O/TFA) to give the TFA salt of Example CQ-1e (1.4 g, 1.571 mmol, 90% yield) as a light yellow solid. $^1$H NMR (400 MHz, CDCl$_3$) δ 7.27-7.68 (20H, m), 5.33-5.90 (4H, m), 4.00-4.15 (2 H, m), 3.21-3.39 (2 H, m), 1.58-2.50 (14 H, m), 1.24-1.47 (18 H, m), 0.92-1.05 (4H, m); LC/MS (Cond. 1): R$_t$=2.26 min; Anal. Calcd. for [M+H]$^+$ C$_{52}$H$_{59}$N$_8$O$_6$: 891.46; found 891.71.

Example CQ-1f

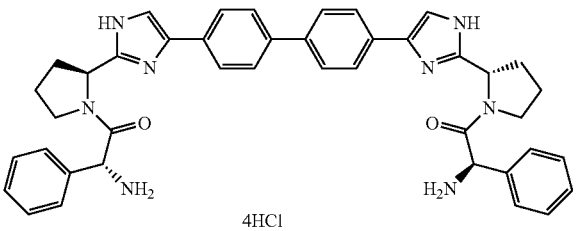

4HCl

HCl (5 mL, 4N in dioxanes) was added to a solution of Example CQ-1e (1.4 g, 1.571 mmol) in 5 mL of CH$_2$Cl$_2$. The resulting mixture was stirred at room temperature for 2 hours. The solvent was removed under vacuum and the residue was triturated with ether. The resulting solid was filtered, washed with ether and collected to give Example CQ-1f 4HCl (1.26 g, 1.506 mmol, 96% yield) as a light yellow solid. $^1$H NMR (500 MHz, DMSO-d$_6$) δ 8.81 (6 H, br. s.), 8.21 (2 H, s), 8.09-8.18 (4 H, m), 7.90-8.00 (4 H, m), 7.55-7.65 (4 H, m), 7.40-7.56 (6 H, m), 5.38-5.52 (4 H, m), 4.14-4.24 (2 H, m), 2.96-3.08 (2 H, m), 2.25-2.36 (2 H, m), 2.08-2.19 (2 H, m), 1.83-2.03 (4 H, m), 1.42-1.55 (2 H, m), 0.94 (2H, t, J=6.41 Hz); LC/MS (Cond. 1): R$_t$=1.72 min; Anal. Calcd. for [M+H]$^+$ C$_{42}$H$_{43}$N$_8$O$_2$ 691.35; found 691.52.

Example CQ-1

A solution of diisopropyl ethylamine (0.104 mL, 0.598 mmol) in 1 mL of CH$_2$Cl$_2$ was added dropwise at 0° C. to a mixture of cyclobutanol (43.1 mg, 0.598 mmol) and triphosgene (89 mg, 0.299 mmol) in 2 mL of CH$_2$Cl$_2$. The resulting mixture was stirred at room temperature for 1 hour and then added dropwise to a mixture of Example CQ-1f (50 mg, 0.060 mmol) and DIPEA (0.042 mL, 0.239 mmol) in 1 mL of CH$_2$Cl$_2$. The reaction mixture was stirred at room temperature for 3 hours. Ammonia (3 mL, 2 M in Methanol) was then added and stirring continued at room temperature for an additional 5 hours. The solvent was then removed under vacuum and the residue was purified by reverse phase HPLC (CH$_3$CN/H$_2$O/NH$_4$OAc) to give Example CQ-1 (17 mg, 32.1%) as a white solid. $^1$H NMR (500 MHz, DMSO-d$_6$) δ 6.82-7.98 (22 H, m), 5.28-5.57 (2 H, m), 4.97-5.13 (2 H, m), 4.75-4.88 (2 H, m), 3.80-3.97 (1 H, m), 3.44-3.67 (1 H, m), 3.04-3.22 (2 H, m), 2.10-2.29 (4 H, m), 1.75-2.11 (12 H, m), 1.60-1.75 (2 H, m), 1.41-1.60 (2 H, m); HPLC (Cond. 2): R$_t$=13.98 min; >95% homogeneity index; LCMS: Anal. Calcd. for [M+H]$^+$ C$_{52}$H$_{55}$N$_8$O$_6$: 887.43; found 887.61; HRMS: Anal. Calcd. for C$_{52}$H$_{55}$N$_8$O$_6$: 887.4245; found 887.4224.

Example CQ-2

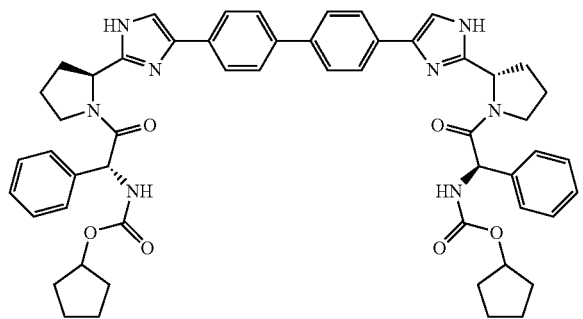

Cyclopentyl chloroformate (28.4 mg, 0.191 mmol) was added to a mixture of Example CQ-1f (40 mg, 0.048 mmol) and diisopropyl ethylamine (0.067 mL, 0.382 mmol) in CH$_2$Cl$_2$ (2 mL). The resulting solution was stirred at room temperature for 1 hour and then, ammonia (2 mL, 2 M in methanol) was added. Stirring continued at room temperature for an additional 3 hours. The solvent was then removed under vacuum and the residue was purified by reverse phase HPLC (CH$_3$CN/H$_2$O/NH$_4$OAc) to give Example CQ-2 (23 mg, 0.025 mmol, 52.6%) as a white solid. $^1$H NMR (400 MHz, DMSO-d$_6$) δ 6.72-8.03 (22H, m), 5.22-5.65 (3 H, m), 4.78-5.19 (3 H, m), 3.78-4.06 (2 H, m), 2.85-3.75 (overlap with water peak, m), 1.27-2.25 (24 H, m); HPLC (Cond. 2): R$_t$=17.59 min; >95% homogeneity index; LCMS: Anal.

Calcd. for [M+H]+ C$_{54}$H$_{59}$N$_8$O$_6$: 915.46; found 915.70; HRMS: Anal. Calcd. for [M+H]+ C$_{54}$H$_{59}$N$_8$O$_6$: 915.4558; found 915.4538.

Examples CQ-3 and CQ-4

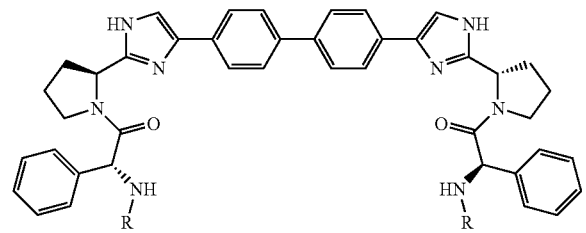

Example CQ-3 was prepared by replacing cyclopropanol for cyclobutanol and using the same method described for Example CQ-1. Cyclopropanol can be synthesized according to literature procedures (Salaun, J. et al., *J. Org. Chem.*, 45:4129-4135 (1980)).

Example CQ-4 was prepared by replacing cyclohexyl chloroformate for cyclopentyl chloroformate and using the same method described for Example CQ-2.

| Example | R | R$_t$ (HPLC-Cond); % homogeneity index; MS data |
|---|---|---|
| CQ-3 | cyclopropyl | R$_t$: 14.00 min. (Cond. 2); >95%; LCMS: Anal. Calcd. for [M + H]+ C$_{50}$H$_{51}$N$_8$O$_6$: 859.39; found 859.51; HRMS: Anal. Calcd. for [M + H]+ C$_{50}$H$_{51}$N$_8$O$_6$: 859.3932; found 859.3910 |
| CQ-4 | cyclohexyl | 18.14 minutes (Cond. 2); >95%; LCMS: Anal. Calcd. for [M + H]+ C$_{56}$H$_{63}$N$_8$O$_6$ 943.49; found 943.74; HRMS: Anal. Calcd. for [M + H]+ C$_{56}$H$_{63}$N$_8$O$_6$ 943.4871; found 943.4848 |

Example CQ-5

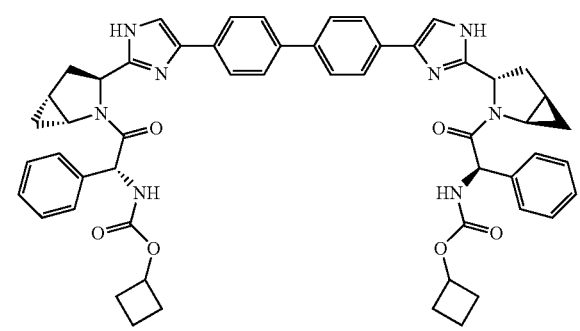

Example CQ-5a

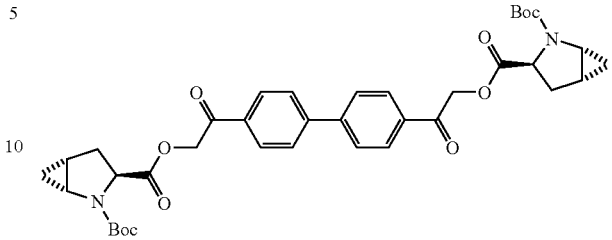

Diisopropyl ethylamine (1.81 mL, 10.4 mmol) was slowly added to acetonitrile (20 mL) solution of (1R,3S,5R)-2-(tert-butoxycarbonyl)-2-azabicyclo[3.1.0]hexane-3-carboxylic acid (2.36 g, 10.4 mmol) and Example CQ-1a (2.0 g, 5.05 mmol), and the reaction mixture was stirred at ambient conditions for 16 hr. The solvent was evaporated and the residue was partitioned between ethyl acetate and water (1:1, 40 mL each). The organic layer was washed with Sat. NaHCO$_3$ (2×10 mL), brine, dried (Na$_2$SO$_4$), filtered, and concentrated in vacuo to afford Example CQ-5a (3.58 g) as a viscous amber oil, which solidified upon storage in a refrigerator. $^1$H NMR (DMSO-d$_6$, 400 MHz): δ 8.20 (m, 4H), 7.97 (d, J=8.5, 4H), 5.71-5.48 (m, 4H), 4.69 (m, 2H), 3.44 (m, 2H), 3.3 (m, 2H), 2.76-2.67 (m, 2 H), 2.27 (m, 2H), 1.60 (m, 2H), 1.44/1.38 (two s, 18H), 0.78 (m, 2H), 0.70 (m, 2H). LC (Cond. 3): R$_t$=1.70 min; LC/MS: the molecular ion was not picked up.

Example CQ-5b

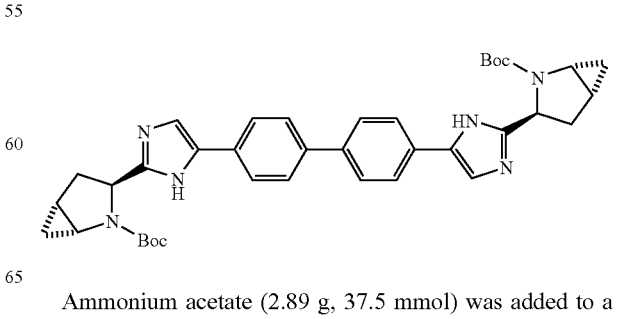

Ammonium acetate (2.89 g, 37.5 mmol) was added to a toluene (20 mL) solution of Example CQ-5a (2.58 g, 3.75 mmol), and the resulting mixture was heated at 120° C. for 4.5 hr, while azaetroping the water that is formed with a Dean-Stark set-up. The reaction mixture was cooled to room temperature and the volatile component was removed in vacuo. Sat. NaHCO$_3$ solution (10 mL) was added to the solid and the mixture was stirred for 30 min, and the solid was filtered, dried in vacuo and submitted to a BIOTAGE® purification (28-100% EtOAc/hexanes) to afford Example CQ-5b as light yellow solid (0.6 g). LC (Cond. 3): R$_t$=1.52 min; LC/MS: Anal. Calcd. for [M+H]$^+$ C$_{38}$H$_{45}$N$_6$O$_4$: 649.35; found 649.78.

Example CQ-5c

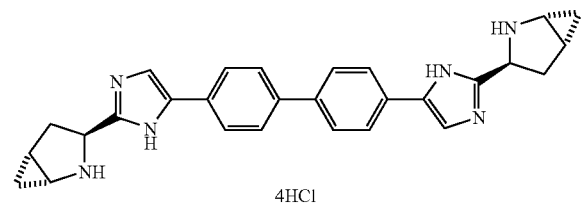

4HCl

4 N HCl in dioxane (5 mL) was added to a ice-water cooled dioxane (16 mL) solution of Example CQ-5b (0.8 g, 1.2 mmol), the ice-water bath was removed and the mixture was stirred at ambient condition for 4 hr. Big chunks of solid that formed during the reaction were broken up with a spatula. Removal of the volatile component in vacuo afforded pyrrolidine Example CQ-5c (0.4 HCl) as yellow solid (0.73 g). $^1$H NMR (DMSO-d$_6$, 400 MHz): δ 7.90 (d, J=8.3, 4H), 7.84 (br s, 2H), 7.79 (d, J=8.3, 4H), 5.24 (m, 2H), 3.38 (m, 2H), 2.71 (m, 2H), ~2.50 (2H, overlapped with solvent signal), 1.93 (m, 2H), 1.38 (m, 2H), 0.96 (m, 2H). LC (Cond. 1): RT=1.03 min; LC/MS: Anal. Calcd. for [M+H]$^+$ C$_{28}$H$_{29}$N$_6$: 449.25; found 449.59.

Example CQ-5d

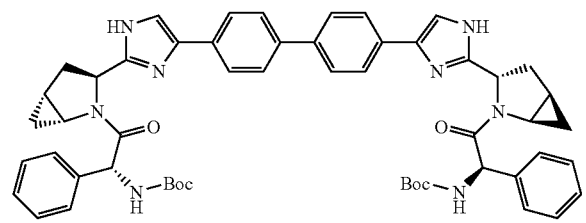

Example CQ-5d was synthesized as a TFA salt from Example CQ-5C and (R)-2-(tert-butoxycarbonylamino)-2-phenylacetic acid according to the procedure described for the synthesis of Example CQ-1e. $^1$H NMR (500 MHz, CDCl$_3$) δ 6.86-8.06 (22 H, m), 5.53-6.02 (2 H, m), 5.04-5.55 (2 H, m), 3.54-4.04 (2 H, m), 2.23-2.85 (2 H, m), 1.72-2.21 (2 H, m), 1.05-1.65 (20 H, m), 0.34-0.83 (2 H, m), −0.49-0.15 (2 H, m); LC/MS (Cond. 1): R$_t$=2.34 min.; Anal. Calcd. for [M+H]$^+$ C$_{54}$H$_{59}$N$_8$O$_6$: 915.46; found 915.72.

Example CQ-5e

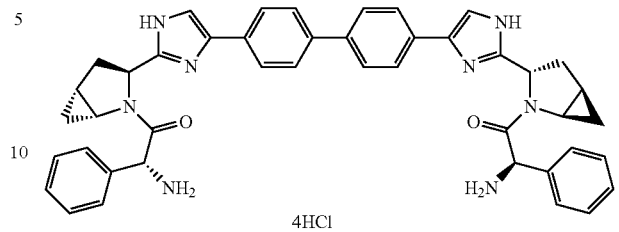

4HCl

Example CQ-5e was synthesized as an HCl salt from Example CQ-5d according to the procedure described for the synthesis of Example CQ-1f. $^1$H NMR (500 MHz, DMSO-d$_6$) δ 8.80 (6 H, br. s.), 8.14-8.27 (2 H, m), 8.00-8.11 (4 H, m), 7.87-7.99 (4 H, m), 7.55-7.62 (4 H, m), 7.44-7.54 (6 H, m), 5.65-5.74 (2 H, m), 5.21-5.32 (2 H, m), 3.91-4.02 (2H), 2.36-2.46 (4 H, m), 1.79-1.92 (2 H, m), 0.44-0.56 (2 H, m), −0.14-0.01 (2 H, m); LC/MS (Cond. 1): R$_t$=1.72 min.; Anal. Calcd. for [M+H]$^+$ C$_{44}$H$_{43}$N$_8$O$_2$: 715.35; found 715.53.

Example CQ-5

Example CQ-5 was synthesized from Example CQ-5e and cyclobutanol using the same method described for the synthesis of Example CQ-1. $^1$H NMR (400 MHz, DMSO-d$_6$) δ 7.64-7.95 (9 H, m), 7.52-7.63 (3 H, m), 7.27-7.52 (10 H, m), 5.71 (2H, d, J=7.28 Hz), 5.01 (2 H, dd, J=8.16, 2.89 Hz), 4.77-4.90 (2 H, m), 3.63-3.77 (2H, m), 2.37-2.48 (2 H, m), 2.06-2.31 (6 H, m), 1.88-2.05 (4 H, m), 1.74-1.86 (2H, m), 1.62-1.75 (2 H, m), 1.44-1.62 (2 H, m), 0.59-0.77 (2 H, m), −0.21-0.06 (2H, m); HPLC (Cond. 2): R$_t$=17.19 min.; >95% homogeneity index; LCMS: Anal. Calcd. for [M+H]$^+$ C$_{54}$H$_{55}$N$_8$O$_6$: 911.42; found 911.59; HRMS: Anal. Calcd. for [M+H]$^+$ C$_{54}$H$_{55}$N$_8$O$_6$: 911.4245; found 911.4226.

Example CQ-6

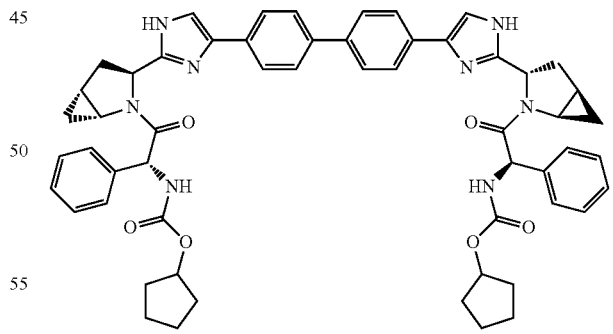

Example CQ-6 was synthesized from Example CQ-5e and cyclopentyl chloroformate using the same method described for the synthesis of Example CQ-2. $^1$H NMR (500 MHz, DMSO-d$_6$) δ 7.79-7.89 (4 H, m), 7.65-7.74 (4 H, m), 7.54-7.62 (2 H, m), 7.29-7.52 (12 H, m), 5.71 (2 H, d, J=7.32 Hz), 4.92-5.04 (4 H, m), 3.63-3.80 (2 H, m), 2.38-2.48 (2 H, m), 2.05-2.20 (2 H, m), 1.69-1.85 (6 H, m), 1.30-1.70 (14 H, m), 0.58-0.73 (2 H, m), −0.32-0.06 (2 H, m); HPLC (Cond. 2): R$_t$=15.21 min.; >95% homogeneity index; LCMS: Anal.

Calcd. for [M+H]+ C56H59N8O6: 939.46; found 939.73; HRMS: Anal. Calcd. for [M+H]+ C56H59N8O6: 939.4558; found 939.4533.

Examples CQ-7 and CQ-8

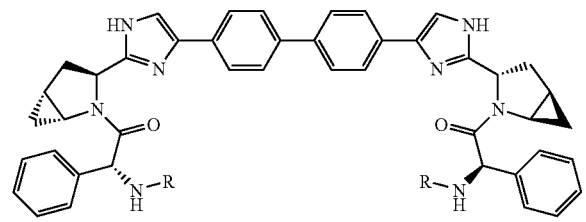

Example CQ-7 was synthesized from Example CQ-5e and cyclopropanol using the same method described for the synthesis of Example CQ-1. Example CQ-8 was synthesized from Example CQ-5e and cyclohexyl chloroformate using the same method described for the synthesis of Example CQ-2.

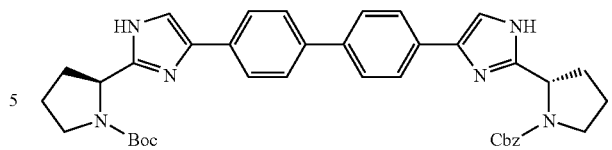

Biological Activity

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53. Assay methods incorporating luciferase reporters have also been used as described (Apath.com).

HCV-neo replicon cells and replicon cells containing mutations in the NS5A region were used to test the currently described family of compounds. The compounds were determined to have more than 10-fold less inhibitory activity on cells containing mutations than wild-type cells. Thus, the compounds of the present disclosure can be effective in inhibiting the function of the HCV NS5A protein and are understood to be as effective in combinations as previously described in application PCT/US2006/022197 and commonly owned WO/04014852. Further, the compounds of the present disclosure can be effective against the HCV 1b genotype. It should also be understood that the compounds of the present disclosure can inhibit multiple genotypes of HCV. Table 2 shows the EC$_{50}$ (Effective 50% inhibitory concentration) values of representative compounds of the present disclosure against the HCV 1b genotype. In one embodiment, compounds of the present disclosure are active against the 1a, 1b, 2a, 2b, 3a, 4a, and 5a genotypes. EC$_{50}$ values against HCV 1b are as follows: A=5 pM to 5 nM.

| Example | R | R$_t$ (HPLC-Cond); % homogeneity index; MS data |
|---|---|---|
| CQ-7 | cyclopropyl-O-C(=O)- | 16.44 min. (Cond. 2); >95%; LCMS: Anal. Calcd. for [M + H]+ C$_{52}$H$_{51}$N$_8$O$_6$: 883.39; found 883.50; HRMS: Anal. Calcd. for [M + H]+ C$_{52}$H$_{51}$N$_8$O$_6$: 883.3932; found 883.3914 |
| CQ-8 | cyclohexyl-O-C(=O)- | 16.00 min. (Cond. 2); >95%; LCMS: Anal. Calcd. for [M + H]+ C$_{58}$H$_{63}$N$_8$O$_6$: 967.49; found 967.75; HRMS: Anal. Calcd. for [M + H]+ C$_{58}$H$_{63}$N$_8$O$_6$: 967.4871; found 967.4848 |

It will be evident to one skilled in the art that the chemistry described above is equally applicable to the synthesis of analogs where the phenyl group of the glycine moiety is replaced with a hydrogen or an alkyl group at R$^1$ & R$^2$, as shown below.

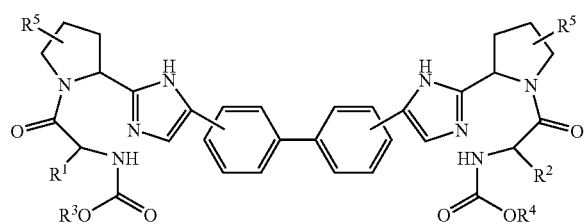

In addition, analogs containing two differing glycine derivatives, where the difference could reside at either R$^1$/R$^2$ or R$^3$/R$^4$, could be prepared by employing a differential protecting group for the pyrrolidine moieties as exemplified in commonly owned WO2008/021927 with intermediate compounds such as the one shown below.

TABLE 2

| Example | 1b (μM) Range | Name |
|---|---|---|
| CQ-1 | A | Cyclobutyl ((1R)-2-((2S)-2-(4-(4'-(2-((2S)-1-((2R)-2-(((cyclobutyloxy)carbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate |

TABLE 2-continued

| Example | 1b (μM) | Range | Name |
|---|---|---|---|
| CQ-2 | 1.2E−5 | A | Cyclopentyl ((1R)-2-((2S)-2-(4-(4'-(2-((2S)-1-((2R)-2-(((cyclopentyloxy)carbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate |
| CQ-3 | | A | Cyclopropyl ((1R)-2-((2S)-2-(4-(4'-(2-((2S)-1-((2R)-2-(((cyclopropyloxy)carbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate |
| CQ-4 | | A | Cyclohexyl ((1R)-2-((2S)-2-(4-(4'-(2-((2S)-1-((2R)-2-(((cyclohexyloxy)carbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate |
| CQ-5 | | A | Cyclobutyl ((1R)-2-((1R,3S,5R)-3-(4-(4'-(2-((1R,3S,5R)-2-((2R)-2-(((cyclobutyloxy)carbonyl)amino)-2-phenylacetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-2-oxo-1-phenylethyl)carbamate |
| CQ-6 | | A | Cyclopentyl ((1R)-2-((1R,3S,5R)-3-(4-(4'-(2-((1R,3S,5R)-2-((2R)-2-(((cyclopentyloxy)carbonyl)amino)-2-phenylacetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-2-oxo-1-phenylethyl)carbamate |
| CQ-7 | 6.1E−6 | A | Cyclopropyl ((1R)-2-((1R,3S,5R)-3-(4-(4'-(2-((1R,3S,5R)-2-((2R)-2-(((cyclopropyloxy)carbonyl)amino)-2-phenylacetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-2-oxo-1-phenylethyl)carbamate |
| CQ-8 | | A | Cyclohexyl ((1R)-2-((1R,3S,5R)-3-(4-(4'-(2-((1R,3S,5R)-2-((2R)-2-(((cyclohexyloxy)carbonyl)amino)-2-phenylacetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-2-oxo-1-phenylethyl)carbamate |

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. Compounds of the present disclosure may inhibit multiple genotypes of HCV.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I)

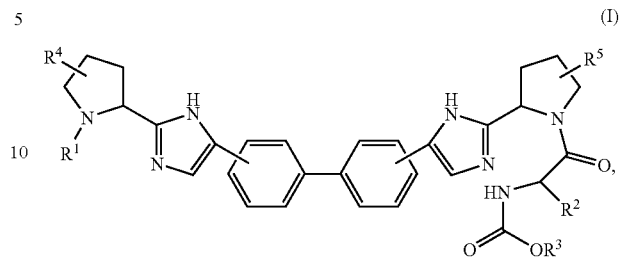

or a pharmaceutically acceptable salt thereof, wherein
$R^1$ is selected from hydrogen, —C(O)$R^6$, and

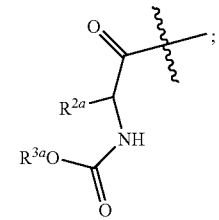

$R^2$ and $R^{2a}$ are independently selected from hydrogen, alkyl, and aryl;
$R^3$ is cycloalkyl;
$R^{3a}$ is cycloalkyl;
$R^4$ and $R^5$ are independently selected from hydrogen and alkyl; wherein the alkyl can optionally form a fused three- to six-membered ring with an adjacent carbon atom or optionally form a spirocyclic three- to six-membered ring with the carbon to which it is attached; and
$R^6$ is selected from alkoxy, alkyl, arylalkoxy, arylalkyl, cycloalkyl, heterocyclyl, heterocyclylalkyl, (NR$^c$R$^d$)alkenyl, and (NR$^c$R$^d$)alkyl.

2. A compound of claim 1, or a pharmaceutically acceptable salt thereof, wherein $R^1$ is C(O)$R^6$.

3. A compound of claim 1, or a pharmaceutically acceptable salt thereof, wherein $R^1$ is

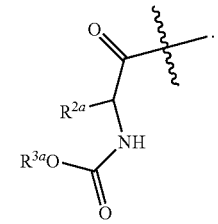

4. A compound of claim 3, or a pharmaceutically acceptable salt thereof, wherein $R^2$ and $R^{2a}$ are each phenyl.

5. A compound of claim 4, or a pharmaceutically acceptable salt thereof, wherein $R^4$ and $R^5$ are each hydrogen.

6. A compound of claim 4, or a pharmaceutically acceptable salt thereof, wherein $R^4$ and $R^5$ are each alkyl, wherein each alkyl group can optionally form a fused three- to six-membered ring with an adjacent carbon atom or optionally form a spirocyclic three- to six-membered ring with the carbon to which it is attached.

7. A compound of claim 6, or a pharmaceutically acceptable salt thereof, wherein $R^4$ and $R^5$ are each alkyl, wherein each alkyl group forms a fused three-membered ring with an adjacent carbon atom.

8. A compound of Formula (II)

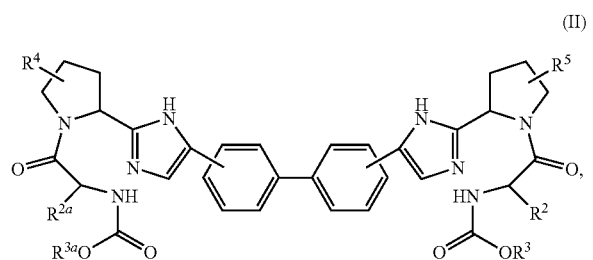

(II)

or a pharmaceutically acceptable salt thereof, wherein
$R^2$ and $R^{2a}$ are independently selected from hydrogen, alkyl, and phenyl;
$R^3$ is $C_{3-7}$ cycloalkyl;
$R^{3a}$ is $C_{3-7}$ cycloalkyl; and
$R^4$ and $R^5$ are independently selected from hydrogen and alkyl; wherein the alkyl can optionally form a fused three-membered ring with an adjacent carbon atom.

9. A compound selected from
cyclobutyl ((1R)-2-((2S)-2-(4-(4'-(2-((2S)-1-(2R)-2-(((cyclobutyloxy)carbonyl)amino)-2-phenylacetyl)-2-pyrrolidinyl)-1H-imidazol -5-yl)-4-biphenylyl)-1H-imidazol-2-yl)-1-pyrrolidinyl)-2-oxo-1-phenylethyl)carbamate;
cyclopentyl ((1R)-2-((2S)-2-(4-(4'-(2-((2S)-1-(2R)-2-(((cyclopentyloxy)carbonyl)amino)-2-phenylacetyl)-2-pyrrolidinyl)-1H-imidazol -5-yl)-4-biphenylyl)-1H-imidazol-2-yl)-1-pyrrolidinyl)-2-oxo-1-phenylethyl)carbamate;
cyclopropyl ((1R)-2-((2S)-2-(4-(4'-(2-((2S)-1-((2R)-2-(((cyclopropyloxy)carbonyl)amino)-2-phenylacetyl)-2-pyrrolidinyl)-1H-imidazol -5-yl)-4-biphenylyl)-1H-imidazol-2-yl)-1-pyrrolidinyl)-2-oxo-1-phenylethyl)carbamate;
cyclohexyl ((1R)-2-((2S)-2-(4-(4'-(2-((2S)-1-((2R)-2-(((cyclohexyloxy)carbonyl)amino)-2-phenylacetyl)-2-pyrrolidinyl)-1H-imidazol -5-yl)-4-biphenylyl)-1H-imidazol-2-yl)-1-pyrrolidinyl)-2-oxo-1-phenylethyl)carbamate;
cyclobutyl ((1R)-2-((1R,3S,5R)-3-(4-(4'-(2-((1R,3S,5R)-2-((2R)-2-(((cyclobutyloxy)carbonyl)amino)-2-phenylacetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-2-oxo-1-phenylethyl)carbamate;
cyclopentyl ((1R)-2-((1R,3S,5R)-3-(4-(4'-(2-((1R,3S,5R)-2-((2R)-2-(((cyclopentyloxy)carbonyl)amino)-2-phenylacetyl)-2-azabicyclo[3.1.0]hex-3-yl)- 1H-imidazol-5-yl)-4-biphenylyl)-1H-imidazol-2-yl)-2-azabicyclo[3.1.0]hex-2-yl)-2-oxo-1-phenylethyl) carbamate;
cyclohexyl ((1R)-2-((1R,3S,5R)-3-(4-(4'-(2-((1R,3S,5R)-2-((2R)-2-(((cyclohexyloxy)carbonyl)amino)-2-phenylacetyl)-2-azabicyclo[3.1.0]hex-3-yl)- 1H-imidazol-5-yl)-4-biphenylyl)-1H-imidazol-2-yl)-2-azabicyclo [3.1.0]hex-2-yl)-2-oxo-1-phenylethyl)carbamate; and
cyclopropyl ((1R)-2-((1R,3S,5R)-3-(4-(4'-(2-((1R,3S,5R)-2-((2R)-2-(((cyclopropyloxy)carbonyl)amino)-2-phenylacetyl)-2-azabicyclo[3.1.0]hex-3-yl)- 1H-imidazol-5-yl)-4-biphenylyl)-1H-imidazol-2-yl)-2-azabicyclo[3.1.0]hex-2-yl)-2-oxo-1-phenylethyl) carbamate;

or a pharmaceutically acceptable salt thereof.

10. A composition comprising a compound of claim 1, or a pharmaceutically acceptable salt thereof, and a pharmaceutically acceptable carrier.

11. The composition of claim 10 further comprising an interferon and/or a ribavirin.

12. The composition of claim 11 wherein the interferon is selected from interferon alpha 2B, pegylated interferon alpha, consensus interferon, interferon alpha 2A, and lymphoblastoid interferon tau.

13. The composition of claim 10 further comprising a compound selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

14. A method of treating an HCV infection in a patient, comprising administering to the patient a therapeutically effective amount of a compound of claim 1, or a pharmaceutically acceptable salt thereof.

15. The method of claim 14 further comprising administering an interferon and/or a ribavirin prior to, after or simultaneously with the compound of claim 1, or a pharmaceutically acceptable salt thereof.

16. The method of claim 15 wherein the interferon is selected from interferon alpha 2B, pegylated interferon alpha, consensus interferon, interferon alpha 2A, and lymphoblastoid interferon tau.

17. The method of claim 14 further comprising administering a compound selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine prior to, after or simultaneously with the compound of claim 1, or a pharmaceutically acceptable salt thereof.

* * * * *

UNITED STATES PATENT AND TRADEMARK OFFICE
CERTIFICATE OF CORRECTION

PATENT NO. : 8,138,215 B2  Page 1 of 1
APPLICATION NO. : 12/780415
DATED : March 20, 2012
INVENTOR(S) : Omar D. Lopez et al.

It is certified that error appears in the above-identified patent and that said Letters Patent is hereby corrected as shown below:

On the Title Page:

Item (56), References Cited, under FOREIGN PATENT DOCUMENTS:
    Column 2, delete "WO    WO-2010132601    * 11/2010".

In the Specification:
    Column 4, line 27, change "Imiqimod" to -- Imiquimod --.
    Column 4, line 65, change "Imiqimod" to -- Imiquimod --.

In the Claims:

Claim 9:
    Column 123, line 29, change "-(2R)-" to -- -((2R)- --.
    Column 123, line 34, change "-(2R)-" to -- -((2R)- --.

Claim 13:
    Column 124, line 31, change "Imiqimod" to -- Imiquimod --.
    Column 124, line 31, change "5'-monophospate" to -- 5'-monophosphate --.

Claim 17:
    Column 124, line 49, change "Imiqimod" to -- Imiquimod --.
    Column 124, line 49, change "5'-monophospate" to -- 5'-monophosphate --.

Signed and Sealed this
Sixteenth Day of October, 2012

David J. Kappos
*Director of the United States Patent and Trademark Office*